(12) United States Patent
Walter

(10) Patent No.: US 7,718,693 B2
(45) Date of Patent: May 18, 2010

(54) RECEPTOR ANTAGONISTS AND THEIR METHODS OF USE

(75) Inventor: Daryl Simon Walter, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 11/772,977

(22) Filed: Jul. 3, 2007

(65) Prior Publication Data

US 2008/0009541 A1    Jan. 10, 2008

(30) Foreign Application Priority Data

| Jul. 6, 2006 | (GB) | ................... 0613473.8 |
| Nov. 15, 2006 | (GB) | ................... 0622825.8 |
| Mar. 19, 2007 | (GB) | ................... 0705263.2 |
| Jun. 13, 2007 | (GB) | ................... 0711439.0 |

(51) Int. Cl.
*A61K 31/4015* (2006.01)
*C07D 207/04* (2006.01)

(52) U.S. Cl. .................. 514/423; 548/530; 548/537; 514/408; 514/424

(58) Field of Classification Search ................. 548/530, 548/537; 514/408, 423, 424
See application file for complete search history.

(56) References Cited

U.S. PATENT DOCUMENTS

| 2,651,639 A | 9/1953 | Angier |
| 4,772,601 A | 9/1988 | Martin |
| 4,933,354 A | 6/1990 | Ikeguchi et al. |
| 6,054,579 A | 4/2000 | Harriman |

FOREIGN PATENT DOCUMENTS

| CN | 1385409 A | 12/2002 |
| CN | 1385409(A) | 12/2002 |
| EP | 0 314 275 A2 | 5/1989 |
| EP | 0 325 984 A2 | 8/1989 |
| FR | 2273533 A | 1/1976 |
| FR | 2273533 A1 | 1/1976 |
| WO | WO 97/17958 A1 | 5/1997 |
| WO | WO 99/00362 A1 | 1/1999 |
| WO | 9929661 A1 | 6/1999 |
| WO | 9929686 A1 | 6/1999 |
| WO | WO 00/33788 A2 | 6/2000 |
| WO | WO 05/27882 A1 | 3/2005 |
| WO | WO 08/003697 A1 | 1/2008 |

OTHER PUBLICATIONS

Angier et al.; "Some N-Substituted-5-oxo-2-pyrrolidinecarboxamides"; Journal of Organic Chemistry; 1956; vol. 21, No. 12; pp. 1540-1543.
Zhao et al., *Bioorganic & Medicinal Chemistry*, 7(8), pp. 1647-1654 (1999).
Møss et al., *International Journal of Pharmaceutics*, 52(3), pp. 255-263 (1989).
Tye et al., *Organic & Biomolecular Chemistry*, vol. 2, pp. 813-815 (2004).
Harriman, *Tetrahedron Letters*, 38(32), pp. 5591-5594 (1997).
Bundgaard et al., *Biochemical Society Transactions*, 17(5), pp. 947-949 (1989).
Bundgaard et al., *Journal of Pharmaceutical Sciences*, 78(2), pp. 122-126 (1989).
Møss et al., *Acta Pharmaceutica Nordica*, 4(4), pp. 301-308 (1992).
International Search Report for corresponding application PCT/EP2007/056675 (published as WO 08/00369A1).
Pharmaprojects Review (Jan. 2009) http://www.pharmaprojects.com/therapy_analysis/purin_P2X7_0109.htm.
Chemcats listing of CAS # 1001389-19-0 available from ChemDiv, Inc., San Diego, CA (Jul. 1, 2008).

*Primary Examiner*—Golam M M Shameem
(74) *Attorney, Agent, or Firm*—Duke M. Fitch; Kathryn L. Sieburth; Lorraine B. Ling

(57) ABSTRACT

The present invention relates to novel oxo-prolinamide derivatives of formula (I) which modulate P2X7 receptor function and are capable of antagonizing the effects of ATP at the P2X7 receptor

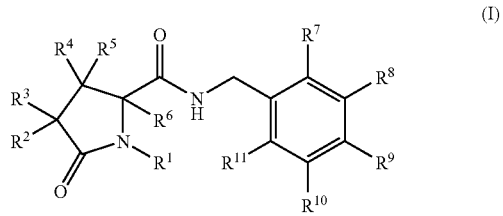

(I)

and the use of such compounds or pharmaceutical compositions thereof in the treatment of disorders mediated by the P2X7 receptor, for example pain, inflammation and neurodegeneration.

15 Claims, No Drawings

RECEPTOR ANTAGONISTS AND THEIR METHODS OF USE

CROSS-REFERENCE TO RELATED APPLICATIONS

This application claims the benefit of GB Application No. 0613473.8, filed Jul. 6, 2006; GB Application No. 0622825.8, filed Nov. 15, 2006; GB Application No. 0705263.2, filed Mar. 19, 2007; and GB Application No. 0711439.0, filed Jun. 13, 2007, each incorporated herein by reference in their entirety.

FIELD OF THE INVENTION

The present invention relates to heterocyclic amide derivatives which modulate P2X7 receptor function and are capable of antagonizing the effects of ATP at the P2X7 receptor (P2X7 receptor antagonists); to processes for their preparation; to pharmaceutical compositions containing them; and to the use of such compounds in therapy.

BACKGROUND OF THE INVENTION

The P2X7 receptor is a ligand-gated ion-channel which is expressed in cells of the hematopoietic lineage, e.g. macrophages, microglia, mast cells, and lymphocytes (T and B) (see, for example, Collo, et al. Neuropharmacology, Vol. 36, pp 1277-1283 (1997)), and is activated by extracellular nucleotides, particularly adenosine triphosphate (ATP). Activation of P2X7 receptors has been implicated in giant cell formation, degranulation, cytolytic cell death, CD62L shedding, regulation of cell proliferation, and release of proinflammatory cytokines such as interleukin 1 beta (IL-1β) (e.g. Ferrari, et al., J. Immunol., Vol. 176, pp 3877-3883 (2006)) and tumour necrosis factor alpha (TNFα) (e.g. Hide, et al. Journal of Neurochemistry, Vol. 75, pp 965-972 (2000)). P2X7 receptors are also located on antigen presenting cells, keratinocytes, parotid cells, hepatocytes, erythrocytes, erythroleukaemic cells, monocytes, fibroblasts, bone marrow cells, neurones, and renal mesangial cells. Furthermore, the P2X7 receptor is expressed by presynaptic terminals in the central and peripheral nervous systems and has been shown to mediate glutamate release in glial cells (Anderson, C. et al. Drug. Dev. Res., Vol. 50, page 92 (2000)).

The localisation of the P2X7 receptor to key cells of the immune system, coupled with its ability to release important inflammatory mediators from these cells suggests a potential role of P2X7 receptor antagonists in the treatment of a wide range of diseases including pain and neurodegenerative disorders. Recent preclinical in vivo studies have directly implicated the P2X7 receptor in both inflammatory and neuropathic pain (Dell'Antonio et al., Neurosci. Lett., Vol. 327, pp 87-90 (2002), Chessell, I P., et al., Pain, Vol. 114, pp 386-396 (2005), Honore et al., J. Pharmacol. Exp. Ther., Vol. 319, p 1376-1385 (2006)) while there is in vitro evidence that P2X7 receptors mediate microglial cell induced death of cortical neurons (Skaper, S. D., et al., Glia, Vol. 54, p 234-242 (2006)). In addition, up-regulation of the P2X7 receptor has been observed around β-amyloid plaques in a transgenic mouse model of Alzheimer's disease (Parvathenani, L. et al. J. Biol. Chem., Vol. 278(15), pp 13309-13317 (2003)).

SUMMARY OF THE INVENTION

The present invention provides compounds which modulate P2X7 receptor function and are capable of antagonizing the effects of ATP at the P2X7 receptor (P2X7 receptor antagonists). In a first aspect, a compound of formula (I), or a pharmaceutically acceptable salt thereof, is provided:

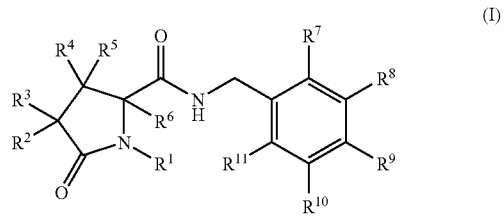

wherein:
$R^1$ represents $C_{1-6}$ alkyl, $C_{2-6}$ alkenyl, $C_{2-6}$ alkynyl, $C_{3-6}$ cycloalkyl, $C_{3-6}$ cycloalkylmethyl- or pyridinylmethyl-, any of which is optionally substituted with 1, 2 or 3 halogen atoms; or unsubstituted phenyl or benzyl;
$R^2$ and $R^3$ independently represent hydrogen, halogen, $C_{1-6}$ alkyl, arylmethyl-, $C_{2-6}$ alkenyl, $C_{2-6}$ alkynyl or $C_{3-6}$ cycloalkylmethyl-; and any of said $C_{1-6}$ alkyl, arylmethyl-, $C_{2-6}$ alkenyl, $C_{2-6}$ alkynyl or $C_{3-6}$ cycloalkylmethyl- is optionally substituted with 1, 2 or 3 halogen atoms;
$R^4$, $R^5$ and $R^6$ independently represent hydrogen, fluorine or methyl; and
$R^7$, $R^8$, $R^9$, $R^{10}$ and $R^{11}$ independently represent hydrogen, halogen, cyano, $C_{1-6}$ alkyl, $C_{2-6}$ alkenyl, $C_{2-6}$ alkynyl, $C_{3-6}$ cycloalkyl or phenyl, and any of said $C_{1-6}$ alkyl, $C_{2-6}$ alkenyl, $C_{2-6}$ alkynyl, $C_{3-6}$ cycloalkyl or phenyl is optionally substituted with 1, 2 or 3 halogen atoms;
or $R^{10}$ and $R^{11}$ together with the carbon atoms to which they are attached form a benzene ring which is optionally substituted with 1, 2 or 3 halogen atoms;
with the proviso that when $R^7$ and $R^{11}$ are both selected from hydrogen or fluorine, at least one of $R^8$, $R^9$ and $R^{10}$ is a halogen atom, or $R^8$, $R^9$ and $R^{10}$ are selected from the group consisting of hydrogen and $CF_3$ and one, but not more than one, of $R^8$, $R^9$ and $R^{10}$ is $CF_3$.

In one embodiment, a compound of formula (I), or a pharmaceutically acceptable salt thereof, is provided:

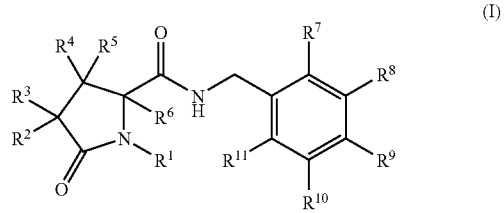

wherein:
$R^1$ represents $C_{1-6}$ alkyl, $C_{2-6}$ alkenyl, $C_{2-6}$ alkynyl, $C_{3-6}$ cycloalkyl or $C_{3-6}$ cycloalkylmethyl, any of which may be optionally substituted with 1, 2 or 3 halogen atoms; or unsubstituted phenyl or benzyl;
$R^2$ and $R^3$ independently represent hydrogen, halogen, $C_{1-6}$ alkyl, arylmethyl, $C_{2-6}$ alkenyl, $C_{2-6}$ alkynyl or $C_{3-6}$ cycloalkylmethyl; and any of said $C_{1-6}$ alkyl, arylmethyl, $C_{2-6}$ alkenyl, $C_{2-6}$ alkynyl or $C_{3-6}$ cycloalkylmethyl may be optionally substituted with 1, 2 or 3 halogen atoms;
$R^4$, $R^5$ and $R^6$ independently represent hydrogen or fluorine; and $R^7$, $R^8$, $R^9$, $R^{10}$ and $R^{11}$ independently represent hydrogen, halogen, cyano, $C_{1-6}$ alkyl, $C_{2-6}$ alkenyl, $C_{2-6}$ alkynyl, $C_{3-6}$ cycloalkyl, or phenyl; and any of said $C_{1-6}$ alkyl, $C_{2-6}$ alkenyl, $C_{2-6}$ alkynyl, $C_{3-6}$ cycloalkyl or phenyl may be optionally substituted with 1, 2 or 3 halogen atoms;

with the proviso that when $R^7$ and $R^{11}$ independently represent hydrogen or fluorine, at least one of $R^8$, $R^9$ and $R^{10}$ is a halogen atom.

In one embodiment, a compound of formula (I), or a pharmaceutically acceptable salt thereof, is provided:

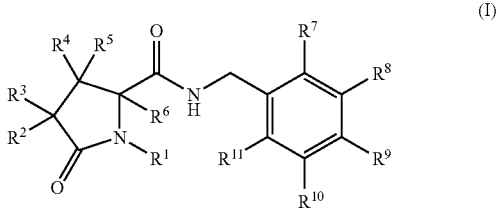

(I)

wherein:

$R^1$ represents $C_{1-6}$ alkyl, $C_{2-6}$ alkenyl, $C_{2-6}$ alkynyl, $C_{3-6}$ cycloalkyl, $C_{3-6}$ cycloalkylmethyl- or pyridinylmethyl-, any of which is optionally substituted with 1, 2 or 3 halogen atoms; or unsubstituted phenyl or benzyl;

$R^2$ and $R^3$ independently represent hydrogen, halogen, $C_{1-6}$ alkyl, arylmethyl-, $C_{2-6}$ alkenyl, $C_{2-6}$ alkynyl or $C_{3-6}$ cycloalkylmethyl-; and any of said $C_{1-6}$ alkyl, arylmethyl-, $C_{2-6}$ alkenyl, $C_{2-6}$ alkynyl or $C_{3-6}$ cycloalkylmethyl- is optionally substituted with 1, 2 or 3 halogen atoms;

$R^4$, $R^5$ and $R^6$ independently represent hydrogen, fluorine or methyl; and $R^7$, $R^8$, $R^9$, $R^{10}$ and $R^{11}$ independently represent hydrogen, halogen, cyano, $C_{1-6}$ alkyl, $C_{2-6}$ alkenyl, $C_{2-6}$ alkynyl, $C_{3-6}$ cycloalkyl or phenyl, and any of said $C_{1-6}$ alkyl, $C_{2-6}$ alkenyl, $C_{2-6}$ alkynyl, $C_{3-6}$ cycloalkyl or phenyl is optionally substituted with 1, 2 or 3 halogen atoms;

or $R^{10}$ and $R^{11}$ together with the carbon atoms to which they are attached form a benzene ring which is optionally substituted with 1, 2 or 3 halogen atoms;

with the proviso that when $R^7$ and $R^{11}$ are both selected from hydrogen or fluorine, at least one of $R^8$, $R^9$ and $R^{10}$ is a halogen atom, or not more than one of $R^8$, $R^9$ and $R^{10}$ is a $CF_3$ group.

In one embodiment, there is provided a compound of formula (I) which is

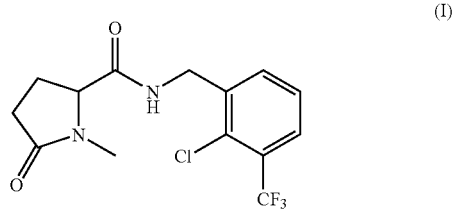

(I)

or a pharmaceutically acceptable salt or solvate thereof. Further there is provided a compound which is N-{[2-chloro-3-(trifluoromethyl)phenyl]methyl}-1-methyl-5-oxoprolinamide. And still further there is provided a compound which is N-{[2-chloro-3-(trifluoromethyl)phenyl]methyl}-1-methyl-5-oxo-L-prolinamide.

DETAILED DESCRIPTION OF THE INVENTION

As used herein, the term "alkyl" (when used as a group or as part of a group) refers to a straight or branched hydrocarbon chain containing the specified number of carbon atoms. For example, $C_{1-6}$ alkyl means a straight or branched hydrocarbon chain containing at least 1 and at most 6 carbon atoms. Examples of alkyl include, but are not limited to; methyl (Me), ethyl (Et), n-propyl, i-propyl, n-hexyl and i-hexyl.

As used herein, the term "alkenyl" refers to a straight or branched hydrocarbon chain containing the specified number of carbon atoms wherein at least one carbon-carbon bond is a double bond. Examples of alkenyl include, but are not limited to ethenyl, propenyl, n-butenyl, i-butenyl, n-pentenyl and i-pentenyl.

As used herein, the term "alkynyl" refers to a straight or branched hydrocarbon chain containing the specified number of carbon atoms wherein at least one carbon-carbon bond is a triple bond. Examples of alkynyl include, but are not limited to ethynyl, propynyl, butynyl, i-pentynyl, n-pentynyl, i-hexynyl and n-hexynyl.

The term 'cycloalkyl' unless otherwise stated means a closed 3 to 6 membered non-aromatic ring, for example cyclopropyl, cyclobutyl, cyclopentyl or cyclohexyl.

The term 'aryl' as used herein refers to a $C_{6-10}$ monocyclic or bicyclic hydrocarbon ring wherein at least one ring is aromatic. Examples of such groups include phenyl and naphthyl.

The term 'halogen' is used herein to describe, unless otherwise stated, a group selected from fluorine, chlorine, bromine or iodine.

In certain embodiments of the invention, $R^1$ represents $C_{1-6}$alkyl, $C_{2-6}$ alkenyl, $C_{2-6}$ alkynyl, $C_{3-6}$ cycloalkyl or pyridinylmethyl-, any of which is optionally substituted with 1, 2 or 3 halogen atoms; or unsubstituted phenyl or benzyl. In one embodiment, $R^1$ represents unsubstituted $C_{1-6}$ alkyl, $C_{2-6}$ alkenyl, $C_{2-6}$ alkynyl, $C_{3-6}$ cycloalkyl, pyridinylmethyl-, phenyl or benzyl. In another embodiment, $R^1$ represents unsubstituted $C_{1-4}$ alkyl, $C_{3-5}$ cycloalkyl, pyridinylmethyl-, phenyl or benzyl. In yet another embodiment, $R^1$ represents methyl or ethyl.

In certain embodiments of the invention, $R^2$ and $R^3$ independently represent hydrogen, halogen, $C_{1-6}$ alkyl, benzyl, $C_{2-6}$ alkenyl, $C_{2-6}$ alkynyl or $C_{3-6}$ cycloalkylmethyl-; and any of said $C_{1-6}$ alkyl, benzyl, $C_{2-6}$ alkenyl, $C_{2-6}$ alkynyl or $C_{3-6}$ cycloalkylmethyl- may be optionally substituted with 1, 2 or 3 halogen atoms.

In one embodiment, $R^2$ and $R^3$ independently represent hydrogen or halogen; unsubstituted $C_{1-6}$ alkyl, benzyl, $C_{2-6}$ alkenyl, $C_{2-6}$ alkynyl or $C_{3-6}$ cycloalkylmethyl-.

In another embodiment, $R^2$ and $R^3$ independently represent hydrogen, fluorine or methyl. In a further embodiment, $R^2$ and $R^3$ both represent hydrogen.

In one embodiment of the invention, $R^4$ and $R^5$ independently represent hydrogen or methyl. In another embodiment, $R^6$ represents hydrogen or methyl. In a further embodiment, $R^4$, $R^5$ and $R^6$ all represent hydrogen.

In another embodiment of the invention, $R^7$, $R^8$, $R^9$, $R^{10}$ and $R^{11}$ independently represent hydrogen, halogen, cyano, trifluoromethyl or unsubstituted $C_{1-6}$ alkyl; or $R^{10}$ and $R^{11}$ together with the carbon atoms to which they are attached form an unsubstituted benzene ring. In a further embodiment, $R^7$, $R^8$, $R^9$, $R^{10}$ and $R^{11}$ independently represent hydrogen, halogen, cyano, methyl or trifluoromethyl; or $R^{10}$ and $R^{11}$ together with the carbon atoms to which they are attached form an unsubstituted benzene ring. In yet another embodiment, $R^7$, $R^8$, $R^9$, $R^{10}$ and $R^{11}$ independently represent hydrogen, chlorine, fluorine, bromine, methyl or trifluoromethyl.

In one embodiment of the invention, there is provided a compound of formula (I), or a pharmaceutically acceptable salt thereof, wherein:

$R^1$ represents unsubstituted $C_{1-4}$alkyl, $C_{2-4}$ alkenyl, $C_{3-5}$ cycloalkyl, pyridinylmethyl-, phenyl or benzyl;

$R^2$ and $R^3$ both represent hydrogen;

$R^4$, $R^5$ and $R^6$ independently represent hydrogen or methyl; and $R^7$, $R^8$, $R^9$, $R^{10}$ and $R^{11}$ independently represent hydrogen, chlorine, fluorine, bromine, methyl or trifluoromethyl;

with the proviso that when $R^7$ and $R^{11}$ are both selected from hydrogen or fluorine, at least one of $R^8$, $R^9$ and $R^{10}$ is a halogen atom, or $R^8$, $R^9$ and $R^{10}$ are selected from the group consisting of hydrogen and $CF_3$ and one, but not more than one, of $R^8$, $R^9$ and $R^{10}$ is $CF_3$.

Particular compounds according to the invention include the compounds of Examples 1-136 as shown below, or a pharmaceutically acceptable salt thereof.

Antagonists of P2X7 may be useful in preventing, treating, or ameliorating a variety of pain states (e.g. neuropathic pain, chronic inflammatory pain, and visceral pain), inflammation and neurodegeneration, in particular Alzheimer's disease. P2X7 antagonists may also constitute useful therapeutic agents in the management of rheumatoid arthritis and inflammatory bowel disease.

Compounds of the present invention which modulate P2X7 receptor function and are capable of antagonizing the effects of ATP at the P2X7 receptor (P2X7 receptor antagonists) may be competitive antagonists, inverse agonists, negative allosteric modulators or indirect modulators of receptor function.

Certain compounds of formula (I may in some circumstances form acid addition salts thereof. It will be appreciated that for use in medicine compounds of formula (I) may be used as salts, in which case the salts should be pharmaceutically acceptable. Pharmaceutically acceptable salts include those described by Berge, Bighley and Monkhouse, J. Pharm. Sci., 1977, 66, 1-19. Basic compounds of formula (I) may form salts with pharmaceutically acceptable acids including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Examples of pharmaceutically acceptable salts include those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. In examples where the stereochemical composition of the final product has been determined by chiral HPLC (more specifically by methods (A), (B), (C) or (D) as set out in the Examples), the corresponding stereospecific name and structure have been assigned to the final product where the enantiomeric excess of said product is greater than 70%. Assignment of absolute stereochemistry is based on the known chirality of the starting material. In examples where the composition of the final product has not been characterised by chiral HPLC, the stereochemistry of the final product has not been indicated. However, the chirality of the main component of the product mixture will be expected to reflect that of the starting material and the enantiomeric excess will depend on the synthetic method used and is likely to be similar to that measured for an analogous example (where such an example exists). Thus compounds shown in one chiral form are expected to be able to be prepared in the alternative chiral form using the appropriate starting material. Alternatively, if racemic starting materials are used, it would be expected that a racemic product would be produced and the single enantiomers could be separated by the usual methods. The invention also extends to any tautomeric forms and mixtures thereof.

The subject invention also includes isotopically-labeled compounds, which are identical to those recited in formula (I) and following, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, phosphorous, fluorine, iodine, and chlorine, such as 3H, 11C, 14C, 18F, 123I and 125I.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 8F isotopes are particularly useful in PET (positron emission tomography), and 125I isotopes are particularly useful in SPECT (single photon emission computerized tomography). PET and SPECT are useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labeled compounds of formula (I) and following of this invention can generally be prepared by carrying out the procedures disclosed in the Schemes and/or in the Examples below, by substituting a readily available isotopically labeled reagent for a non-isotopically labeled reagent.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications are well known to those skilled in the art.

Preparation of Compounds

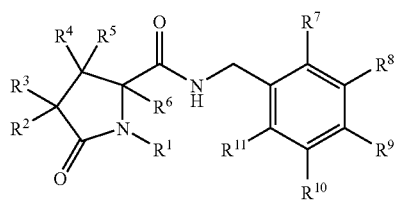

Compounds of formula (I), wherein the variables are as defined above, and salts and solvates thereof may be prepared by the methodology described hereinafter, constituting a further aspect of this invention.

A process according to the invention for preparing a compound of formula (I) which comprises:
(a) Coupling of a carboxylic acid of formula (2) (or an activated derivative thereof) with an amine of formula (3) (see Scheme 1), wherein $R^1$, $R^2$, $R^3$, $R^4$, $R^5$, $R^6$, $R^7$, $R^8$, $R^9$, $R^{10}$ and $R^{11}$ are as defined above. Compounds (2) and (3) are optionally protected;
(b) The reaction of a dicarbonyl compound of formula (4), an isocyanide of formula (5) and an amine of formula (6) in a suitable solvent such as methanol and at a suitable temperature such as 100° C. (see Scheme 2), wherein $R^1$, $R^2$, $R^3$, $R^4$, $R^5$, $R^7$, $R^8$, $R^9$, $R^{10}$ and $R^{11}$ are as defined above and $R^5$=H or methyl. Compounds (4), (5) and (6) are optionally protected. Processes of this type have been described previously in the chemical literature (e.g. H. Tye, and M. Whittaker, *Org. Biomol. Chem.*, 2004, 2, 813-815; G. C. B. Harriman WO 9900362 A1);
(c) Deprotecting a compound of formula (I) which is protected. Examples of protecting groups and the means for their removal can be found in T. W. Greene and P. G. M. Wuts 'Protective Groups in Organic Synthesis' (J. Wiley and Sons, 3$^{rd}$ Ed. 1999); or
(d) Interconversion of compounds of formula (I) to other compounds of formula (I). Examples of conventional interconversion procedures include epimerisation, oxidation, reduction, alkylation, aromatic substitution, nucleophilic substitution, amide coupling and ester hydrolysis.

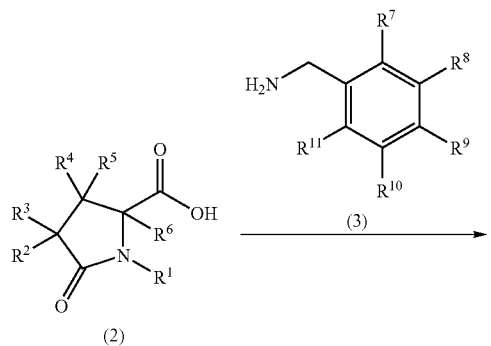

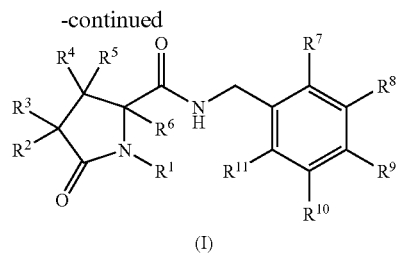

The coupling of an acid of formula (2) and an amine of formula (3) typically comprises the use of activating agents, such as N-(3-dimethylaminopropyl)-N'-ethylcarbodiimide hydrochloride or polymer-supported carbodiimide, 1-hydroxybenzotriazole (HOBT) or 1-hydroxy-7-azabenzotriazole (HOAt), and optionally a suitable base such as a tertiary alkylamine (e.g. diisopropylethylamine, N-ethyl morpholine, triethylamine) or pyridine, in a suitable solvent such as DMF and/or dichloromethane and at a suitable temperature e.g. between 0° C. and room temperature. Alternatively the coupling of (2) and (3) may be accomplished by treatment with O-(7-azabenzotriazol-1-yl)-N,N,N',N'-tetramethyluronium hexafluorophosphate and a suitable tertiary alkylamine such as diisopropylethylamine in a suitable solvent such as dimethylformamide at a suitable temperature such as room temperature. Alternatively, the compound of formula (2) may be employed as an activated derivative (e.g. acid chloride, mixed anhydride, active ester (e.g. O-acyl-isourea)), and under such circumstances process (a) typically comprises treatment of said activated derivative with an amine (Ogliaruso, M. A.; Wolfe, J. F. in *The Chemistry of Functional Groups* (Ed. Patai, S.) *Suppl. B: The Chemistry of Acid Derivatives, Pt. 1* (John Wiley and Sons, 1979), pp 442-8; Beckwith, A. L. J. in *The Chemistry of Functional Groups* (Ed. Patai, S.) *Suppl. B: The Chemistry of Amides* (Ed. Zabricky, J.) (John Wiley and Sons, 1970), pp 73 ff).

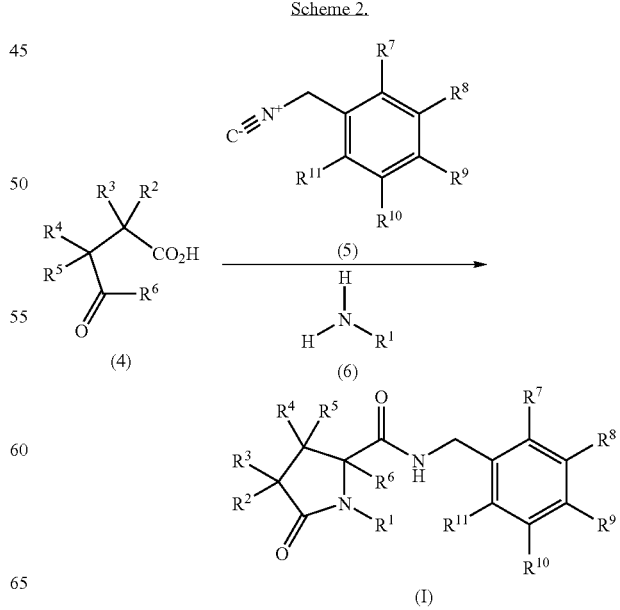

Representative methods for the preparation of compounds of formula (2) are shown in Schemes 3-9 below:

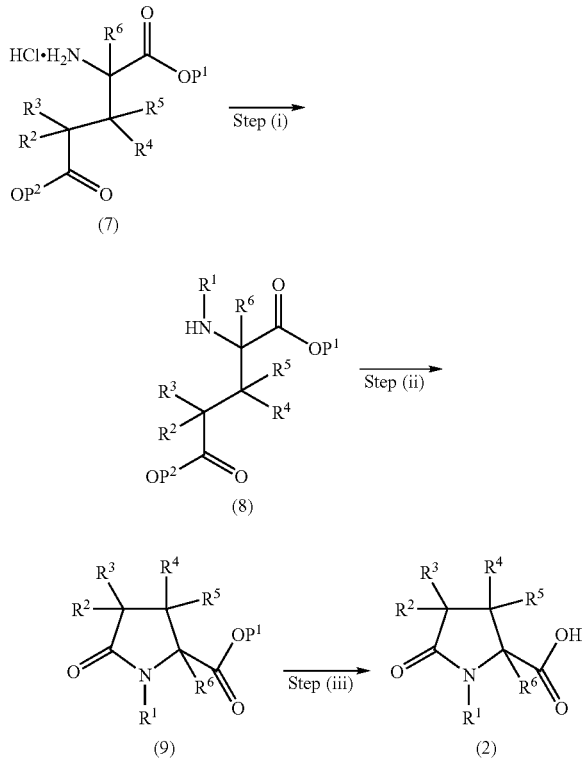

wherein $R^1$, $R^2$, $R^3$, $R^4$ and $R^5$ are as defined above, $R^6$=H or F, and $P^1$ and $P^2$ represent suitable protecting groups such as $C_{1-6}$alkyl or $P^1$ and $P^2$=H.

Analogous processes to those described below for the transformations outlined in scheme 3 have been described previously in the chemical literature (e.g. G. Verardo, P. Geatti, E. Pol, and A. G. Giumanini, *Can. J. Chem.*, 80: 779-788 (2002); T. Godet, et al., *Organic Letters*, (2004), 6(19), 3281-3284)

Step (i) typically comprises initial treatment of (7) with a base such as sodium hydroxide in a suitable solvent such as methanol at a suitable temperature such as 0° C. followed by reductive alkylation which typically comprises subsequent treatment with an aldehyde or ketone and an acid, such as acetic acid, and then addition of a reducing agent such as sodium borohydride at a suitable temperature such as between 0° C. and room temperature.

Step (ii) may occur spontaneously, in which case (9) is isolated directly from the reaction of (7) as described in step (i) above, but more typically compound (8) is heated at a suitable temperature, such as 110° C., in a suitable solvent, such as toluene, to afford compound (9).

Deprotection step (iii) typically comprises a standard procedure for conversion of a carboxylic ester to an acid, such as use of an appropriate hydroxide salt (e.g. sodium hydroxide) in an appropriate solvent such as methanol at a suitable temperature such as between 0° C. and room temperature.

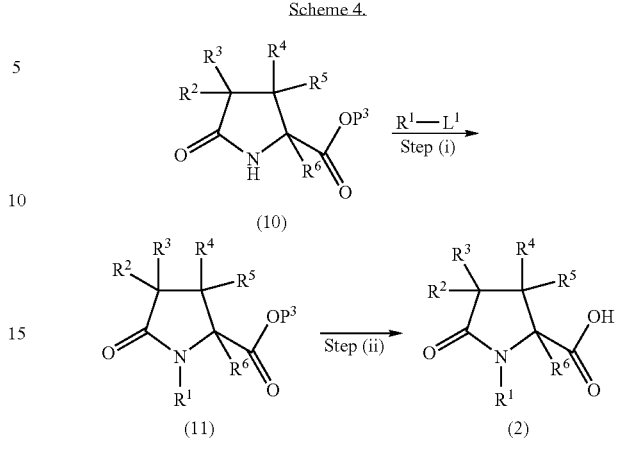

wherein $R^1$, $R^2$, $R^3$, $R^4$ and $R^5$ are as defined above, $R^6$=H or F, $L^1$ is a suitable group such as halogen (e.g. chlorine or bromine) or a boronic acid or boronic ester and $P^3$ represents a suitable protecting groups such as $C_{1-6}$alkyl.

Analogous processes to those described below for the transformations outlined in scheme 4 have been described previously in the chemical literature (e.g. T. Itoh, et al., *Tetrahedron.*, 59 (2003), 3527-3536; T. Simandan and M. B. Smith, *Synthetic Communications*, 26(9), 1827-1838 (1996)).

Step (i) typically comprises treatment of (10) with a base such as sodium hydride and an alkylating agent such as an alkyl halide in a suitable solvent such as tetrahydrofuran at a suitable temperature such as between 0° C. and room temperature or alternatively it may comprise treatment of (10) with an aryl halide or aryl or alkenyl boronic acid (or ester) in a suitable solvent such as toluene in the presence of a suitable catalyst such as a mixture of tris(dibenzylideneacetone)dipalladium(0) and Xantphos™ (9,9-dimethyl-4,5-bis(diphenylphosphino)xanthene) and a suitable base such as cesium carbonate at a suitable temperature such as 120° C.

Deprotection (ii) typically comprises a standard procedure for conversion of a carboxylic ester to an acid, such as use of an appropriate hydroxide salt (e.g. sodium hydroxide) in an appropriate solvent such as methanol at a suitable temperature such as between 0° C. and room temperature; or use of an appropriate acid (e.g. trifluoroacetic acid) in an appropriate solvent such as dichloromethane at a suitable temperature such as between 0° C. and room temperature.

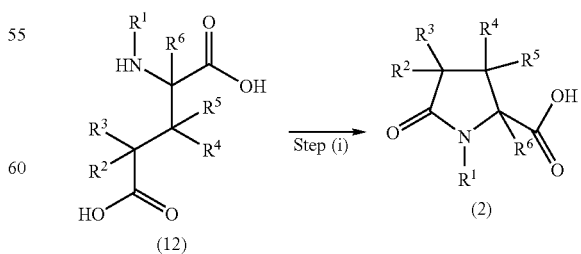

wherein $R^1$, $R^2$, $R^3$, $R^4$ and $R^5$ are as defined above and $R^6$=H or F.

Analogous processes to those described below for the transformation outlined in scheme 5 have been described previously in the chemical literature (e.g. S. Aoki, et al., *Tetrahedron*, 60 (2004) 7053-7059)

Step (i) typically comprises heating (12) in an autoclave or sealed tube in a suitable solvent, such as water, and at a suitable temperature such as from 100-140° C. with or without microwave irradiation.

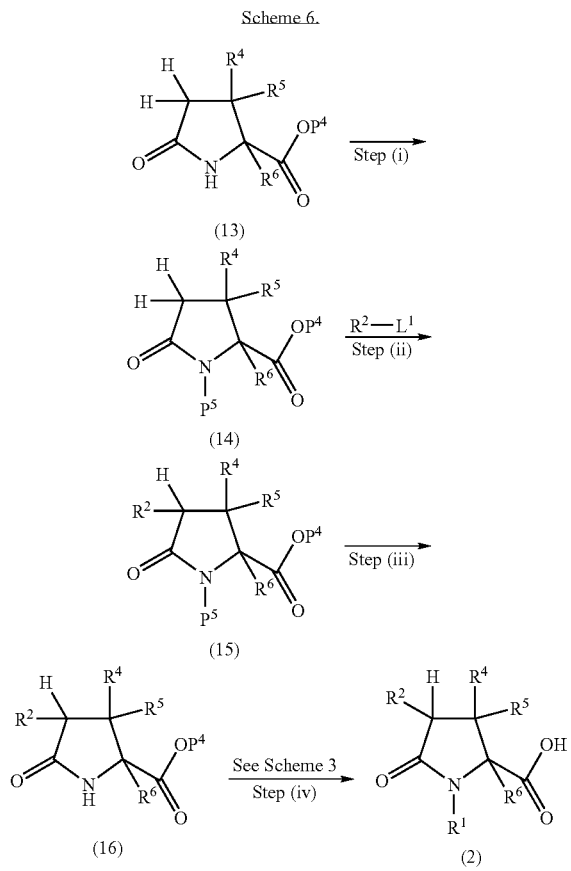

Step (iii) typically comprises deprotection of (15) by standard protocols such as, for the case when $P^5$ is a tertbutoxy carbonyl group, treatment with hydrogen chloride in a suitable solvent such as dioxane and at a suitable temperature such as room temperature.

Step (iv) typically comprises the process described above for the steps shown in Scheme 4.

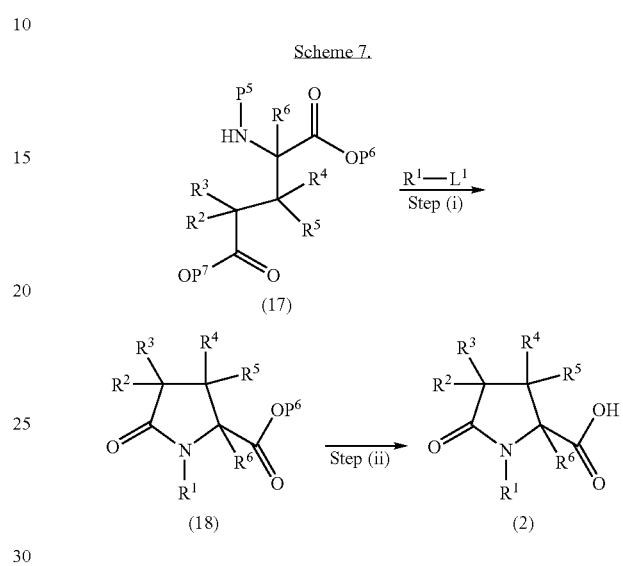

wherein $R^1$, $R^2$, $R^3$, $R^4$ and $R^5$ are as defined above and $R^6$=H or F. $P^5$, $P^6$ and $P^7$ represent suitable protecting groups, for example $P^5$ can be a $C_{1-6}$ alkoxycarbonyl and $P^6$ and $P^7$ can be $C_{1-6}$ alkyl ($P^6$ and $P^7$ need not be the same). $L^1$ is a suitable leaving group such as halogen (e.g. chlorine or bromine).

Step (i) typically comprises treatment of (17) with a suitable base, such as potassium hexamethyldisilazide, and an alkylating agent such as an alkyl halide in a suitable solvent such as tetrahydrofuran at a suitable temperature such as between −78° C. and room temperature.

Step (ii) typically comprises a standard procedure for conversion of a carboxylic ester to an acid, such as treatment with a suitable acid (e.g. trifluoroacetic acid) in an appropriate solvent such as dichloromethane at a suitable temperature such as room temperature.

wherein $R^1$, $R^4$ and $R^5$ are as defined above, $R^2$ represents a group as defined above other than hydrogen or halogen, $R^6$=H or F, $L^1$ is a suitable leaving group such as halogen (e.g. chlorine or bromine), and $P^4$ and $P^5$ represent suitable protecting groups such as $C_{1-6}$alkyl and $C_{1-6}$alkoxycarbonyl respectively.

Analogous processes to those described below for the transformations outlined in scheme 6 have been described previously in the chemical literature (e.g. A. Bassoli, et al., *Eur. J. Org. Chem.*, 2005, 2518-2525).

Step (i) typically comprises protection of (13) by standard protocols such as treatment with an alkoxycarbonyl anhydride, such as di-tertbutyl dicarbonate, and a base such as triethylamine and a catalyst such as 4-dimethylaminopyridine in a suitable solvent such as dichloromethane at a suitable temperature such as room temperature.

Step (ii) typically comprises treatment of (14) with a base such as lithium bis(trimethylsilyl)amide and an alkylating agent such as an alkyl halide in a suitable solvent such as tetrahydrofuran at a suitable temperature such as between −78° C. and room temperature.

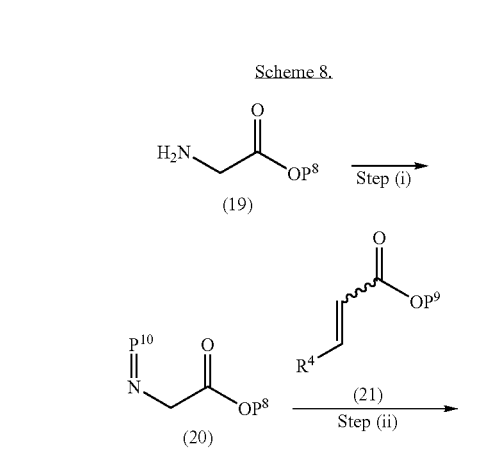

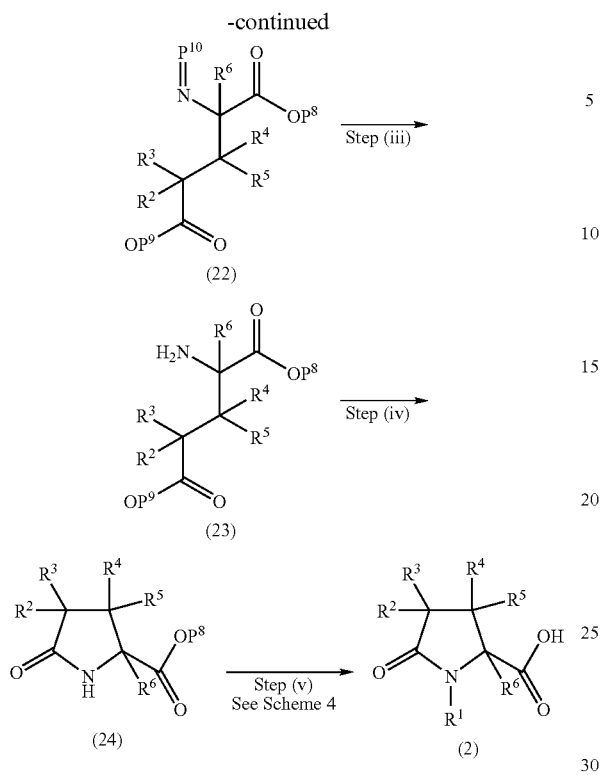

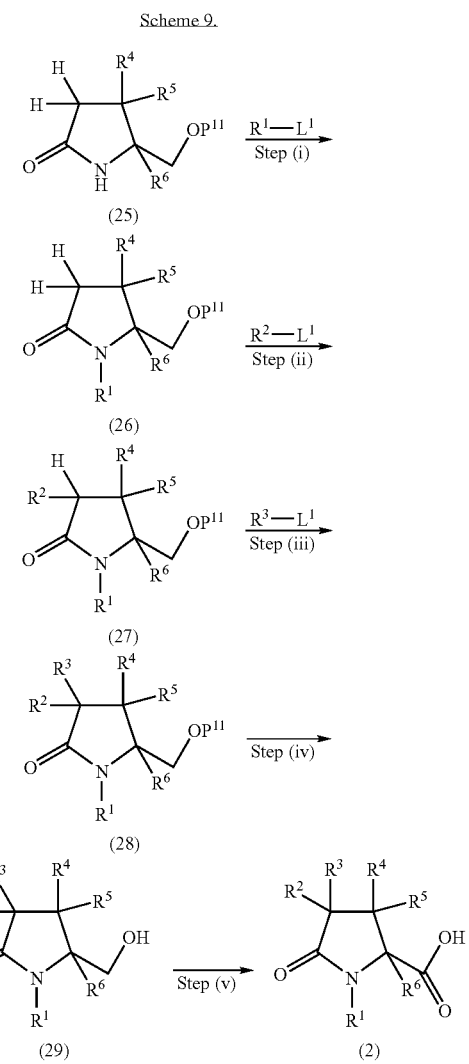

Scheme 9.

wherein $R^1$, $R^2$, $R^3$, $R^4$ and $R^5$ are as defined above and $R^6$=H or F. $P^8$, $P^9$ and $P^{10}$ represent suitable protecting groups such as $C_{1-6}$ alkyl in the cases of $P^8$ and $P^9$ ($P^8$ and $P^9$ need not be the same) and a group derived from a suitable acyclic or cyclic ketone in the case of $P^{10}$.

Analogous processes to those described below for the transformations outlined in steps (i)-(iii) of scheme 8 have been described previously in the chemical literature (e.g. J. Wehbe, et. al., Tetrahedron: *Asymmetry.*, 14 (2003), 1123-1126).

Step (i) typically comprises treatment of (19) with a suitable ketone, such as (1R,2R,5R)-2-hydroxypinan-3-one, and a lewis acid such as boron trifluoride etherate in a suitable solvent such as toluene at a suitable temperature such as 110° C.

Step (ii) typically comprises treatment of (20) with a Grignard reagent, such as methyl magnesium bromide, and a base, such as 1,8-diazabicyclo[5.4.0]undec-7-ene, followed by treatment with an unsaturated ester (21), such as ethyl crotonate in a suitable solvent such as tetrahydrofuran at a suitable temperature such as –30° C.

Step (iii) typically comprises a standard procedure for conversion of an imine to an amine, such as treatment with a suitable acid (e.g. 15% aqueous citric acid) in an appropriate solvent such as tetrahydrofuran at a suitable temperature such as room temperature.

Step (iv) typically comprises heating (23) in a suitable solvent, such as toluene, at a suitable temperature such as between room temperature and 120° C.

Step (v) typically comprises the process described above for the steps shown in Scheme 4.

wherein $R^1$, $R^4$, $R^5$ and $R^6$ are as defined above, $R^2$ and $R^3$ each represent a group as defined above other than halogen, $L^1$ and $L^2$ are suitable leaving groups such as halogen (e.g. chlorine or bromine), and $P^{11}$ represents a suitable protecting group such as trityl.

Step (i) typically comprises treatment of (25) with a base such as sodium hydride and an alkylating agent such as an alkyl halide in a suitable solvent such as dimethylformamide at a suitable temperature such as between 0° C. and room temperature.

Step (ii) typically comprises treatment of (26) with a base such as lithium diisopropylamide and an alkylating agent such as an alkyl halide in a suitable solvent such as tetrahydrofuran at a suitable temperature such as between –78° C. and room temperature.

Step (iii) typically comprises treatment of (27) with a base such as lithium diisopropylamide and an alkylating agent such as an alkyl halide in a suitable solvent such as tetrahydrofuran at a suitable temperature such as between –78° C. and room temperature.

Step (iv) typically comprises a standard procedure for deprotecting an alcohol. For example, when $P^{11}$ is a trityl group, treatment of (28) with a suitable acid such as Amberlyst 15® in a suitable solvent such as methanol and at a suitable temperature such as room temperature.

Step (v) typically comprises a standard protocol for oxidation of an alcohol to the corresponding carboxylic acid such as treatment of the alcohol (29) with an oxidising agent such as a combination of sodium chlorite, TEMPO (2,2,6,6-tetramethyl-1-piperidinyloxy free radical) and bleach (sodium hypochlorite solution) in a suitable solvent such as a mixture of aqueous sodium phosphate monobasic buffer solution and acetonitrile at a suitable temperature such as 40° C.

Step (ii) or step (iii) can be omitted as required to prepare compounds where $R^2$=H or $R^3$=H respectively.

Compounds of the general formulae (3), (4), (5), (6), (7), (10), (12), (13), (17), (19), (21) and (25) are typically either available from commercial sources or can be prepared by a person skilled in the art using methods described in the chemical literature (or using analogous methods).

Where relevant, pharmaceutically acceptable salts may be prepared conventionally by reaction with the appropriate acid or acid derivative.

Clinical Indications

It is believed that as compounds of the present invention modulate P2X7 receptor function and are capable of antagonizing the effects of ATP at the P2X7 receptor they may be useful in the treatment of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

Chronic articular pain conditions include rheumatoid arthritis, osteoarthritis, rheumatoid spondylitis, gouty arthritis and juvenile arthritis.

Pain associated with functional bowel disorders includes non-ulcer dyspepsia, non-cardiac chest pain and irritable bowel syndrome.

Neuropathic pain syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Other conditions which could potentially be treated by compounds of the present invention include fever, inflammation, immunological diseases, abnormal platelet function diseases (e.g. occlusive vascular diseases), impotence or erectile dysfunction; bone disease characterised by abnormal bone metabolism or resorbtion; hemodynamic side effects of non-steroidal anti-inflammatory drugs (NSAID's) and cyclooxygenase-2 (COX-2) inhibitors, cardiovascular diseases; neurodegenerative diseases and neurodegeneration, neurodegeneration following trauma, tinnitus, dependence on a dependence-inducing agent such as opiods (e.g. morphine), CNS depressants (e.g. ethanol), psychostimulants (e.g. cocaine) and nicotine; complications of Type I diabetes, kidney dysfunction, liver dysfunction (e.g. hepatitis, cirrhosis), gastrointestinal dysfunction (e.g. diarrhoea), colon cancer, overactive bladder and urge incontinence. Depression and alcoholism could potentially also be treated by compounds of the present invention.

Inflammation and the inflammatory conditions associated with said inflammation include skin conditions (e.g. sunburn, burns, eczema, dermatitis, allergic dermatitis, psoriasis), meningitis, ophthalmic diseases such as glaucoma, retinitis, retinopathies, uveitis and of acute injury to the eye tissue (e.g. conjunctivitis), inflammatory lung disorders (e.g. asthma, bronchitis, emphysema, allergic rhinitis, respiratory distress syndrome, pigeon fancier's disease, farmer's lung, chronic obstructive pulmonary disease (COPD), airways hyperresponsiveness); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation and other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, gingivitis, myocardial ischemia, pyrexia, systemic lupus erythematosus, polymyositis, tendinitis, bursitis, and Sjogren's syndrome.

Immunological diseases include autoimmune diseases, immunological deficiency diseases or organ transplantation.

Bone diseases characterised by abnormal bone metabolism or resorbtion include osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis.

Cardiovascular diseases include hypertension or myocardiac ischemia; atherosclerosis; functional or organic venous insufficiency; varicose therapy; haemorrhoids; and shock states associated with a marked drop in arterial pressure (e.g. septic shock).

Neurodegenerative diseases include dementia, particularly degenerative dementia (including senile dementia, dementia with Lewy bodies, Alzheimer's disease, Pick's disease, Huntingdon's chorea, Parkinson's disease and Creutzfeldt-Jakob disease, Amyotrophic Lateral Sclerosis (ALS) and motor neuron disease); vascular dementia (including multi-infarct dementia); as well as dementia associated with intracranial space occupying lesions; trauma; infections and related conditions (including HIV infection, meningitis and shingles); metabolism; toxins; anoxia and vitamin deficiency; and mild cognitive impairment associated with ageing, particularly Age Associated Memory Impairment.

The compounds of formula (I) may also be useful for neuroprotection and in the treatment of neurodegeneration following trauma such as stroke, cardiac arrest, pulmonary bypass, traumatic brain injury, spinal cord injury or the like.

The compounds of the present invention may also be useful in the treatment of malignant cell growth and/or metastasis, and myoblastic leukaemia.

Complications of Type 1 diabetes include diabetic microangiopathy, diabetic retinopathy, diabetic nephropathy, macular degeneration, glaucoma, nephrotic syndrome, aplastic anaemia, uveitis, Kawasaki disease and sarcoidosis.

Kidney dysfunction includes nephritis, glomerulonephritis, particularly mesangial proliferative glomerulonephritis and nephritic syndrome.

It is to be understood that reference to treatment includes both treatment of established symptoms and prophylactic treatment, unless explicitly stated otherwise.

According to a further aspect of the invention, we therefore provide a compound of formula (I) or a pharmaceutically acceptable salt thereof for use in human or veterinary medicine.

According to another aspect of the invention, we provide a compound of formula (I) or a pharmaceutically acceptable salt thereof for use in the treatment of a condition which is mediated by P2X7 receptors.

According to a further aspect of the invention, we provide a method of treating a human or animal subject suffering from a condition which is mediated by P2X7 receptors which comprises administering to said subject an effective amount of a compound of formula (I) or a pharmaceutically acceptable salt thereof.

According to a further aspect of the invention we provide a method of treating a human or animal subject suffering from pain, inflammation or a neurodegenerative disease, which method comprises administering to said subject an effective amount of a compound of formula (I) or a pharmaceutically acceptable salt thereof.

According to a yet further aspect of the invention we provide a method of treating a human or animal subject suffering from inflammatory pain, neuropathic pain or visceral pain which method comprises administering to said subject an effective amount of a compound of formula (I) or a pharmaceutically acceptable salt thereof.

According to a further aspect of the invention we provide a method of treating a subject, for example a human subject, suffering from Alzheimer's disease which method comprises administering to said subject an effective amount of a compound of formula (I) or a pharmaceutically acceptable salt thereof.

According to another aspect of the invention, we provide the use of a compound of formula (I) or a pharmaceutically acceptable salt thereof for the manufacture of a medicament for the treatment of a condition which is mediated by the action of P2X7 receptors.

According to another aspect of the invention we provide the use of a compound of formula (I) or a pharmaceutically acceptable salt thereof for the manufacture of a medicament for the treatment or prevention of pain, inflammation or a neurodegenerative disease.

According to another aspect of the invention we provide the use of a compound of formula (I) or a pharmaceutically acceptable salt thereof for the manufacture of a medicament for the treatment or prevention of inflammatory pain, neuropathic pain or visceral pain.

In one aspect of the invention we provide the use of a compound of formula (I) or a pharmaceutically acceptable salt thereof for the manufacture of a medicament for the treatment or prevention of Alzheimer's disease.

In order to use a compound of formula (I) or a pharmaceutically acceptable salt thereof for the treatment of humans and other mammals it is normally formulated in accordance with standard pharmaceutical practice as a pharmaceutical composition. Therefore in another aspect of the invention there is provided a pharmaceutical composition comprising a compound of formula (I), or a pharmaceutically acceptable salt thereof, adapted for use in human or veterinary medicine.

In order to use the compounds of formula (I) in therapy, they will normally be formulated into a pharmaceutical composition in accordance with standard pharmaceutical practice. The present invention also provides a pharmaceutical composition, which comprises a compound of formula (I), or a pharmaceutically acceptable salt thereof, and optionally a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 200 mg, for example 20 to 40 mg; and such unit doses will preferably be administered once a day, although administration more than once a day may be required; and such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention but are not intended to be limiting.

EXAMPLES

The general methods (a)-(d), along with the synthetic methods outlined in Schemes 1-9 above, for the preparation of compounds of the present invention are further illustrated by the following examples.

Example 1

N-[(2-chloro-4-fluorophenyl)methyl]-5-oxo-1-(phenylmethyl)-prolinamide (E1)

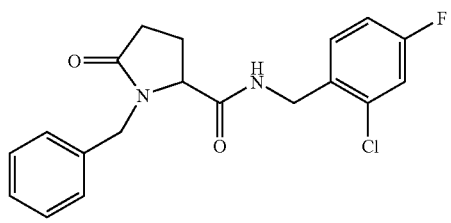

5-Oxo-1-(phenylmethyl)-proline (0.176 g, 0.80 mmol, prepared as described below) was dissolved in dichloromethane (3 ml) and to this was added 1-hydroxybenzotriazole (0.119 g, 0.88 mmol), triethylamine (0.113 ml, 0.81 mmol), [(2-chloro-4-fluorophenyl)methyl]amine (0.134 g, 0.84 mmol) and N-(3-dimethylaminopropyl)-N'-ethylcarbodiimide hydrochloride (0.169 g, 0.88 mmol) under an atmosphere of argon. The mixture was stirred at room temperature overnight. The mixture was diluted with dichloromethane and washed sequentially with 2M aqueous hydrogen chloride and saturated aqueous sodium hydrogen carbonate. The organic layer was filtered through a phase separator and then evaporated to give the crude product. The crude material was purified by mass-directed automated HPLC to give pure N-[(2-chloro-4-fluorophenyl)methyl]-5-oxo-1-(phenylmethyl)-prolinamide (0.112 g) as a white solid.

LC/MS [M+H]$^+$=361.2, retention time=2.55 minutes.

The 5-oxo-1-(phenylmethyl)-proline used in the above procedure was prepared as follows:

(i) Dimethyl L-glutamate hydrochloride (0.500 g, 2.37 mmol) was dissolved in methanol (10 ml) and cooled to 0° C. The mixture was then treated with sodium hydroxide (0.099 g, 2.49 mmol) followed by acetic acid (0.136 ml, 2.37 mmol) and benzaldehyde (0.361 ml, 3.55 mmol). After stirring for 10 minutes at 0° C., sodium borohydride (0.088 g, 2.37 mmol) was added and the mixture was left to warm to room temperature and stirred overnight. The mixture was again cooled to 0° C. and treated with a further quantity of sodium borohydride (0.044 g, 1.18 mmol). The mixture was again left to warm to room temperature and stirred overnight. Evaporation of the methanol gave a residue which was taken up in ethyl acetate and filtered. The filtrate was then washed with saturated aqueous sodium hydrogen carbonate, filtered through a phase separator (with stirring) and evaporated to give a clear oil (0.56 g). The oil was dissolved in methanol and heated in a sealed tube in a microwave reactor at 120° C. for 10 minutes and then for 15 minutes at 140° C. (LC/MS indicated that this heating phase had not altered the composition of the mixture significantly). The solvent was evaporated and the residue purified by flash-silica column chromatography, eluting with a 15-20% gradient of ethyl acetate in hexane, to give pure methyl 5-oxo-1-(phenylmethyl)-prolinate (0.212 g) as a clear oil.

LC/MS [M+H]$^+$=234, retention time=2.15 minutes.

(ii) Methyl 5-oxo-1-(phenylmethyl)-prolinate (0.212 g, 0.91 mmol) was dissolved in water (3 ml) and methanol (0.5 ml) and treated with 2M aqueous sodium hydroxide (0.682 ml, 1.36 mmol). The mixture was stirred overnight at room temperature and then washed with dichloromethane. The aqueous layer was evaporated and the residue treated with an excess of 1M hydrogen chloride in ether (~5 ml). The mixture was evaporated once more and the residue was triturated with dichloromethane. The solid material was discarded and the combined dichloromethane fractions were evaporated to give 5-oxo-1-(phenylmethyl)-proline (0.182 g) as a yellow oil which was used without further purification.

LC/MS [M+H]$^+$=220, retention time=1.72 minutes.

Example 2

N-[(2-chloro-4-fluorophenyl)methyl]-1-(1-methylethyl)-5-oxo-prolinamide (E2)

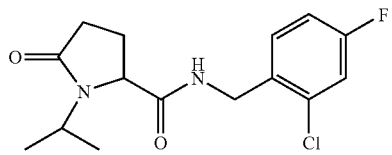

1-(1-Methylethyl)-5-oxo-proline (0.060 g, 0.35 mmol, prepared as described below) was dissolved in dichloromethane (3 ml) and dimethylformamide (1 ml) and to this was added 1-hydroxybenzotriazole (0.052 g, 0.39 mmol), [(2-chloro-4-fluorophenyl)methyl]amine (0.061 g, 0.39 mmol) and N-(3-dimethylaminopropyl)-N'-ethylcarbodiimide hydrochloride (0.074 g, 0.39 mmol) under an atmosphere of argon. The mixture was stirred at room temperature overnight. The mixture was diluted with dichloromethane and washed sequentially with 2M aqueous hydrogen chloride and saturated aqueous sodium hydrogen carbonate. The organic layer was filtered through a phase separator and then evaporated to give the crude product. The crude material was purified by mass-directed automated HPLC to give pure N-[(2-chloro-4-fluorophenyl)methyl]-1-(1-methylethyl)-5-oxo-prolinamide (0.032 g) as a white solid. LC/MS [M+H]$^+$=313.1, retention time=2.26 minutes.

The 1-(1-methylethyl)-5-oxo-proline used in the above procedure was prepared as follows:

(i) Dimethyl L-glutamate hydrochloride (0.500 g, 2.37 mmol) was dissolved in methanol (4 ml) and tetrahydrofuran (8 ml) and the mixture was then treated with crushed sodium hydroxide (0.099 g, 2.49 mmol) for 10 minutes. At this stage acetic acid (0.136 ml, 2.37 mmol) and acetone (0.261 ml, 3.55 mmol) were added together to the mixture as a solution in tetrahydrofuran (1 ml). After stirring for 10 minutes the mixture was cooled to 0° C. and treated with sodium borohydride pellets (0.088 g, 2.37 mmol). The mixture was then left to warm to room temperature and stirred overnight. Evaporation of the methanol gave a residue which was taken up in ethyl acetate and filtered. The filtrate was then washed with saturated aqueous sodium hydrogen carbonate, filtered through a phase separator (with stirring) and evaporated to give a clear oil (0.217 g). The oil was purified by flash-silica column chromatography to give pure dimethyl N-(1-methylethyl) glutamate (0.200 g).

(ii) Dimethyl N-(1-methylethyl)-glutamate (0.200 g) was dissolved in methanol and heated in a sealed tube in a microwave reactor at 140° C. for 20 minutes. Thin-layer chromatography indicated that the starting material remained intact so the solvent was evaporated and replaced with toluene. The mixture was heated at reflux temperature for ~3 hrs and then evaporated to give methyl 1-(1-methylethyl)-5-oxo-prolinate (0.152 g) as a light yellow oil which was used in the subsequent step without further purification.

(iii) Methyl 1-(1-methylethyl)-5-oxo-prolinate (0.152 g, 0.82 mmol) was dissolved in water (3 ml) and methanol (0.5 ml) and treated with 2M aqueous sodium hydroxide (0.682 ml, 1.36 mmol). The mixture was stirred for ~4 hrs at room temperature and then washed with dichloromethane. The aqueous layer was evaporated and the residue treated with an excess of 1M hydrogen chloride in ether (~5 ml). The mixture was evaporated once more and the residue was triturated with dichloromethane. The solid material was discarded and the combined dichloromethane fractions were evaporated to give 1-(1-methylethyl)-5-oxo-proline (0.060 g) as a yellow oil which crystallized on standing.

Example 3

N-[(2-chloro-4-fluorophenyl)methyl]-1-ethyl-5-oxo-prolinamide (E3)

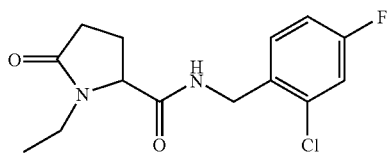

Methyl 1-ethyl-5-oxo-prolinate (0.135 g, 0.79 mmol, prepared as described below) was dissolved in methanol (4 ml) and treated with 2M aqueous sodium hydroxide (0.592 ml, 1.18 mmol). The mixture was stirred for 4 hrs at room temperature and then evaporated to give a residue which was then treated with an excess of 1M hydrogen chloride in ether (~5 ml) for 10 minutes. The mixture was evaporated once more and the residue was dissolved in dichloromethane (4 ml) and dimethylformamide (2 ml) and filtered to remove solids. The resulting solution was transferred to a reaction tube and 1-hydroxybenzotriazole (0.117 g, 0.87 mmol), [(2-chloro-4-fluorophenyl)methyl]amine (0.138 g, 0.87 mmol) and N-(3-dimethylaminopropyl)-N'-ethylcarbodiimide hydrochloride (0.167 g, 0.87 mmol) were then added. The mixture was flushed with argon and then stirred at room temperature over the weekend. The mixture was then diluted with dichloromethane and washed sequentially with 2M aqueous hydrogen chloride and saturated aqueous sodium hydrogen carbonate. The organic layer was filtered through a phase separator and then evaporated to give the crude product. The crude material was purified by mass-directed automated HPLC to give pure N-[(2-chloro-4-fluorophenyl)methyl]-1-ethyl-5-oxo-prolinamide (0.086 g) as a white solid. LC/MS [M+H]$^+$= 299.1, retention time=2.13 minutes.

Enantiomeric excess=100.0%, as determined by chiral chromatography method B, indicative of N-[(2,4-dichlorophenyl)methyl]-1-methyl-5-oxo-L-prolinamide retention time=8.05 minutes The methyl 1-ethyl-5-oxo-prolinate used in the above procedure was prepared as follows:

(i) Dimethyl L-glutamate hydrochloride (0.500 g, 2.37 mmol) was dissolved in methanol (4 ml) and tetrahydrofuran (8 ml) and the mixture was then treated with crushed sodium hydroxide (0.099 g, 2.49 mmol) for 10 minutes. At this stage acetic acid (0.136 ml, 2.37 mmol) and acetaldehyde (0.199 ml, 3.55 mmol) were added together to the mixture as a solution in tetrahydrofuran (1 ml). After stirring for 10 minutes the mixture was cooled to 0° C. and treated with sodium borohydride pellets (0.088 g, 2.37 mmol). The mixture was then left to warm to room temperature. Once the mixture had reached room temperature it was diluted with ethyl acetate (30 ml) and washed with saturated aqueous sodium hydrogen carbonate, filtered through a phase separator (with stirring) and evaporated to give an oily residue. The oil was dissolved in toluene and heated at reflux for 4 hrs. To ensure complete reaction the mixture was then heated overnight at reflux. The solvent was then evaporated and the resulting residue was purified by flash-silica column chromatography, eluting with a gradient of 30-50% ethyl acetate in hexane, to give crude methyl 1-ethyl-5-oxo-prolinate (0.135 g) as a clear oil which was used without further purification.

Examples 4-8

In a manner analogous to that described for Example 3 above the compounds tabulated below (Table 1) were prepared by substituting the appropriate aldehyde (or ketone) for the acetaldehyde used in the above procedure. All of the aldehydes and ketones used to make the compounds shown in Table 1 are available from commercial sources or can be prepared using routes described previously in the chemical literature.

TABLE 1

| Example no. | Chemical name | [M + H]$^+$ | Retention time (mins) |
|---|---|---|---|
| E4 | N-[(2-chloro-4-fluorophenyl)methyl]-5-oxo-1-propyl-prolinamide | 313.1 | 2.30 |

TABLE 1-continued

| Example no. | Chemical name | [M + H]+ | Retention time (mins) |
|---|---|---|---|
| E5 | N-[(2-chloro-4-fluorophenyl)methyl]-1-(2-methylpropyl)-5-oxo-prolinamide | 327.1 | 2.46 |
| E6 | N-[(2-chloro-4-fluorophenyl)methyl]-1-cyclopentyl-5-oxo-prolinamide | 339.1 | 2.47 |
| E7 | N-[(2-chloro-4-fluorophenyl)methyl]-1-cyclobutyl-5-oxoprolinamide | 325 | 2.37 |
| E8 | N-[(2-chloro-4-fluorophenyl)methyl]-1-(1-methylpropyl)-5-oxoprolinamide | 327 | 2.43 |

Example 9

N-[(2-chloro-4-fluorophenyl)methyl]-5-oxo-1-phenyl-prolinamide (E9)

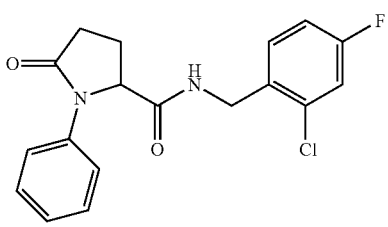

5-oxo-1-phenyl-proline (0.047 g, 0.23 mmol, prepared as described below) was dissolved in dichloromethane (~2 ml) and dimethylformamide (1 ml) and to this was added 1-hydroxybenzotriazole (0.034 g, 0.25 mmol), [(2-chloro-4-fluorophenyl)methyl]amine (0.040 g, 0.25 mmol), N-ethyl morpholine (0.032 ml, 0.25 mmol) and N-(3-dimethylaminopropyl)-N'-ethylcarbodiimide hydrochloride (0.048 g, 0.25 mmol). The mixture was stirred at room temperature for 4.5 hrs. The mixture was diluted with more dichloromethane and washed sequentially with 2M aqueous hydrogen chloride and saturated aqueous sodium hydrogen carbonate. The organic layer was filtered through a phase separator and then evaporated to give the crude product. The crude material was purified by mass-directed automated HPLC to give pure N-[(2-chloro-4-fluorophenyl)methyl]-5-oxo-1-phenyl-prolinamide (0.032 g) as a white solid. LC/MS [M+H]+=347.1, retention time=2.51 minutes.

The 5-oxo-1-phenyl-proline used in the above procedure was prepared as follows:

(i) Methyl 5-oxo-L-prolinate (0.204 ml, 1.75 mmol) was dissolved in toluene (5 ml) and treated with tris(dibenzylideneacetone)dipalladium (0) (0.024 g, 0.03 mmol), bromobenzene (0.184 ml, 1.75 mmol), cesium carbonate (0.795 g, 2.45 mmol) and Xantphos™ (0.040 g, 0.07 mmol). The resulting mixture was heated at 120° C. for ~18 hrs and then allowed to cool to room temperature. The mixture was diluted with ethyl acetate and washed sequentially with 2M aqueous hydrogen chloride, saturated aqueous sodium hydrogen carbonate, and brine. Filtration through a phase separator followed by evaporation gave a yellow/brown oil (~0.200 g). The crude material was purified by mass-directed automated HPLC to give pure methyl 5-oxo-1-phenylprolinate (0.054 g) as an oil which crystallised on standing. LC/MS [M+H]$^+$=220, retention time=2.03 minutes.

(ii) Methyl 5-oxo-1-phenylprolinate (0.054 g, 0.25 mmol) was combined with 2M aqueous sodium hydroxide (0.160 ml, 0.32 mmol) in methanol (1 ml) and stirred overnight at room temperature. The solvent was then evaporated and the residue taken up in ethyl acetate and washed with 2M aqueous hydrogen chloride. The aqueous layer was separated and washed twice more with ethyl acetate and then the combined ethyl acetate layers were dried using a phase separator and evaporated to give 5-oxo-1-phenyl-proline (0.047 g) as a clear oil.

Example 10

N-[(2,4-dichlorophenyl)methyl]-1-methyl-5-oxo-prolinamide (E10)

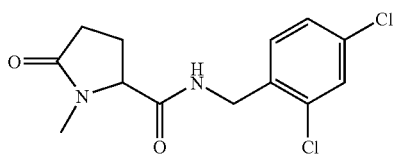

1-Methyl-5-oxo-proline (0.057 g, 0.4 mmol, prepared as described below) was dissolved in anhydrous dichloromethane (6 ml) and to this was added 1-hydroxybenzotriazole (0.060 g, 0.4 mmol), [(2,4-dichloro-phenyl)methyl]amine (0.055 ml, 0.4 mmol), diisopropylamine (0.140 ml, 0.8 mmol) and O-(7-azabenzotriazol-1-yl)-N,N,N',N'-tetramethyluronium hexafluorophosphate (0.152 g, 0.4 mmol). The mixture was stirred at room temperature (20° C.) under argon for 3 hrs and then overnight. The mixture was diluted with more dichloromethane (25 ml) and washed sequentially with 2M aqueous hydrogen chloride (20 ml), saturated aqueous sodium hydrogen carbonate (20 ml), 10% aqueous sodium carbonate (20 ml) and brine (20 ml). The organic layer was filtered through a hydrophobic frit and then evaporated to give the crude product. The crude material was dissolved in a mixture of dimethylsulphoxide (0.9 ml) and acetonitrile (0.9 ml) and then purified by mass-directed automated HPLC to give pure N-[(2,4-dichlorophenyl)methyl]-1-methyl-5-oxo-prolinamide (0.085 g) as a white solid. LC/MS [M+H]$^+$=301, retention time=2.16 minutes.

The 1-methyl-5-oxo-proline used in the above procedure was prepared as follows:

(i) N-methyl-L-glutamic acid (0.500 g, 3.1 mmol) was dissolved in water (1 ml) and heated in a sealed tube at 140° C. for 30 minutes in a microwave reactor. The water was then evaporated and the residue triturated with ether to give, after drying, 1-methyl-5-oxo-proline (0.298 g) as a white solid.

N-[(2,4-dichlorophenyl)methyl]-1-methyl-5-oxo-prolinamide can also be prepared as described below:

1-Methyl-5-oxo-proline (36.79 g, 0.257 moles, prepared as described above) was suspended in DCM (dichloromethane) (500 ml). EEDQ (2-Ethoxy-1-ethoxycarbonyl-1,2-dihydroquinoline, 66.7 g, 0.27 moles, 1.05 eq) was added in one portion. All material seemed to dissolve to give an opaque mixture and the temperature dropped from 21° C. to 10° C. This was stirred for 20 minutes under argon and then a solution of 2,4-dichlorobenzylamine (36 ml, 0.27 moles, 1.05 eq) in DCM (100 ml) was added dropwise over a period of 40 minutes. During addition, a white precipitate formed in the dropping funnel. The mixture bubbled gently and an ice/water bath was used to maintain the temperature between 15-20° C. Upon complete addition of amine, the dropping funnel was rinsed with further DCM (50 ml) to rinse all the precipitate into the reaction mixture. The mixture was then allowed to warm to room temperature and stirred for approx. 18 hours. Saturated aqueous sodium hydrogen carbonate (200 ml) was added to the mixture and stirred for 5 minutes. The organic layer was then separated and washed with 2N HCl (3×250 ml). During the acid washes, crystals started to form in the organic layer, so this was diluted with further DCM (200 ml). The organic layer was dried by passing through a hydrophobic frit and then concentrated under vacuum to give 65 g of pink solids. The solids had formed large lumps so the crude material was ground up in a pestle and mortar. These were then triturated with diethyl ether (400 ml) and the solids filtered off and washed with further Et$_2$O (2×200 ml). Drying then gave 52.96 g of pale pink solids. This material was combined with 2 further batches, prepared in the same way, (141.42 g total) and then suspended in ethanol (430 ml) and water (715 ml) and gradually warmed to 65° C. (temperature of solution). The mixture gave an almost clear solution (deep pink), except for a very fine solid suspension. After heating at 65° C. for 20 minutes, the flask was removed from the heat and allowed to warm to room temperature overnight. After this time, white needles had precipitated from solution. The mixture was cooled in an ice bath for 20 minutes to ensure all solids had precipitated. The white solids were then filtered off from the pink solution and washed with portions of 3:5 EtOH/H$_2$O (2×400 ml), which had been cooled in an ice bath. The solids were dried in a vacuum oven (40° C.) for a total of 5 days to give pure N-[(2,4-dichlorophenyl)methyl]-1-methyl-5-oxo-prolinamide (125.37 g) as colourless crystals. LC/MS [M+H]$^+$=301, retention time=2.34 minutes.

$^1$H NMR (CDCl$_3$, 500 MHz) δ 2.01 (m, 1H), 2.34 (m, 1H), 2.37 (m, 1H), 2.46 (m, 1H), 2.80 (s, 3H), 3.99 (dd, 1H, J=9.1, 4.2 Hz), 4.49 (dd, 1H, J=14.9, 5.9 Hz), 4.55 (dd, 1H, J=14.8, 6.1 Hz), 6.56 (broad t, 1H, J=5.7 Hz), 7.24 (dd, 1H, J=8.2, 2.1 Hz), 7.33 (d, 1H, J=8.2 Hz), 7.40 (d, 1H, J=2.1 Hz); $^{13}$C NMR δ 175.9, 171.3, 134.5, 134.3, 133.7, 131.5, 129.6, 127.5, 63.8, 41.2, 29.4, 29.2, 23.4.

Enantiomeric excess=99.5%, as determined by chiral chromatography method A, indicative of N-[(2,4-dichlorophenyl)methyl]-1-methyl-5-oxo-L-prolinamide retention time=9.89 minutes

[α]$_D$=−2.1° (c=1, MeOH), Temperature=29.3° C., wavelength=589 nm melting point=144.0-144.8° C.

Example 11

N-[(2-chloro-4-fluorophenyl)methyl]-1-methyl-5-oxo-prolinamide (E11)

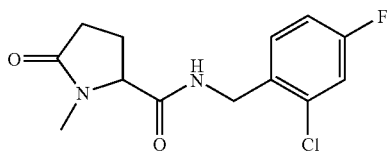

1-Methyl-5-oxo-proline (0.050 g, 0.35 mmol, prepared as described below) was dissolved in anhydrous dichloromethane (~7 ml) and to this was added 1-hydroxybenzotriazole (0.047 g, 0.42 mmol), [(2-chloro-4-fluorophenyl)methyl]amine (0.056 ml, 0.42 mmol), N-ethyl morpholine (0.166 ml, 1.04 mmol) and N-(3-dimethylaminopropyl)-N'-ethylcarbodiimide hydrochloride (0.067 g, 0.42 mmol). The mixture was stirred at room temperature overnight. A further aliquot of [(2-chloro-4-fluorophenyl)methyl]amine (0.100 ml, 0.8 mmol) was added to the mixture and stirring continued for a while longer but HPLC indicated that no further product was forming. The mixture was washed sequentially with 2M aqueous hydrogen chloride (5 ml) and saturated aqueous sodium hydrogen carbonate (5 ml). The organic layer was collected and evaporated to give the crude product. The crude material was purified by mass-directed automated HPLC to give pure N-[(2-chloro-4-fluorophenyl)methyl]-1-methyl-5-oxo-prolinamide (0.015 g) as a white solid. LC/MS [M+H]$^+$=285, retention time=2.04 minutes.

The 1-methyl-5-oxo-proline used in the above procedure was prepared as follows:

(i) (L)-pyroglutamic acid methyl ester (1 g, 6.99 mmol) was dissolved/mixed with tetrahydrofuran (10 ml) and cooled to 0° C. using an ice-bath. Sodium hydride (0.201 g of a 60% suspension in oil, 8.38 mmol) was added to the mixture. After bubbling stopped, methyl iodide (0.522 ml, 8.38 mmol) was added and the mixture was allowed to warm to room temperature and then stirred for 1 hr. The solvent was evaporated and water was added (1 ml). The aqueous layer was then extracted with dichloromethane. Evaporation of the dichloromethane gave crude methyl 1-methyl-5-oxo-prolinate (0.308 g) which was used in the next step without further purification.

(ii) Methyl 1-methyl-5-oxo-prolinate (0.308 g, 1.96 mmol) was dissolved in methanol (~10 ml) and to this was added a solution of sodium hydroxide (0.157 g, 3.92 mmol) in water (~10 ml). The mixture was heated at reflux for 3 hrs, then cooled and evaporated to leave a minimal amount of water. This was acidified to pH 1 using 2M aqueous hydrogen chloride. The aqueous layer was washed with dichloromethane and then separated and evaporated to give 1-methyl-5-oxo-proline as a white solid (0.300 g).

Example 12

1-Ethyl-5-oxo-N-[(2,3,4-trifluorophenyl)methyl]-prolinamide (E12)

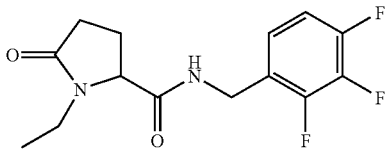

1-Ethyl-5-oxo-proline (0.050 g, 0.32 mmol) was dissolved in anhydrous dichloromethane (~7 ml) and dimethylformamide (1 ml) and to this was added 1-hydroxybenzotriazole (0.052 g, 0.38 mmol), [(2,3,4-trifluorophenyl)methyl]amine (0.103 g, 0.64 mmol), N-ethyl morpholine (0.151 ml, 0.95 mmol) and N-(3-dimethylaminopropyl)-N'-ethylcarbodiimide hydrochloride (0.073 g, 0.38 mmol). The mixture was shaken at room temperature over the weekend. A further aliquot of [(2,3,4-trifluorophenyl)methyl]amine (0.051 g, 0.32 mmol) was added to the mixture and stirring continued for a while longer until HPLC indicated that no further product was forming. The mixture was diluted with 2M aqueous hydrogen chloride (5 ml) and then filtered through a phase separator. The organic layer was then washed with saturated aqueous sodium hydrogen carbonate and again filtered through a phase separator. The organic layer was then evaporated to give the crude product. The crude material was purified by mass-directed automated HPLC to give pure 1-ethyl-5-oxo-N-[(2,3,4-trifluorophenyl)methyl]-prolinamide (0.032 g).

LC/MS [M+H]$^+$=301, retention time=2.03 minutes.

The 1-ethyl-5-oxo-proline used in the above procedure was prepared as follows (Method A):

(i) Dimethyl L-glutamate hydrochloride (5.0 g, 23.7 mmol) was dissolved in methanol (100 ml) and the mixture was then treated with ground sodium hydroxide (1.0 g, 24.9 mmol) under argon at room temperature. After 5 minutes, acetaldehyde (1.99 ml, 35.5 mmol) was added and stirring continued for 10 minutes. The mixture was cooled to 0° C. and treated with sodium borohydride granules (0.701 g, 18.95 mmol). Stirring was continued for 1 hr at 0° C. and then the methanol was evaporated off and the residue was taken up in ethyl acetate and filtered. The filtrate was then washed with brine and the brine washing was extracted with ethyl acetate. The combined ethyl acetate fractions were filtered through a hydrophobic frit and evaporated to give a clear oil (3.2 g). The oil was dissolved in toluene (30 ml) and heated at reflux overnight. The toluene was then evaporated to give a light orange residue which was purified by flash-silica column chromatography, eluting with a gradient of 20-60% ethyl acetate in hexane, to give partially pure methyl 1-ethyl-5-oxo-prolinate (1.9 g) as a clear oil. This was used in the next step without further purification.

(ii) Methyl 1-ethyl-5-oxo-prolinate (1.91 g, 11.17 mmol) was dissolved in methanol (25 ml) and treated with 2M aqueous sodium hydroxide (7.3 ml, 14.52 mmol). The mixture was stirred for 4 hrs at room temperature and then washed with dichloromethane. The aqueous layer was evaporated and the residue treated with an excess of 1M hydrogen chloride in ether (~5 ml). The mixture was evaporated once more and the residue was triturated with dichloromethane. The solid material was discarded and the combined dichloromethane fractions were evaporated to give a clear oil which crystallized on standing. Trituration with hexane and ether and drying gave pure 1-ethyl-5-oxo-proline (0.271 g) as a white solid.

Alternatively, 1-ethyl-5-oxo-proline may be prepared as follows (Method B):

(i) 1,1-dimethylethyl 5-oxo-L-prolinate (2.7 g, 12 mmol, prepared as described in *Synth. Comm.*, 2005, 35(8), 1129) was added to a suspension of sodium hydride (0.428 g (60% suspension in oil), 10.7 mmol) in tetrahydrofuran (6 ml) and the mixture was stirred at room temperature for 5 minutes. Ethyl iodide (1.67 g, 10.7 mmol) was then added and the mixture was heated at 40° C. for 2 hrs. A further quantity of sodium hydride (0.24 g) was added and stirring continued overnight at room temperature. An additional quantity of ethyl iodide (0.86 ml) was added to the mixture at this stage and the mixture was left to stand at room temperature over the weekend. Water (~10 ml) was added to the mixture and this was stirred for 15 minutes. The tetrahydrofuran was evaporated and the remaining aqueous layer was extracted with dichloromethane (2×50 ml) and a 3:1 mixture of chloroform and isopropanol (50 ml). The combined organic layers were filtered through a hydrophobic frit and evaporated to give a yellow oil. Toluene was added to the mixture and then evaporated to a yellow oil once more. This material was purified by automated silica flash-column chromatography (Biotage SP4), eluting with a 15-100% gradient of ethyl acetate in hexane, to give pure 1,1-dimethylethyl 1-ethyl-5-oxo-prolinate.

(ii) 1,1-Dimethylethyl 1-ethyl-5-oxo-prolinate (0.965 g) was dissolved in dichloromethane (~5 ml) and treated with trifluoroacetic acid (1 ml). The mixture was stirred at room temperature for 1.5 hrs and then evaporated. The resulting material was mostly starting material so a further amount of trifluoroacetic acid (1 ml) and dichloromethane (~5 ml) was added and the mixture stirred at room temperature for 36 hrs. The mixture was evaporated and then toluene was added to the residue and this was in turn also evaporated. After repeating this process once more, crude 1-ethyl-5-oxo-proline was obtained as a dark yellow oil which was used without additional purification.

Alternatively, 1-ethyl-5-oxo-proline may be prepared as follows (Method C):

(i) 1-(1,1-Dimethylethyl) 5-methyl-L-glutamate hydrochloride (5.0 g, 19.71 mmol) was dissolved in a mixture of methanol (30 ml) and tetrahydrofuran (60 ml) and the mixture was then treated with crushed, powdered sodium hydroxide (0.828 g, 20.69 mmol) under argon at room temperature. After stirring for 10 minutes, acetaldehyde (1.11 ml, 19.71 mmol) and acetic acid (1.13 ml, 19.71 mmol) were added and stirring continued for 10-15 minutes. The mixture was cooled to 0° C. in an ice-bath and treated with sodium borohydride pellets (0.746 g, 19.71 mmol). Stirring was continued for ~1 hr at 0° C. under argon. The mixture was allowed to warm to room temperature to give a thick suspension. Fine white solids were filtered off and then the methanol was evaporated off and the residue was taken up in dichloromethane (~50 ml) and washed with saturated aqueous sodium hydrogen carbonate (~25 ml). The organic layer was separated using a phase separator and then the aqueous layer was back extracted with more dichloromethane (2×20 ml). The combined organic layers were evaporated to give a colourless oil (~4 g). The oil (3 g, assume 14.8 mmol) was dissolved in toluene (30 ml) and heated at reflux for ~16 hrs overnight to give an orange solution. The toluene was then evaporated to give an orange oil (2.6 g). This was combined with a further batch of oil (0.850 g) which was obtained in the same manner and then purified by automated flash-silica column chromatography (Biotage SP4), eluting with a gradient of 20-80% ethyl acetate in hexane, to give pure 1,1-dimethylethyl 1-ethyl-5-oxoprolinate (2.14 g).

(ii) 1,1-Dimethylethyl 1-ethyl-5-oxoprolinate (0.933 g) was dissolved in dichloromethane (~5 ml) and treated with trifluoroacetic acid (1 ml). The mixture was stirred for 3 hrs at room temperature and then evaporated. The residue was taken up in toluene and evaporated once more. This gave partially pure (>95%) 1-ethyl-5-oxo-proline as an orange/yellow oil (0.914 g) which was used without further purification.

Examples 13-36

In a manner analogous to that described for Example 12 above the compounds tabulated below (Table 2) were prepared by substituting the appropriate amine (or salt thereof) for the [(2,3,4-trifluorophenyl)methyl]amine used in the above procedure. All of the amines used to make the compounds shown in Table 2 are available from commercial sources or can be prepared using routes described previously in the chemical literature or by methods analogous to those. The 1-ethyl-5-oxo-proline used in the reaction was prepared, in each case, by the method indicated. Where determined (by chiral HPLC), the enantiomeric excess (e.e.) of the isomer shown is also listed along with its stereospecific name, the chiral separation method used in parentheses and the corresponding retention time (r.t.) in that method.

TABLE 2

| Example no. | Chemical name | [M + H]$^+$ | Retention time (mins) | Method used to prepare 1-ethyl-5-oxo-proline | e.e. |
|---|---|---|---|---|---|
| E13 | 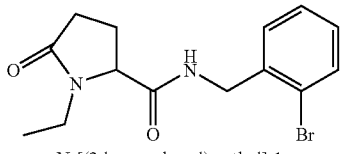 N-[(2-bromophenyl)methyl]-1-ethyl-5-oxo-prolinamide | 327 | 2.04 | A | |
| E14 | 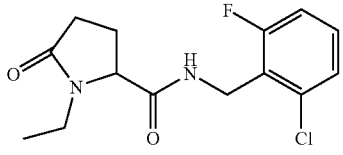 N-[(2-chloro-6-fluorophenyl)methyl]-1-ethyl-5-oxo-prolinamide | 299 | 2.03 | A | |
| E15 | 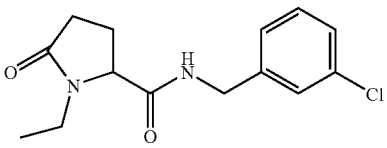 N-[(3-chlorophenyl)methyl]-1-ethyl-5-oxo-prolinamide | 281 | 2.13 | A | |

TABLE 2-continued

| Example no. | Chemical name | [M + H]⁺ | Retention time (mins) | Method used to prepare 1-ethyl-5-oxo-proline | e.e. |
|---|---|---|---|---|---|
| E16 | 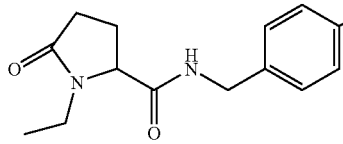<br>N-[(4-chlorophenyl)methyl]-1-ethyl-5-oxo-prolinamide | 281 | 2.07 | A | |
| E17 | 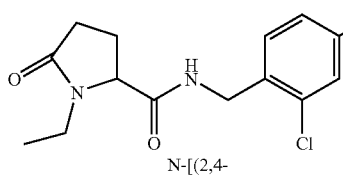<br>N-[(2,4-dichlorophenyl)methyl]-1-ethyl-5-oxo-prolinamide | 315 | 2.39 | A | 96.9%<br>(C)<br>N-[(2,4-dichlorophenyl)methyl]-1-ethyl-5-oxo-L-prolinamide<br>r.t. = 8.78 mins |
| E18 | 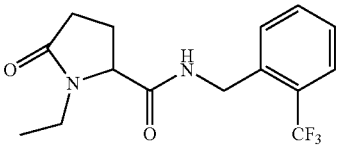<br>1-Ethyl-5-oxo-N-{[2-(trifluoromethyl)phenyl]methyl}-prolinamide | 315 | 2.29 | B | |
| E19 | 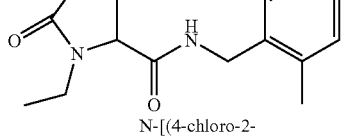<br>N-[(4-chloro-2-methylphenyl)methyl]-1-ethyl-5-oxo-prolinamide | 295 | 2.37 | B | |
| E20 | 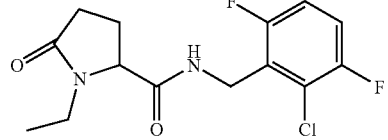<br>N-[(2-chloro-3,6-difluorophenyl)methyl]-1-ethyl-5-oxo-prolinamide | 317 | 2.15 | B | |
| E21 | 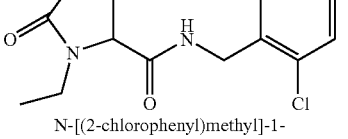<br>N-[(2-chlorophenyl)methyl]-1-ethyl-5-oxo-prolinamide | 281 | 2.10 | B | |
| E22 | 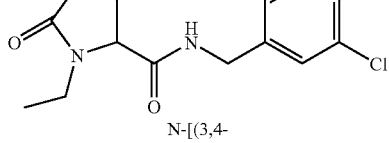<br>N-[(3,4-dichlorophenyl)methyl]-1-ethyl-5-oxo-prolinamide | 315 | 2.36 | B | 82.8%<br>(C)<br>N-[(3,4-dichlorophenyl)methyl]-1-ethyl-5-oxo-L-prolinamide<br>r.t. = 5.37 mins |

TABLE 2-continued

| Example no. | Chemical name | [M + H]+ | Retention time (mins) | Method used to prepare 1-ethyl-5-oxo-proline | e.e. |
|---|---|---|---|---|---|
| E23 | 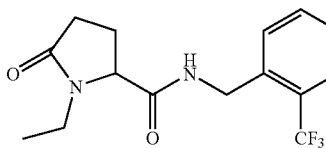<br>1-Ethyl-N-{[4-fluoro-2-(trifluoromethyl)phenyl]methyl}-5-oxo-prolinamide | 333 | 2.33 | B | |
| E24 | 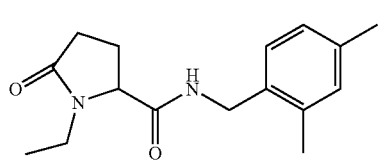<br>N-[(2,4-dimethylphenyl)methyl]-1-ethyl-5-oxo-prolinamide | 275 | 2.24 | B | |
| E25 | 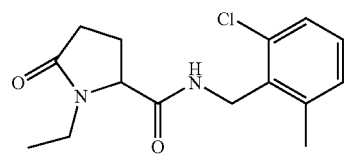<br>N-[(2-chloro-6-methylphenyl)methyl]-1-ethyl-5-oxo-prolinamide | 295 | 2.28 | B | 79.0% (C) N-[(2-chloro-6-methylphenyl)methyl]-1-ethyl-5-oxo-L-prolinamide r.t. = 6.91 mins |
| E26 | 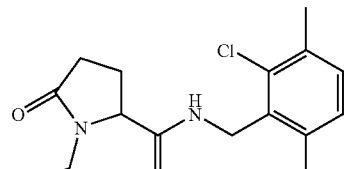<br>N-[(2-chloro-6-fluoro-3-methylphenyl)methyl]-1-ethyl-5-oxo-prolinamide | 313 | 2.31 | B | |
| E27 | 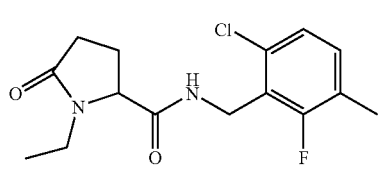<br>N-[(6-chloro-2-fluoro-3-methylphenyl)methyl]-1-ethyl-5-oxo-prolinamide | 313 | 2.20 | B | |
| E28 | 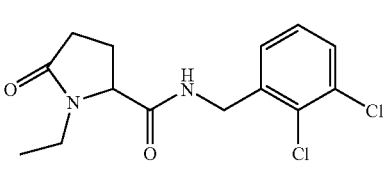<br>N-[(2,3-dichlorophenyl)methyl]-1-ethyl-5-oxoprolinamide | 315 | 2.29 | C | |

TABLE 2-continued

| Example no. | Chemical name | [M + H]⁺ | Retention time (mins) | Method used to prepare 1-ethyl-5-oxo-proline | e.e. |
|---|---|---|---|---|---|
| E29 | 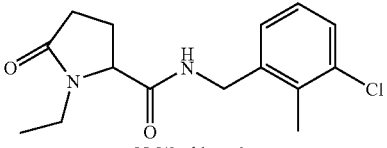<br>N-[(3-chloro-2-methylphenyl)methyl]-1-ethyl-5-oxoprolinamide | 295 | 2.30 | C | |
| E30 | 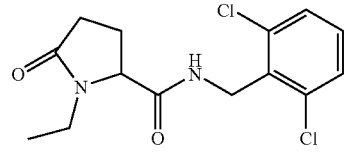<br>N-[(2,6-dichlorophenyl)methyl]-1-ethyl-5-oxoprolinamide | 315 | 2.19 | C | |
| E31 | 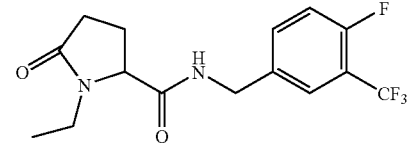<br>1-Ethyl-N-{[4-fluoro-3-(trifluoromethyl)phenyl]methyl}-5-oxoprolinamide | 333 | 2.35 | C | |
| E32 | 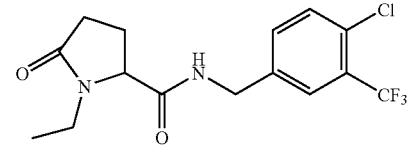<br>N-{[4-chloro-3-(trifluoromethyl)phenyl]methyl}-1-ethyl-5-oxoprolinamide | 349 | 2.49 | C | 99.1 (A)<br>N-{[4-chloro-3-(trifluoromethyl)phenyl]methyl}-1-ethyl-5-oxo-L-prolinamide<br>r.t. = 5.44 mins |
| E33 | 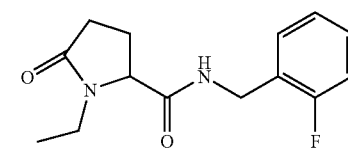<br>N-[(4-bromo-2-fluorophenyl)methyl]-1-ethyl-5-oxoprolinamide | 345 | 2.24 | C | |
| E34 | <br>1-Ethyl-N-[(2-methylphenyl)methyl]-5-oxoprolinamide | 261 | 2.00 | C | |
| E35 | 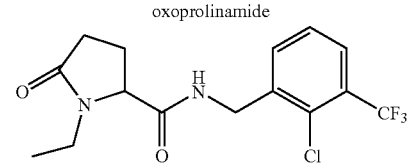<br>N-{[2-chloro-3-(trifluoromethyl)phenyl]methyl}-1-ethyl-5-oxoprolinamide | 349 | 2.45 | C | 100.0 (A)<br>N-{[2-chloro-3-(trifluoromethyl)phenyl]methyl}-1-ethyl-5-oxo-L-prolinamide<br>r.t. = 5.51 mins |

TABLE 2-continued

| Example no. | Chemical name | [M + H]+ | Retention time (mins) | Method used to prepare 1-ethyl-5-oxo-proline | e.e. |
|---|---|---|---|---|---|
| E36 | N-[(2-chloro-3,4-difluorophenyl)methyl]-1-ethyl-5-oxoprolinamide | 317 | 2.22 | C | |

The [(2-chloro-3,4-difluorophenyl)methyl]amine hydrochloride required for the synthesis of N-[(2-chloro-3,4-difluorophenyl)methyl]-1-ethyl-5-oxoprolinamide (Example 36) was prepared in the following manner:

(i) A solution of N,N,N',N'-tetramethylethylenediamine (39.6 ml, 264 mmol) in tetrahydrofuran (170 ml) was cooled under argon to −70° C. before the addition of sec-butyl lithium (205 ml, 288 mmol). To the mixture 3,4-difluorobenzoic acid (19 g, 120 mmol) was then added as a solution in tetrahydrofuran (80 ml) over a period of 40 minutes ensuring that the temperature of the mixture did not rise above −60° C. The mixture was then stirred at a temperature of −68° C. to −70° C. for 1 hr before adding a solution of hexachloroethane (100 g, 422 mmol) in tetrahydrofuran (170 ml) over a period of 35 minutes whilst keeping the temperature of the mixture below −60° C. The mixture was stirred at a temperature of −65° C. to −70° C. for 2 hrs. The mixture was allowed to warm to −10° C. and then water (500 ml) was added to quench the reaction. The mixture was diluted with diethyl ether (250 ml) and the two resulting layers were separated. The aqueous layer was acidified to pH1 using concentrated aqueous hydrogen chloride and then extracted with 2×500 ml aliquots of diethyl ether. The combined organic extracts were passed through a hydrophobic frit and reduced in vacuo to give a yellow solid. This was recrystallised from ethyl acetate to give two crops (8.35 g and 4.47 g) of pure 2-chloro-3,4-difluorobenzoic acid.

(ii) 2-Chloro-3,4-difluorobenzoic acid (2 g, 10.4 mmol) was treated with thionyl chloride (3.04 ml) and the mixture was heated to 80° C. for 90 minutes. The mixture was then cooled and reduced in vacuo. The residue was dissolved in anhydrous 1,4-dioxane (10 ml) and the mixture was then cooled in an ice-water bath. 0.88 Ammonia (aqueous, 25 ml) was added dropwise to the mixture which was subsequently allowed to warm to 22° C. over a period of 2 hrs. This process was repeated using 10.8 g of 2-chloro-3,4-difluorobenzoic acid, 8.2 ml of thionyl chloride, and 45 ml of 0.88 ammonia and then both mixtures were combined and partitioned between ethyl acetate (150 ml) and water (100 ml). The aqueous layer was separated and extracted with 2×150 ml aliquots of ethyl acetate. The combined organic extracts were then washed with saturated aqueous sodium hydrogen carbonate (100 ml), dried using a hydrophobic frit, and reduced in vacuo to give 2-chloro-3,4-difluorobenzamide (11.86 g) as a white solid.

LC/MS [M+H]+=192/194, retention time=1.69 minutes.

(iii) 2-Chloro-3,4-difluorobenzamide (11.85 g, 62 mmol) was dissolved in tetrahydrofuran (200 ml) and treated with 1M borane tetrahydrofuran (247 ml, 247 mmol). The mixture was heated to 70° C. and stirred for 18 hrs. The mixture was then cooled in an ice-water bath and concentrated aqueous hydrogen chloride (150 ml) was added dropwise. Heating, with stirring, at 70° C. was then resumed for a further 2 hrs. The mixture was then allowed to cool and the solvent was evaporated in vacuo. The residue was partitioned between ethyl acetate (200 ml) and 2N aqueous hydrogen chloride (200 ml). The aqueous layer was separated and the pH was adjusted to 8-9 by dropwise addition of 5N aqueous sodium hydroxide. The resulting cloudy suspension was extracted with ethyl acetate (4×200 ml) and the combined organic extracts were then passed through a hydrophobic frit and reduced in volume to ~200 ml. The mixture was then acidified by the addition of 1M ethereal hydrogen chloride (100 ml) resulting in formation of a precipitate. The solvent was evaporated in vacuo to give a white solid. The solid was recrystallised from methylated spirit (60 ml) to give three crops of pure [(2-chloro-3,4-difluorophenyl)methyl]amine hydrochloride (combined mass=4.46 g) as a white solid.

Example 37

N-[(2-chloro-4-fluorophenyl)methyl]-1-ethyl-5-oxo-4-(phenylmethyl)prolinamide (E37)

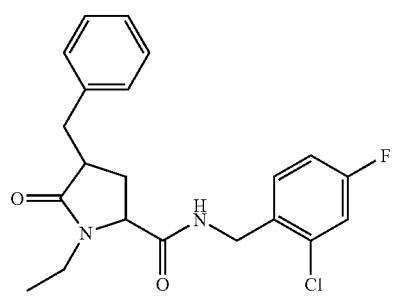

Crude 1-ethyl-5-oxo-4-(phenylmethyl)-proline (0.052 g, 0.09 mmol, prepared as described below) was suspended in a mixture of dichloromethane (0.5 ml) and dimethylformamide (0.5 ml) and to this was added N-ethyl morpholine (0.034 ml, 0.27 mmol) causing most of the material to dissolve. 1-Hydroxybenzotriazole (0.016 g, 0.12 mmol) and N-(3-dimethylaminopropyl)-N'-ethylcarbodiimide hydrochloride (0.022 g, 0.12 mmol) were then added and the mixture was stirred for 10 minutes before adding [(2-chloro-4-fluorophenyl)methyl] amine (0.019 g, 0.12 mmol). The mixture was then left to stand at room temperature overnight. Saturated aqueous sodium hydrogen carbonate (~2 ml) was added to the mixture and stirred for 10 minutes. The organic layer was isolated by filtering through a phase separator and then washed with 2M aqueous hydrogen chloride. The organic layer was separated again and evaporated to give a yellow oil which was purified by mass-directed automated HPLC to give pure N-[(2-chloro-4-fluorophenyl)methyl]-1-ethyl-5-oxo-4-(phenylmethyl)-prolinamide (0.004 g) as a colourless oil. LC/MS [M+H]$^+$= 389, retention time=2.90 minutes.

The 1-ethyl-5-oxo-4-(phenylmethyl)-proline used in the above procedure was prepared as follows (Method A):

(i) Methyl (S)-(+)-2-pyrrolidinone-5-carboxylate (0.85 g, 5.94 mmol) was dissolved in dichloromethane (5 ml) and treated with triethylamine (0.869 ml, 6.24 mmol) and 4-dimethylaminopyridine (0.010 g). To this was added di-tertbutyl dicarbonate (1.36 g, 6.24 mmol) and the resulting orange solution was left to stir overnight. The mixture turned blue/grey and evaporation of the solvent gave a grayish oil (1.4 g). This was purified by automated flash-silica column chromatography (Biotage SP4), eluting with a 0-60% gradient of ethyl acetate in hexane, to give 1-(1,1-dimethylethyl) 2-methyl-5-oxo-1,2-pyrrolidinedicarboxylate (1.37 g) as colourless oil which crystallized on standing.

(ii) 1-(1,1-Dimethylethyl) 2-methyl-5-oxo-1,2-pyrrolidinedicarboxylate (0.324 g, 1.33 mmol) was dissolved in tetrahydrofuran (3 ml) and the mixture was cooled to –78° C., using an acetone/cardice bath, under an atmosphere of argon. A 1M solution of lithium bis(trimethylsilyl)amide in tetrahydrofuran (1.4 ml, 1.40 mmol) was added dropwise and stirred under argon for 1 hour. To this was then added benzyl bromide (0.174 ml, 1.46 mmol) and the mixture was stirred at –78° C. for a further 2.5 hrs. The mixture was then allowed to warm to room temperature and quenched by the addition of saturated aqueous ammonium chloride (~5 ml) and then left to stand overnight at room temperature. The organic layer was separated and the aqueous layer was diluted with more water (5 ml) and extracted with ethyl acetate (3×10 ml). The combined organic layers were dried over anhydrous sodium sulphate and then filtered and concentrated to give a yellow oil (0.700 g). This was purified by automated flash-silica column chromatography (Biotage SP4), eluting with a 0-35% gradient of ethyl acetate in hexane, to give 1-(1,1-dimethylethyl) 2-methyl-5-oxo-4-(phenylmethyl)-1,2-pyrrolidinedicarboxylate as a white solid (0.418 g) after evaporation of solvent.

(iii) 1-(1,1-Dimethylethyl) 2-methyl-5-oxo-4-(phenylmethyl)-1,2-pyrrolidinedicarboxylate (0.415 g, 1.24 mmol) was dissolved in 4M hydrogen chloride in dioxane (2 ml) and stirred at room temperature for 2 hrs. The solvent was evaporated to give a colourless oil which crystallized on standing to give methyl-5-oxo-4-(phenylmethyl)-prolinate as a creamy/white solid (0.205 g). This was used without further purification in the next step.

(iv) Methyl-5-oxo-4-(phenylmethyl)-prolinate (0.205 g, 0.88 mmol) was dissolved in tetrahydrofuran (2.5 ml) and treated with ethyl iodide (0.077 ml, 0.97 mmol). The mixture was then cooled to 0° C. and treated with sodium hydride (0.037 g of a 60% suspension in oil, 0.92 mmol). After stirring at 0° C. for 10-15 minutes the solution was warmed to room temperature and stirred for a further 3.5 hrs. The mixture was then treated with saturated aqueous ammonium chloride solution (~2 ml) and subsequently diluted with dichloromethane (5 ml). The organic layer was separated by filtering through a hydrophobic frit (washing the aqueous with further aliquots of dichloromethane (2×5 ml)). Evaporation of the combined organic phases gave a brown oil (~0.100 g). This was purified by automated flash-silica column chromatography, eluting with a 0-100% gradient of ethyl acetate in hexane, to give partially purified (~90% pure) methyl 1-ethyl-5-oxo-4-(phenylmethyl)-prolinate (0.024 g) as a yellow oil which was used in the subsequent step without further purification.

(v) Methyl 1-ethyl-5-oxo-4-(phenylmethyl)-prolinate (0.024 g, 0.09 mmol) was dissolved in methanol (0.5 ml) and cooled to 0° C. in an ice-bath. 2M aqueous sodium hydroxide (0.137 ml, 0.27 mmol) was added to the mixture and stirring continued at 0° C. for 3 hrs. The solvent was evaporated and the residue was acidified by treatment with 2M aqueous hydrogen chloride (~0.2 ml) to give a cloudy solution. Evaporation then gave crude 1-ethyl-5-oxo-4-(phenylmethyl)-proline (0.052 g) as a mixture of white solids and yellow oily residues. This was used without further purification.

Alternatively 1-ethyl-5-oxo-4-(phenylmethyl)-proline could also be prepared in the following manner (Method B):

(i) (S)-(+)-L-5-trityloxymethyl-2-pyrrolidinone (1.88 g, 20 mmol) was dissolved in dimethylformamide (9 ml) at 0° C. and treated with sodium hydride (60% suspension in oil, 0.220 g, 5.5 mmol). The mixture was stirred at 0° C. for 30 mins and then treated with ethyl iodide (0.444 ml, 5.5 mmol). The mixture was allowed to warm to room temperature and then stirred overnight. The mixture was then partitioned between ethyl acetate and saturated aqueous ammonium chloride and extracted with ethyl acetate (×3). The combined organic extracts were washed sequentially with water, 50% aqueous sodium chloride solution (×2), and saturated aqueous sodium chloride solution, and then dried over sodium sulphate. Concentration gave a beige solid which was purified by automated flash silica-gel column chromatography (Biotage SP4), eluting with a 0-100% gradient of ethyl acetate in hexane, to give pure 1-ethyl-5-{[(triphenylmethyl)oxy]methyl}-2-pyrrolidinone (1.78 g).

(ii) A 2M solution of lithium diisopropylamine in tetrahydrofuran (1.050 ml, 2.1 mmol) was added, at –78° C., to a solution of 1-ethyl-5-{[(triphenylmethyl)oxy]methyl}-2-pyrrolidinone (0.771 g, 2 mmol) in tetrahydrofuran (10 ml) and the resulting mixture was stirred for 1 hr at –78° C. Benzyl bromide (0.262 ml, 2.2 mmol) was then added and after stirring for a further 1 hr at –78° C. the mixture was allowed to warm to room temperature overnight. The mixture was quenched with saturated aqueous ammonium chloride and then extracted with ethyl acetate (×3). The combined organic extracts were then washed with water and then with saturated aqueous sodium chloride solution (×2), dried over anhydrous magnesium sulphate, and concentrated to a crude oil (1.27 g). The crude solid was purified by automated flash silica-gel column chromatography (Biotage SP4), eluting with a 0-100% gradient of ethyl acetate in hexane, to give the desired product (i.e. 1-ethyl-3-(phenylmethyl)-5-{[(triphenylmethyl)oxy]methyl}-2-pyrrolidinone (0.561 g)) which was used in the next step, as well as unreacted starting material and the dialkylation product, 1-ethyl-3,3-bis(phenylmethyl)-5-{[(triphenylmethyl)oxy]methyl}-2-pyrrolidinone (0.053 g).

(iii) 1-Ethyl-3-(phenylmethyl)-5-{[(triphenylmethyl)oxy]methyl}-2-pyrrolidinone (0.561 g, 1.1 mmol) was stirred for 24 hrs at room temperature in a mixture of acetonitrile (21 ml) and formic acid (3 ml). The reaction was not complete at this stage so the solvent was evaporated and replaced with formic acid (10 ml) and stirring was continued for 3 hrs. Reaction was still not complete so the mixture was concentrated in vacuo (azeotroping with methanol to remove all of the formic acid) and then dissolved in methanol (20 ml). Amberlyst 15® was then added to the mixture and stirring was continued at room temperature overnight. The resin was filtered off, washing with more methanol, and the filtrate was concentrated to a gum (0.625 g). The gum was purified by automated flash silica-gel column chromatography (Biotage SP4), eluting with a 0-100% gradient of ethyl acetate in hexane, to give 1-ethyl-5-(hydroxymethyl)-3-(phenylmethyl)-2-pyrrolidinone (0.170 g) which was used in the next step.

(iv) 1-Ethyl-5-(hydroxymethyl)-3-(phenylmethyl)-2-pyrrolidinone (0.748 g, 3.21 mmol) was dissolved in acetonitrile (5 ml) and a 1M aqueous sodium phosphate monobasic buffer solution (3.69 ml, 3.69 mmol), a few crystals of TEMPO (2,2,6,6-tetramethyl-1-piperidinyloxy free radical), and sodium chlorite (0.580 g, 6.41 mmol) were added and the mixture was warmed to 40° C. Approximately 1 drop of bleach (sodium hypochlorite solution, available chlorine >12%) was then added to the mixture and stirring continued at 40° C. for 3 hrs. The mixture was then poured onto ice-water containing 1% w/w sodium sulphite and the resulting mixture was adjusted to pH2 using 5N aqueous hydrogen chloride and then extracted with ethyl acetate (×3). The combined organic extracts were washed with saturated aqueous sodium chloride and then dried over magnesium sulphate and concentrated to give 1-ethyl-5-oxo-4-(phenylmethyl)proline (0.807 g) as a solid which was used without additional purification.

Example 38

N-[(2-chloro-4-fluorophenyl)methyl]-1-(2-methyl-2-propen-1-yl)-5-oxoprolinamide (E38)

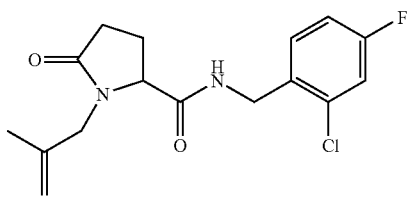

Crude 1-(2-methyl-2-propen-1-yl)-5-oxoproline (~0.075 g, ~0.41 mmol, prepared as described below) was dissolved in dichloromethane (5 ml) and to this was added 1-Hydroxybenzotriazole (0.061 g, 0.45 mmol), [(2-chloro-4-fluorophenyl)methyl]amine (0.068 g, 0.43 mmol), and N-(3-dimethylaminopropyl)-N'-ethylcarbodiimide hydrochloride (0.087 g, 0.45 mmol). The mixture was then stirred at room temperature for 24 hrs. The mixture was diluted with more dichloromethane then washed sequentially with 2M aqueous hydrogen chloride and saturated aqueous sodium hydrogen carbonate. The organic layer was filtered through a phase separator and evaporated to give a brown residue which was purified by mass-directed automated HPLC to give pure N-[(2-chloro-4-fluorophenyl)methyl]-1-(2-methyl-2-propen-1-yl)-5-oxoprolinamide (0.018 g) as a white solid. LC/MS [M+H]⁺=325.1, retention time=2.40 minutes.

The 1-(2-methyl-2-propen-1-yl)-5-oxoproline used in the above procedure was prepared as follows:

(i) Methanol (55 ml) was cooled to −10° C. (using a cardice/carbon tetrachloride bath) with stirring and then thionyl chloride was added dropwise over 45 minutes. (D)-glutamic acid (10 g, 67.96 mmol) was then added in three portions over ~5 minutes and then the reaction was stirred for 3 hrs whilst warming to 21° C. The solvents were evaporated in vacuo to give a clear oil (15 g) which was dissolved in a mixture of water (150 ml) and dioxane (150 ml). To this sodium carbonate (46 g, 340 mmol) was then slowly added with stirring. Benzyl chloroformate (9.64 ml, 68 mmol) was then added and stirring continued overnight. The mixture was cautiously treated with 2N aqueous hydrogen chloride (250 ml) and then extracted with ethyl acetate (2×250 ml). The combined organic fractions were washed with brine and then dried and evaporated to give a clear oil (18.7 g). This was dissolved in dichloromethane (400 ml) and treated with concentrated sulphuric acid (1 ml). A large excess of isobutylene was then condensed into the mixture and then stirred overnight at 21° C. Saturated aqueous sodium hydrogen carbonate (~400 ml) was then added carefully to the mixture and then the organic phase was separated, washed with brine, dried and evaporated in vacuo to give a clear oil (21.9 g). This was purified by silica gel column chromatography, eluting with a 3:1 mixture of cyclohexane and ethyl acetate, to give pure 1-(1,1-dimethylethyl) 5-methyl N-{[(phenylmethyl)oxy]carbonyl}glutamate (4.87 g).

(ii) To a solution of potassium hexamethyldisilazide (10 ml of a 0.6M solution in toluene, 6 mmol) in tetrahydrofuran (25 ml) at −70° C., was added dropwise a solution of 1-(1,1-dimethylethyl) 5-methyl N-{[(phenylmethyl)oxy]carbonyl}glutamate (1.05 g, 3 mmol) in tetrahydrofuran (10 ml) over ~5 minutes. The mixture was stirred at −70° C. for 1 hr and then treated with methallyl iodide (2.18 g, 12 mmol) in tetrahydrofuran (10 ml). Stirring was continued at −78° C. for 2 hrs and then warmed to 21° C. After stirring for a further 1 hr the mixture was poured into 1N aqueous hydrogen chloride and extracted with ethyl acetate (2×50 ml). The combined organics were washed with brine, dried, and evaporated in vacuo, to give a yellow oil (1.03 g). This was purified by silica column chromatography, eluting with a 4:1 mixture of cyclohexane and ethyl acetate, to give pure 1,1-dimethylethyl 1-(2-methyl-2-propen-1-yl)-5-oxoprolinate as a clear oil (0.322 g).

(iii) 1,1-dimethylethyl 1-(2-methyl-2-propen-1-yl)-5-oxoprolinate (0.099 g, 0.41 mmol) was dissolved in a mixture of dichloromethane (2 ml) and trifluoroacetic acid (2 ml) and stirred overnight at room temperature. The solvent was evaporated (azeotroping with toluene to remove traces of trifluoroacetic acid) to give crude 1-(2-methyl-2-propen-1-yl)-5-oxoproline as a brown oil which was used without further purification.

Example 39

1-Cyclopropyl-N-[(2,4-dichlorophenyl)methyl]-5-oxoprolinamide (E39)

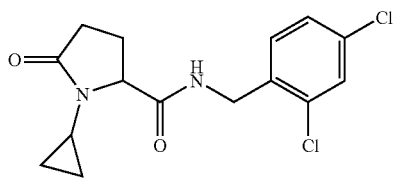

To a solution of (2,4-dichlorophenyl)methyl isocyanide (0.047 g, 0.25 mmol) and 4-oxobutanoic acid (15% in water, 0.26 ml, 0.4 mmol) in methanol (1.75 ml) was added cyclopropylamine (0.042 ml, 0.6 mmol). The mixture was heated to 100° C. for 30 minutes in a microwave reactor. The solvent was removed in vacuo and the residue was purified by mass-directed automated HPLC to give 1-Cyclopropyl-N-[(2,4- dichlorophenyl)methyl]-5-oxoprolinamide (0.072 g) as a white solid. LC/MS [M+H]$^+$=326/328, retention time=2.29 minutes.

Example 40

N-{[2-Chloro-3-(trifluoromethyl)phenyl]methyl}-1-cyclopropyl-5-oxoprolinamide (E40)

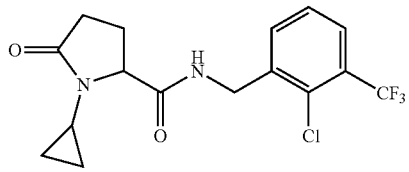

To a solution of [2-chloro-3-(trifluoromethyl)phenyl]methyl isocyanide (0.088 g, 0.4 mmol) and succinic semialdehyde (15% in water, 0.26 ml, 0.4 mmol) in methanol (1.75 ml) was added cyclopropylamine (0.042 ml, 0.6 mmol). The mixture was heated to 100° C. for 30 minutes in a microwave reactor. The solvent was removed in vacuo and the residue was purified by mass-directed automated HPLC to give N-{[2-Chloro-3-(trifluoromethyl)phenyl]methyl}-1-cyclopropyl-5-oxoprolinamide (0.076 g) as a white solid. LC/MS [M+H]$^+$=361/363, retention time=2.39 minutes.

The [2-chloro-3-(trifluoromethyl)phenyl]methyl isocyanide used in the above procedure was prepared as follows:

(i) A solution of {[2-chloro-3-(trifluoromethyl)phenyl]methyl}amine (1.05 g, 5 mmol) in anhydrous tetrahydrofuran (10 ml) was added dropwise to a solution of N-formyl benzotriazole (0.772 g, 5.25 mmol) in anhydrous tetrahydrofuran (10 ml). The reaction was stirred at 22° C. for 18 hrs then reduced in vacuo and the residue partitioned between dichloromethane (75 ml) and 2N aqueous sodium hydroxide (40 ml). The organic layer was separated and extracted with 2N aqueous sodium hydroxide (40 ml). The organic layer was passed through a hydrophobic frit and reduced in vacuo to give a white solid. The crude product was purified by automated flash silica column chromatography (Biotage SP4), eluting with a solvent gradient of 0-10% ethyl acetate in dichloromethane, to give {[2-chloro-3-(trifluoromethyl)phenyl]methyl}formamide as a white solid.

(ii) A solution of {[2-chloro-3-(trifluoromethyl)phenyl]methyl}formamide (0.67 g, 2.82 mmol) in anhydrous dichloromethane (20 ml) was cooled under argon in an ice-water bath before the addition of diisopropylamine (1.78 ml, 12.7 mmol) followed by phosphorus oxychloride (0.393 ml, 4.23 mmol). The reaction was stirred at between 2-5° C. for 2 hrs. The mixture was then reduced in vacuo and the residue treated with saturated aqueous sodium hydrogen carbonate (20 ml) and extracted with dichloromethane (20 ml). The organic layer was passed through a hydrophobic frit and the reduced in vacuo to give a yellow solid. Further drying in vacuo gave [2-chloro-3-(trifluoromethyl)phenyl]methyl isocyanide as an orange gum (0.66 g) which was used without further purification.

Example 41

N-[(2-chloro-4-fluorophenyl)methyl]-1-cyclopropyl-5-oxoprolinamide (E41)

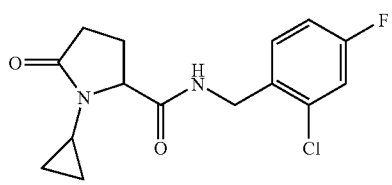

To a solution of [2-chloro-4-fluoro-phenyl]methyl isocyanide (0.068 g, 0.4 mmol) and succinic semialdehyde (15% in water, 0.26 ml, 0.4 mmol) in methanol (1.75 ml) was added cyclopropylamine (0.042 ml, 0.6 mmol). The mixture was heated to 100° C. for 30 minutes in a microwave reactor. The solvent was removed in vacuo and the residue was purified by mass-directed automated HPLC to give a colourless gum which was triturated with diethyl ether to give N-[(2-chloro-4-fluorophenyl)methyl]-1-cyclopropyl-5-oxoprolinamide as a pale cream solid (0.058 g). LC/MS [M+H]$^+$=310, retention time=2.16 minutes.

The [2-chloro-4-fluoro-phenyl]methyl isocyanide used as the starting material was prepared in an analogous manner to that described for the preparation of [2-chloro-3-(trifluoromethyl)phenyl]methyl isocyanide in example 40 but using 2-chloro-4-fluorophenyl]methyl}amine in the place of 2-chloro-3-(trifluoromethyl)phenyl]methyl}amine.

Example 42

N-[(2,4-dichlorophenyl)methyl]-1-ethyl-4,4-dimethyl-5-oxoprolinamide (E42)

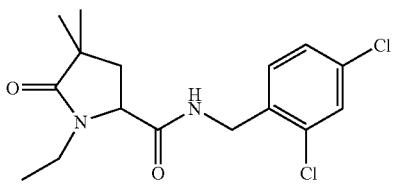

(2,4-Dichlorophenyl)methyl isocyanide (0.075 g, 0.4 mmol) and crude 2,2-dimethyl-4-oxobutanoic acid (0.115 g, 0.6 mmol) were dissolved in methanol (2 ml). Ethylamine solution (2M in water, 0.3 ml, 0.6 mmol) was added and the mixture was heated in a sealed vessel at 100° C. for 30 minutes in a microwave reactor. The mixture was left to stand over the weekend and then the solvent was removed in vacuo and the resulting orange oil was purified by mass-directed automated HPLC to give a clear oily gum which was triturated with diethyl ether to give N-[(2,4-dichlorophenyl)methyl]-1-ethyl-4,4-dimethyl-5-oxoprolinamide as a white solid (0.024 g). LC/MS [M+H]$^+$=343, retention time=2.57 minutes.

The 2,2-dimethyl-4-oxobutanoic acid used as the starting material in the above procedure was prepared as follows:

(i) 2,2-dimethyl-4-pentenoic acid was dissolved in dichloromethane (25 ml) and cooled to −78° C. in a CO$_2$/acetone bath and oxygen was bubbled through the mixture for 5 minutes. The ozone generator was switched on and ozone was bubbled through the mixture for 15 minutes. The flow of ozone was then stopped and the mixture was flushed with oxygen for 5 minutes and then with argon for 2 minutes. TLC indicated that the reaction had not progressed significantly so ozone was bubbled through the mixture for a further 15 minutes after which time a pale blue colour persisted and a suspension had formed. The ozone flow was switched off and the mixture was flushed with oxygen for 5 minutes and then with argon for 10 minutes (until the exhaust gas gave a negative response to wetted starch/iodine paper). Dimethyl sulphide (1.72 ml, 23.41 mmol) was then added to the mixture and the mixture was allowed to warm to room temperature. After stirring at room temperature for 2 hrs the mixture was concentrated to give a colourless oil (1.5 g). 1.4 g of this material was purified by flash silica column chromatography, eluting with a gradient of 0-50% ethyl acetate in dichloromethane, to give 2,2-dimethyl-4-oxobutanoic acid as a colourless oil (0.649 g).

Example 43

N-{[2-chloro-3-(trifluoromethyl)phenyl]methyl}-1-(1-methylethyl)-5-oxoprolinamide (E43)

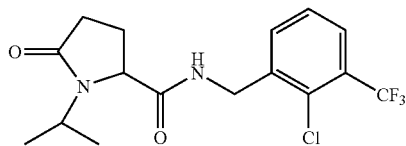

1-(1-Methylethyl)-5-oxoproline (0.100 g, 0.58 mmol) was dissolved in dichloromethane (20 ml) and to this was added N-(3-dimethylaminopropyl)-N'-ethylcarbodiimide hydrochloride (0.111 g, 0.58 mmol), 1-Hydroxybenzotriazole (0.078 g, 0.58 mmol), and N-ethyl morpholine (0.223 ml, 1.75 mmol). Finally {[2-chloro-3-(trifluoromethyl)phenyl]methyl}amine was added to the mixture and stirring continued for ~48 hrs. The mixture was then treated with saturated aqueous sodium hydrogen carbonate (20 ml) and stirred vigorously. The aqueous layer was removed using a phase separator and then the solvent was removed from the organic layer using an argon blow-down unit. The resulting residue was treated with a mixture of water and ethylacetate (25 ml, 1:1) and the aqueous layer was subsequently discarded. The organic layer was filtered through a phase separator and evaporated to give an oil. This was triturated with diethyl ether to give a solid and this was subsequently purified by mass-directed automated HPLC to give N-{[2-chloro-3-(trifluoromethyl)phenyl]methyl}-1-(1-methylethyl)-5-oxoprolinamide (0.097 g) as a white solid. LC/MS $[M+H]^+=363$, retention time=2.48 minutes.

The 1-(1-Methylethyl)-5-oxoproline used in the above procedure was prepared in an analogous manner to that described previously for the synthesis of methyl 1-ethyl-5-oxo-prolinate (see example 3) but using acetone in the place of acetaldehyde and with the addition of a subsequent ester deprotection step (using standard conditions, i.e. sodium hydroxide in methanol) being carried out (as opposed to the combined deprotection and amide coupling described in example 3).

Examples 44-49

In a manner analogous to that described for Example 43 above the compounds tabulated below (Table 3) were prepared by substituting the appropriate amine (or salt thereof) for the {[2-chloro-3-(trifluoromethyl)phenyl]methyl}amine used in the above procedure. All of the amines used to make the compounds shown in Table 3 are available from commercial sources or can be prepared using routes described previously in the chemical literature unless stated otherwise.

TABLE 3

| Example no. | Chemical name | $[M + H]^+$ | Retention time (mins) |
|---|---|---|---|
| E44 | 1-(1-methylethyl)-N-{[2-methyl-3-(trifluoromethyl)phenyl]methyl}-5-oxoprolinamide | 343 | 2.48 |
| E45 | N-[(2,3-dichlorophenyl)methyl]-1-(1-methylethyl)-5-oxoprolinamide | 329 | 2.35 |

TABLE 3-continued

| Example no. | Chemical name | [M + H]⁺ | Retention time (mins) |
|---|---|---|---|
| E46 | 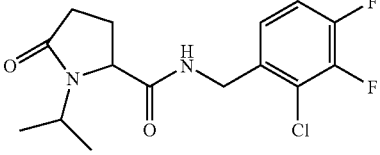 N-[(2-chloro-3,4-difluorophenyl)methyl]-1-(1-methylethyl)-5-oxoprolinamide | 331 | 2.26 |
| E47 | 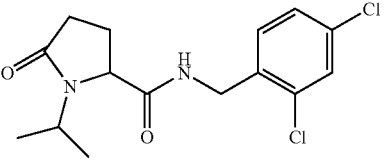 N-[(2,4-dichlorophenyl)methyl]-1-(1-methylethyl)-5-oxoprolinamide | 329 | 2.4 |
| E48 | 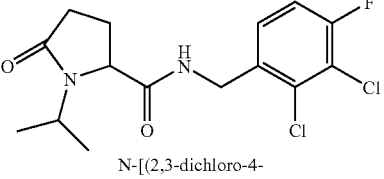 N-[(2,3-dichloro-4-fluorophenyl)methyl]-1-(1-methylethyl)-5-oxo-L-prolinamide | 346.9 | 2.41 |
| E49 | 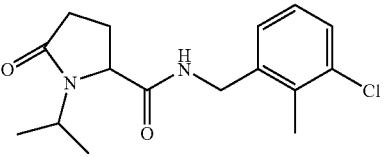 N-[(3-chloro-2-methylphenyl)methyl]-1-(1-methylethyl)-5-oxoprolinamide | 309 | 2.34 |

The [(2,3-dichloro-4-fluorophenyl)methyl]amine hydrochloride required for the synthesis of N-[(2,3-dichloro-4-fluorophenyl)methyl]-1-(1-methylethyl)-5-oxo-L-prolinamide (example 48) was prepared in the following manner:

(i) Sodium nitrite (0.172 g, 2.5 mmol) was added to a stirred solution of 2-chloro-6-fluoro-3-methyl-phenylamine (0.400 g, 2.5 mmol) in water (20 ml) and 37% aqueous hydrogen chloride (5 ml) at −5° C. The mixture was stirred at −5° C. for 5 minutes and then added in one pot to a solution of copper (I) chloride (0.742 g, 7.5 mmol) in 37% aqueous hydrogen chloride (5 ml) whilst maintaining the temperature at −5 to 0° C. The reaction mixture was heated to 38° C. and stirred for 1 hr then the mixture was cooled and diethyl ether (20 ml) was added. The organic phase was separated and washed with 1N aqueous hydrogen chloride and then with water. The organic layer was then dried over sodium sulphate and concentrated in vacuo. The crude residue was purified by flash silica column chromatography, eluting with petroleum ether, to give 2,3-dichloro-1-fluoro-4-methylbenzene (0.090 g, 0.5 mmol) as a white solid.

(ii) 2,3-dichloro-1-fluoro-4-methylbenzene (0.090 g, 0.5 mmol) was added to a stirred mixture of potassium dichromate (0.284 g, 1 mmol) in acetic acid (1 ml). 97% Sulphuric acid (0.5 ml) was then added slowly to the mixture which was subsequently heated at 100° C. for 2 hrs. After cooling to room temperature, water and ice were added and the green solid thus obtained was filtered off and washed with cold water to afford 2,3-dichloro-4-fluorobenzoic acid (0.056 g, 0.27 mmol) as a white solid.

(iii) A solution of 2,3-dichloro-4-fluorobenzoic acid (0.200 g, 0.92 mmol) in dichloromethane (~4 ml) was treated with 1-hydroxybenzotriazole (0.162 g, 1.2 mmol), N-(3-dimethylaminopropyl)-N'-ethylcarbodiimide hydrochloride (0.230 g, 1.2 mmol), and triethylamine (0.56 ml, 4.0 mmol) under argon at room temperature. The mixture was stirred at room temperature for 40 minutes then treated with) 32% aqueous ammonium hydroxide (0.088 ml) and stirred overnight at room temperature. The mixture was diluted with dichloromethane and washed sequentially with water and then with saturated aqueous sodium hydrogen carbonate. The organic layer was separated and dried over sodium sulphate then concentrated to give 2,3-dichloro-4-fluorobenzamide (0.156 g) as a white solid that was used without further purification.

(iv) A solution of 2,3-dichloro-4-fluorobenzamide (0.750 g, 3.62 mmol) in dry tetrahydrofuran (2 ml) was heated to 90° C. under nitrogen. A 10M solution of boron hydride dimethyl sulphide complex in tetrahydrofuran (1.05 ml, 5.43 mmol) was added to the hot solution and stirring was continued for 4 hrs. The mixture was then treated with 6N aqueous hydrogen chloride and heating continued for 30 minutes. The solvents were evaporated and the crude residue was purified by SCX cartridge and subsequent flash silica column chromatography eluting with 5% methanol in dichloromethane. The amine obtained was treated with ethereal hydrogen chloride to give [(2,3-dichloro-4-fluorophenyl)methyl]amine hydrogen chloride (0.360 g) as a white solid.

Example 50

N-[(2,3-dimethylphenyl)methyl]-1-ethyl-5-oxoprolinamide (E50)

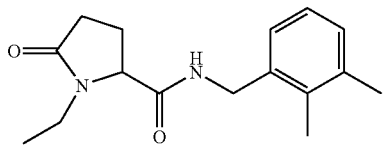

1-ethyl-5-oxoproline (0.080 g, 0.51 mmol, prepared in an analogous manner to that described for example 12, method A) was dissolved in dichloromethane (5 ml) and to this was added N-(3-dimethylaminopropyl)-N'-ethylcarbodiimide hydrochloride (0.117 g, 0.61 mmol), N-ethyl morpholine (0.195 ml, 1.53 mmol), and 2,3-dimethyl benzylamine (0.082 g, 0.61 mmol). The mixture was stirred for ~17 hrs and then left to stand over the weekend. The mixture was then treated with saturated aqueous sodium hydrogen carbonate (~3 ml) and stirred vigorously for ~10 minutes. The organic layer was separated using a hydrophobic frit and the aqueous layer was extracted with more dichloromethane (~2 ml). The combined organic layers were concentrated to give a yellow oil (~0.2 g). This was purified further by mass-directed automated HPLC to give pure N-[(2,3-dimethylphenyl)methyl]-1-ethyl-5-oxoprolinamide (0.072 g) as white solid.

LC/MS [M+H]$^+$=275, retention time=2.12 minutes.

Example 51

N-{[2-chloro-3-(trifluoromethyl)phenyl]methyl}-1-methyl-5-oxoprolinamide

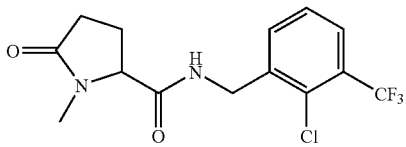

1-methyl-5-oxoproline (2.27 g, 15.88 mmol, prepared as described below) was dissolved in dichloromethane (150 ml) and to this was added N-(3-dimethylaminopropyl)-N'-ethylcarbodiimide hydrochloride (3.35 g, 17.47 mmol), and 1-hydroxybenzotriazole (2.36 g, 17.47 mmol). The mixture was stirred for ~10 minutes and then triethylamine (2.21 ml, 15.88 mmol) and {[2-chloro-3-(trifluoromethyl)phenyl]methyl}amine (3.66 ml, 17.47 mmol) were added and the mixture was left stirring at room temperature overnight (~17 hrs). A white precipitate formed during this time. The mixture was then treated with saturated aqueous sodium hydrogen carbonate (~100 ml) and stirred for 10 minutes. The organic layer was separated using a hydrophobic frit and then 2N aqueous hydrogen chloride was added and mixed and separated again. The organic layer was concentrated to give white solids (~2.5 g). The solid was dissolved in ethyl acetate (~200 ml) and washed with water (4×50 ml) followed by brine (50 ml). The organic layer was then dried by passing through a phase separator and concentrated to give pure N-{[2-chloro-3-(trifluoromethyl)phenyl]methyl}-1-methyl-5-oxo-L-prolinamide as a fine white solid (2.48 g).

LC/MS [M+H]$^+$=335, retention time=2.24 minutes.

$^1$H NMR (CDCl$_3$, 500 MHz) δ 2.02 (m, 1H), 2.35 (m, 1H), 2.39 (m, 1H), 2.47 (m, 1H), 2.81 (s, 3H), 4.00 (dd, 1H, J=8.9, 4.2 Hz), 4.60 (dd, 1H, J=15.1, 6.2 Hz), 4.65 (dd, 1H, J=15.1, 6.2 Hz), 6.56 (broad t, 1H, J=5.8 Hz), 7.38 (t, 1H, J=7.7 Hz), 7.60 (dd, 1H, J=7.6, 1.0 Hz), 7.68 (dd, 1H, J=7.9, 1.2 Hz); $^{13}$C NMR δ 176.0, 171.5, 137.5, 133.9, 131.7, 129.3, 127.4, 127.0, 122.8, 63.8, 41.8, 29.4, 29.2, 23.4.

The 1-methyl-5-oxoproline used as the starting material was prepared in the following manner:

(i) N-methyl-L-glutamic acid (9.81 g, 60.87 mmol) was split into two equal batches and each was suspended in water (15 ml) and heated in a sealed tube at 140° C. for 30 minutes in a microwave reactor to give a clear solution. The two batches were then combined and the water was evaporated and dried under vacuum to give a white solid. The solid was triturated with ether then filtered and washed with more ether to give, after drying, 1-methyl-5-oxo-proline (7.47 g) as a white solid.

N-{[2-chloro-3-(trifluoromethyl)phenyl]methyl}-1-methyl-5-oxoprolinamide may also be prepared as described below:

1-Methyl-5-oxoproline (49.0 g, 0.342 mol, prepared as described above) was suspended in DCM (600 ml) (internal temperature drops from 20° C. to 13.7° C.). EEDQ (2-ethoxy-1-ethoxycarbonyl-1,2-dihydroquinoline, 75.26 g, 0.359 mol, 1.05 eq) was added in one portion and the mixture was stirred at room temperature for 15 minutes. A solution of 1-[2-chloro-3-(trifluoromethyl)phenyl]methanamine (88.77 g, 0.359 mol, 1.05 eq) in DCM (250 ml) was then added dropwise to the mixture over 20 minutes (slight exotherm to 19° C.) and any remaining solids were then washed into the mixture using additional DCM (150 ml). The mixture was then stirred at room temperature overnight.

Saturated aqueous sodium hydrogen carbonate (300 ml) was added and the mixture was stirred for 5 minutes at room temperature. The organic layer was separated, and washed sequentially with water (300 ml), 2N aqueous hydrogen chloride (3×300 ml), water (300 ml) and saturated aqueous sodium chloride solution (300 ml). The organic solution was dried over anhydrous sodium sulphate, filtered and evaporated in vacuo. The resulting solid was then triturated with ether (~500 ml) and the solid was collected, washed with ether and dried (30° C., vac oven over the weekend) to give a colourless solid (91.1 g, 80%). This material was combined with a similar batch, prepared in an analagous manner, and the combined material (total of 178 g) was dissolved in ethyl acetate (2.75 l) with heating (gentle reflux, overhead stirring). The resulting hot clear solution was gently stirred and cooled to room temperature overnight. The solid was collected, washed with cold ethyl acetate (500 ml) and dried (50° C. in vacuum oven, ~3 days) to give N-{[2-chloro-3-(trifluoromethyl)phenyl]methyl}-1-methyl-5-oxoprolinamide, as colourless needles (148.4 g).

LC/MS [M+H]$^+$=335/337, retention time=2.26 minutes.

$^1$H NMR (CDCl$_3$, 500 MHz) δ 1.86 (m, 1H), 2.21 (m, 1H), 2.24 (m, 1H), 2.28 (m, 1H), 2.64 (s, 3H), 4.12 (dd, 1H, J=8.3, 3.5 Hz), 4.47 (d, 2H, J=5.8 Hz), 7.58 (t, 1H, J=7.8 Hz), 7.65

(dd, 1H, J=7.8, 1.0 Hz), 7.80 (dd, 1H, J=7.8, 1.2 Hz), 8.81 (broad t, 1H, J=5.7 Hz); $^{13}$C NMR δ 174.4, 171.4, 138.8, 133.1, 129.8, 127.5, 127.1, 126.6, 122.9, 61.6, 40.2, 29.1, 28.0, 22.5.

Enantiomeric excess=99.1%, as determined by chiral chromatography method A, indicative of N-{[2-chloro-3-(trifluoromethyl)phenyl]methyl}-1-methyl-5-oxo-L-prolinamide retention time=6.99 minutes $[\alpha]_D$=−0.8° (c=1, MeOH), Temperature=29.3° C., wavelength=589 nm melting point=173° C.

Example 52

N-[(2,3-dichloro-4-fluorophenyl)methyl]-1-methyl-5-oxoprolinamide (E52)

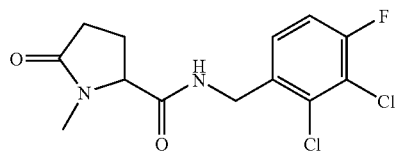

1-methyl-5-oxoproline (0.060 g, 0.42 mmol, prepared as described above for example 51) was dissolved in dichloromethane (5 ml) and to this was added N-(3-dimethylaminopropyl)-N'-ethylcarbodiimide hydrochloride (0.096 g, 0.5 mmol), 1-hydroxybenzotriazole (0.068 g, 0.5 mmol), and N-ethyl morpholine (0.160 ml, 1.26 mmol). The mixture was stirred for ~10 minutes and then [(2,3-dichloro-4-fluorophenyl)methyl]amine hydrochloride (0.081 g, 0.42 mmol, prepared as described previously for example 48) was added and the mixture was left to stir overnight (~17 hrs) and then over the weekend. The mixture was then treated with saturated aqueous sodium hydrogen carbonate (~3 ml) and stirred vigorously for 10 minutes. The organic layer was separated using a hydrophobic frit, washing the aqueous with additional dichloromethane (~2 ml). The combined organic fractions were concentrated to give a cream coloured solid. The solid was partitioned between ethyl acetate (~20 ml) and water (~10 ml) and the organic layer was then separated by passing through a phase separator and concentrated to give pure -[(2,3-dichloro-4-fluorophenyl)methyl]-1-methyl-5-oxoprolinamide as an off-white solid.

LC/MS [M+H]$^+$=319, retention time=2.2 minutes.

Examples 53-64

In a manner analogous to that described for Example 52 above the compounds tabulated below (Table 4) were prepared by substituting the appropriate amine (or salt thereof) for the [(2,3-dichloro-4-fluorophenyl)methyl]amine hydrochloride used in the above procedure. All of the amines used to make the compounds shown in Table 4 are available from commercial sources or can be prepared using routes described previously in the chemical literature or using analogous methods.

TABLE 4

| Example no. | Chemical name | [M + H]$^+$ | Retention time (mins) |
|---|---|---|---|
| E53 | N-[(2-chloro-3,4-difluorophenyl)methyl]-1-methyl-5-oxoprolinamide | 303 | 2.04 |
| E54 | N-[(4-chloro-2-methylphenyl)methyl]-1-methyl-5-oxoprolinamide | 281 | 2.29 |
| E55 | N-{[4-fluoro-2-(trifluoromethyl)phenyl]methyl}-1-methyl-5-oxoprolinamide | 319 | 2.29 |

TABLE 4-continued

| Example no. | Chemical name | [M + H]+ | Retention time (mins) |
|---|---|---|---|
| E56 | <br>N-[(2,3-dichlorophenyl)methyl]-1-methyl-5-oxoprolinamide | 301 | 2.28 |
| E57 | 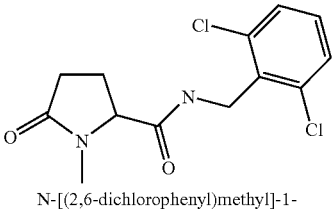<br>N-[(2,6-dichlorophenyl)methyl]-1-methyl-5-oxoprolinamide | 301 | 2.15 |
| E58 | 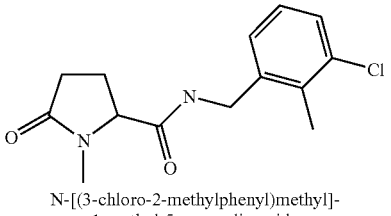<br>N-[(3-chloro-2-methylphenyl)methyl]-1-methyl-5-oxoprolinamide | 281 | 2.27 |
| E59 | 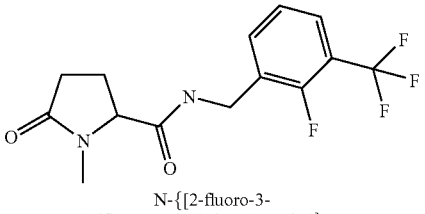<br>N-{[2-fluoro-3-(trifluoromethyl)phenyl]methyl}-1-methyl-5-oxoprolinamide | 319 | 2.32 |
| E60 | 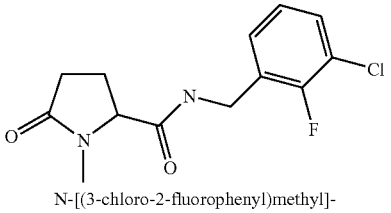<br>N-[(3-chloro-2-fluorophenyl)methyl]-1-methyl-5-oxoprolinamide | 285 | 2.14 |
| E61 | 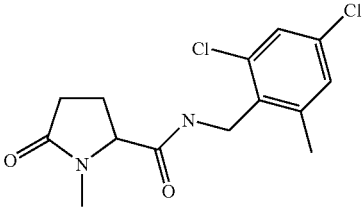<br>N-[(2,4-dichloro-6-methylphenyl)methyl]-1-methyl-5-oxoprolinamide | 315 | 2.3 |

TABLE 4-continued

| Example no. | Chemical name | [M + H]+ | Retention time (mins) |
|---|---|---|---|
| E62 | 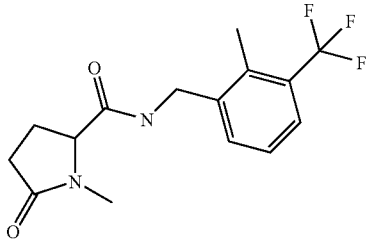<br>1-methyl-N-{[2-methyl-3-(trifluoromethyl)phenyl]methyl}-5-oxoprolinamide | 315.1 | 2.26 |
| E63 | 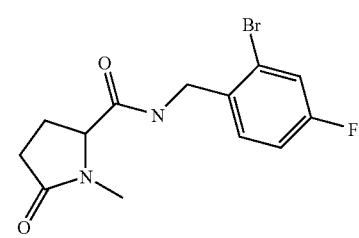<br>N-[(2-bromo-4-fluorophenyl)methyl]-1-methyl-5-oxoprolinamide | 330.9 | 2.0 |
| E64 | 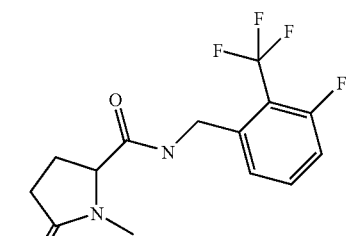<br>N-{[3-fluoro-2-(trifluoromethyl)phenyl]methyl}-1-methyl-5-oxoprolinamide | 319 | 2.1 |

The amines required for the synthesis of example 62-64 were prepared according to the procedures described, respectively, below:

1) {[2-Methyl-3-(trifluoromethyl)phenyl]methyl}amine hydrochloride (Amine Used to Prepare Example 62)

Borane tetrahydrofuran (1M, 39.4 ml, 39.4 mmol) was added to a solution of 2-methyl-3-trifluoromethyl benzamide (2 g, 9.85 mmol) in tetrahydrofuran (75 ml) and stirred at 70° C. for 5 hrs. LCMS showed incomplete reaction so heating at 70° C. under argon was continued overnight and then for a further 5 hrs following this. The reaction mixture was treated with 2N aqueous hydrogen chloride and stirred at 100° C. for 4 hrs and then left to cool over the weekend. The mixture was reduced to dryness undervacuum and then partitioned between dichloromethane and 2N aqueous sodium hydroxide. The organic layer was separated using a hydrophobic frit and reduced to give a residue which was purified by flash silica column chromatography (eluting with 0-5% 2N ammonia/methanol in dichloromethane). The solvent was evaporated and the residue taken up in diethyl ether and treated with 1M ethereal hydrogen chloride. The solid that precipitated was collected by filtration and this was then triturated with dichloromethane and after filtration 2-Methyl-3-(trifluoromethyl)phenyl]methyl}amine hydrochloride (1.4 g) was obtained as a white solid.

LC/MS [M+H]+=173, retention time=1.30 minutes.

2) [(2-bromo-4-fluorophenyl)methyl]amine hydrochloride (Amine Used to Prepare Example 63)

(i) 2-Bromo-4-fluorobenzyl bromide (5 g 18.8 mmol) and potassium phthalimide (4 g, 21.6 mmol) were combined in dimethylformamide (200 ml) and stirred at 80° C. for 18 hrs overnight. The mixture was reduced under vacuum and the residue was partitioned between diethyl ether and water. Solids were filtered off and the aqueous layer was washed with more ether (2×50 ml). The ether layers were combined and dried over sodium sulphate then filtered and evaporated to give an off-white solid (3.36 g). The solid was triturated with methanol and filtration gave 2-[(2-bromo-4-fluorophenyl) methyl]-1H-isoindole-1,3(2H)-dione as a solid (2.06 g) which was used without further purification in the next step.

LC/MS [M+H]+=334, retention time=3.30 minutes.

(ii) Hydrazine hydrate (0.655 ml, 21 mmol) was added to a suspension of 2-[(2-bromo-4-fluorophenyl)methyl]-1H-isoindole-1,3(2H)-dione (2 g, 6 mmol) in ethanol (60 ml) and stirred at room temperature overnight. The reaction had not gone to completion at this stage so the mixture was heated at 100° C. for a total of 2 hrs (the mixture turned white and cloudy during this time). The mixture was filtered to remove solids then cooled and filtered again. The solids were washed with cold ethanol and then the combined ethanol fractions were evaporated to dryness under vacuum. The resulting residue was partitioned between 2N aqueous hydrogen chloride and dichloromethane. The organic phase was separated using a hydrophobic frit. The aqueous layer was washed with more dichloromethane and separated again. The aqueous layer was then reduced under vacuum to leave a pale yellow solid (0.876 g). The solid was taken up in saturated aqueous sodium hydrogen carbonate solution and extracted with dichloromethane. Separation by hydrophobic frit and evaporation gave a residue which was dissolved in diethyl ether and treated with ethereal hydrogen chloride. A pale yellow solid precipitated from the mixture. Evaporation and drying gave [(2-bromo-4-fluorophenyl)methyl]amine hydrochloride (0.789 g).

LC/MS [M+H]$^+$=203, retention time=1.08 minutes.

3) {[3-fluoro-2-(trifluoromethyl)phenyl]methyl}amine hydrochloride (Amine Used to Prepare Example 64)

Borane tetrahydrofuran (1M, 19.2 ml, 19.2 mmol) was added dropwise to a solution of 3-fluoro-2-(trifluoromethyl) benzamide (1 g, 4.8 mmol) in tetrahydrofuran (40 ml) under argon at room temperature. The mixture was heated at 70° C. and then a further aliquot of borane tetrahydrofuran (10 ml, 10 mmol) was added and heating at 70° C. was continued over the weekend. The reaction mixture was cooled to room temperature and then treated with 2M aqueous hydrogen chloride (15 ml) and stirred at room temperature for 15 minutes. Aqueous sodium hydroxide solution was added until the pH of the mixture was between 8-9 and then the mixture was extracted with ethyl acetate (3×30 ml). The combined organic layers were filtered through a hydrophobic frit and then evaporated under vacuum. The residue was redissolved in dichloromethane, filtered through a hydrophobic frit and evaporated to give a yellow oil. The oil was dissolved in 2M aqueous hydrogen chloride. A white precipitate formed and this was collected by vacuum filtration and then loaded equally onto 4×10 g SCX columns. The columns were flushed with methanol and water and then aqueous ammonia was used to wash off the product. These latter fractions were reduced under vacuum to give a yellow oil (0.4 g). The oil was dissolved in diethyl ether and treated with 1M ethereal hydrogen chloride until no more precipitate formed. The mixture was reduced under vacuum to give {[3-fluoro-2-(trifluoromethyl)phenyl] methyl}amine hydrochloride as a white solid.

LC/MS [M+H]$^+$=193, retention time=1.15 minutes.

Examples 65-69

The examples tabulated below (Table 5) were prepared in a manner analogous to that described for Example 12 by substituting the appropriate amine (or salt thereof) for the [(2,3, 4-trifluorophenyl)methyl]amine used in the procedure described for example 12. All of the amines used to make the compounds shown in Table 5 are available from commercial sources or can be prepared using routes described previously in the chemical literature unless stated otherwise. The 1-ethyl-5-oxo-proline used to prepare these examples was in turn prepared using method C as described for example 12 apart from in the case of example 65 where method A was used.

TABLE 5

| Example no. | Chemical name | [M + H]$^+$ | Retention time (mins) |
|---|---|---|---|
| E65 | 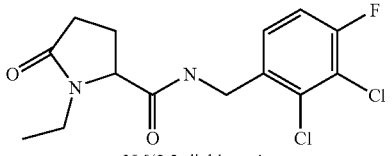<br>N-[(2,3-dichloro-4-fluorophenyl)methyl]-1-ethyl-5-oxoprolinamide | 333 | 2.31 |
| E66 | 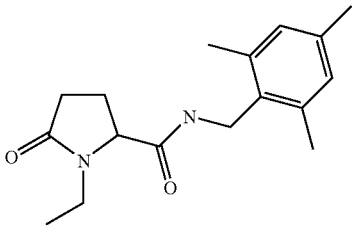<br>1-ethyl-5-oxo-N-[(2,4,6-trimethylphenyl)methyl]-prolinamide | 288 | 2.41 |
| E67 | 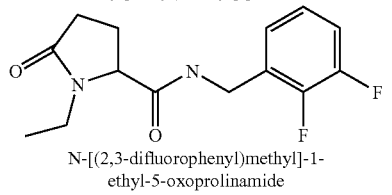<br>N-[(2,3-difluorophenyl)methyl]-1-ethyl-5-oxoprolinamide | 283 | 1.96 |

TABLE 5-continued

| Example no. | Chemical name | [M + H]⁺ | Retention time (mins) |
|---|---|---|---|
| E68 | 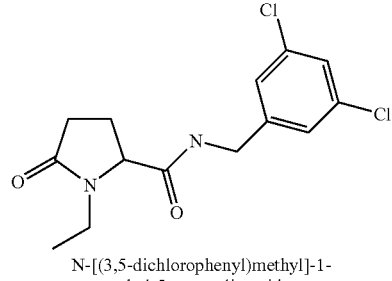<br>N-[(3,5-dichlorophenyl)methyl]-1-ethyl-5-oxoprolinamide | 315 | 2.39 |
| E69 | 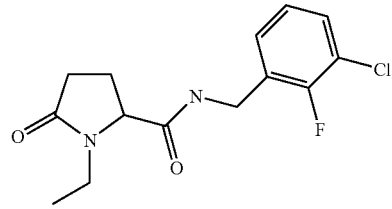<br>N-[(3-chloro-2-fluorophenyl)methyl]-1-ethyl-5-oxoprolinamide | 299 | 2.22 |

Example 70

N-[(2-chloro-4-fluorophenyl)methyl]-1-ethyl-5-oxoprolinamide (E70)

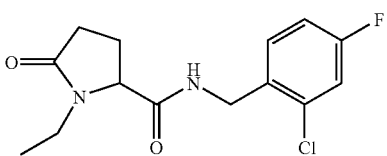

1-ethyl-5-oxoproline (0.100 g, 0.64 mmol) was dissolved in a mixture of dichloromethane (3 ml) and dimethylformamide (0.5 ml) and to this was added N-(3-dimethylaminopropyl)-N'-ethylcarbodiimide hydrochloride (0.147 g, 0.77 mmol), 1-hydroxybenzotriazole (0.104 g, 0.77 mmol), and N-ethyl morpholine (0.244 ml, 1.92 mmol). The mixture was stirred for 10 minutes and then 2-chloro-4-fluorobenzylamine was added to the mixture and stirring continued overnight (~16 hrs) at room temperature. The mixture was then treated with saturated aqueous sodium hydrogen carbonate (~2 ml) and stirred vigorously for ~10 minutes. The aqueous layer was removed using a phase separator and extracted with more dichloromethane (2×1 ml). The combined organic layers were concentrated to give a yellow oil and this was subsequently purified by mass-directed automated HPLC to give N-[(2-chloro-4-fluorophenyl)methyl]-1-ethyl-5-oxo-D-prolinamide (0.065 g) as a white solid. LC/MS [M+H]⁺=299, retention time=2.16 minutes.

Enantiomeric excess=80.9%, as determined by chiral chromatography method B, indicative of N-[(2-chloro-4-fluorophenyl)methyl]-1-ethyl-5-oxo-D-prolinamide retention time=5.91 minutes The 1-ethyl-5-oxoproline used in the above procedure was prepared as described below:

(i) D-pyroglutamic acid ethyl ester (4.17 g, 26.53 mmol) was dissolved in tetrahydrofuran (30 ml) and ethyl iodide (2.23 ml, 27.86 mmol) was added to give a pale yellow solution. This was cooled to 0° C. and sodium hydride (60% in oil, 1.11 g, 27.86 mmol) was added portionwise. After addition of all the sodium hydride the mixture was stirred at 0° C. for a further 20 minutes until most of the bubbling had stopped. The mixture was then warmed to room temperature and stirred overnight under argon. The mixture was then treated with saturated aqueous ammonium chloride solution (~5 ml). The organic layer was separated and the aqueous layer was extracted with more dichloromethane (3×20 ml). The combined organic layers were dried by passing through a phase separator and then concentrated to a green/brown oil (3.2 g). This was purified by automated flash silica column chromatography (Biotage SP4), eluting with a 0-100% gradient of ethyl acetate in hexane, to give ethyl 1-ethyl-5-oxoprolinate as a yellow oil (1.33 g) which was used in the next step without further purification.

(ii) Ethyl 1-ethyl-5-oxoprolinate (1.33 g, 7.18 mmol) was dissolved in ethanol (10 ml) and cooled to 0° C. in an ice bath. To this was added 12.5M aqueous sodium hydroxide solution (1.72 ml, 21.53 mmol) and the mixture was stirred for ~4 hours at 0° C. The ethanol was evaporated under vacuum and the aqueous residue was acidified with 2N aqueous hydrogen chloride to pH1. The volume of the aqueous phase was reduced to ~3 ml under vacuum and then extracted with a 3:1 mixture of chloroform and isopropanol using a phase separator. The combined organic layers were concentrated to a pale yellow oil which on drying in vacuo crystallized to give 1-ethyl-5-oxoproline as a white solid (1.12 g).

Examples 71-82

In a manner analogous to that described for Example 70 above the compounds tabulated below (Table 6) were prepared by substituting the appropriate amine (or salt thereof) for the 2-chloro-4-fluorobenzylamine used in the above procedure. All of the amines used to make the compounds shown in Table 6 are available from commercial sources or can be prepared using routes described previously in the chemical literature unless stated otherwise. Where determined (by chiral HPLC), the enantiomeric excess (e.e.) of the isomer shown is also listed along with its stereospecific name, the chiral separation method used in parentheses and the corresponding retention time (r.t.) in that method.

TABLE 6

| Example no. | Chemical name | [M + H]⁺ | Retention time (mins) | e.e. |
|---|---|---|---|---|
| E71 | N-[(2,4-dichlorophenyl)methyl]-1-ethyl-5-oxoprolinamide | 315 | 2.36 | 75.6%<br>(C)<br>N-[(2,4-dichlorophenyl)methyl]-1-ethyl-5-oxo-D-prolinamide<br>r.t. = 6.18 mins |
| E72 | N-{[2-chloro-3-(trifluoromethyl)phenyl]methyl}-1-ethyl-5-oxoprolinamide | 349 | 2.44 | 76.4%<br>(A)<br>N-{[2-chloro-3-(trifluoromethyl)phenyl]methyl}-1-ethyl-5-oxo-D-prolinamide<br>r.t. = 4.44 mins |
| E73 | N-{[4-chloro-3-(trifluoromethyl)phenyl]methyl}-1-ethyl-5-oxoprolinamide | 349 | 2.5 | 77.3%<br>(A)<br>N-{[4-chloro-3-(trifluoromethyl)phenyl]methyl}-1-ethyl-5-oxo-D-prolinamide<br>r.t. = 4.45 mins |
| E74 | N-[(2-chloro-6-methylphenyl)methyl]-1-ethyl-5-oxoprolinamide | 295 | 2.23 | 77.6%<br>(C)<br>N-[(2-chloro-6-methylphenyl)methyl]-1-ethyl-5-oxo-D-prolinamide<br>r.t. = 5.08 mins |
| E75 | N-[(3,4-dichlorophenyl)methyl]-1-ethyl-5-oxoprolinamide | 315 | 2.38 | 76.3%<br>(C)<br>N-[(3,4-dichlorophenyl)methyl]-1-ethyl-5-oxo-D-prolinamide<br>r.t. = 4.38 mins |
| E76 | N-[(2-chlorophenyl)methyl]-1-ethyl-5-oxoprolinamide | 281 | 2.06 | |

TABLE 6-continued

| Example no. | Chemical name | [M + H]+ | Retention time (mins) | e.e. |
|---|---|---|---|---|
| E77 | 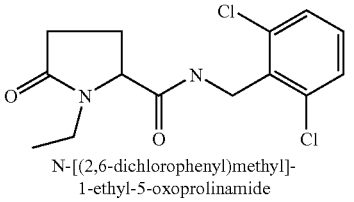 N-[(2,6-dichlorophenyl)methyl]-1-ethyl-5-oxoprolinamide | 315 | 2.11 | |
| E78 | 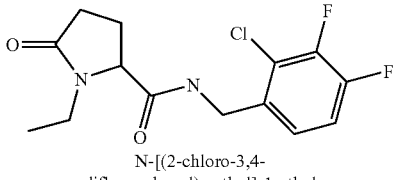 N-[(2-chloro-3,4-difluorophenyl)methyl]-1-ethyl 5-oxoprolinamide | 317 | 2.13 | |
| E79 | 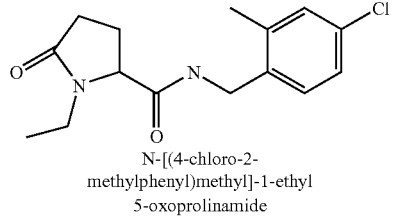 N-[(4-chloro-2-methylphenyl)methyl]-1-ethyl 5-oxoprolinamide | 295 | 2.24 | |
| E80 | 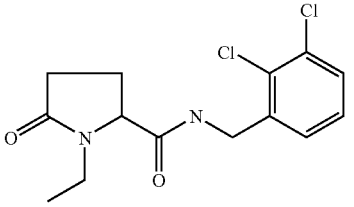 N-[(2,3-dichlorophenyl)methyl]-1-ethyl-5-oxoprolinamide | 315 | 2.23 | |
| E81 | 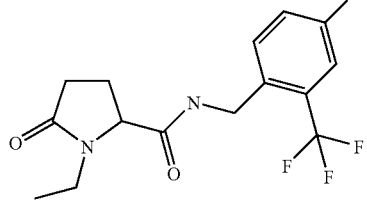 1-ethyl-N-{[4-fluoro-2-(trifluoromethyl)phenyl]methyl}-5-oxoprolinamide | 333 | 2.25 | |
| E82 | 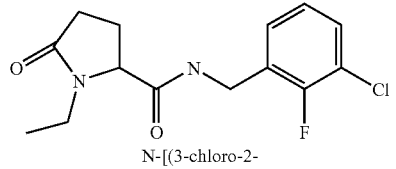 N-[(3-chloro-2-fluorophenyl)methyl]-1-ethyl-5-oxoprolinamide | 299 | 2.1 | |

Example 83

N-{[4-fluoro-2-(trifluoromethyl)phenyl]methyl}-1-methyl-5-oxoprolinamide (E83)

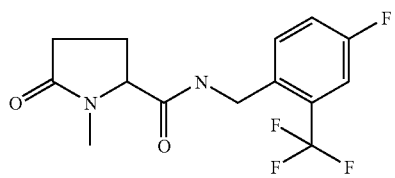

N-{[4-fluoro-2-(trifluoromethyl)phenyl]methyl}-1-methyl-5-oxoprolinamide was prepared in a manner analogous to that described above for the synthesis of N-[(2-chloro-4-fluorophenyl)methyl]-1-ethyl-5-oxoprolinamide (Example 70) but 1-methyl-5-oxoproline (prepared as describe below) was substituted for 1-ethyl-5-oxoproline and {[4-fluoro-2-(trifluoromethyl)phenyl]methyl}amine was substituted for 2-chloro-4-fluorobenzylamine.

LC/MS [M+H]$^+$=319, retention time=2.14 minutes.

The 1-methyl-5-oxoproline used in the above procedure was prepared as described below:

(i) D-pyroglutamic acid ethyl ester (4.0 g, 25.5 mmol) was dissolved in tetrahydrofuran (25 ml) and cooled to 0° C. Methyl iodide (1.66 ml, 26.7 mmol) was added and stirring continued for 10 minutes under argon at 0° C. Sodium hydride (60% in oil, 1.6 g, 26.7 mmol) was then added portionwise (allowing each portion to react). After addition of all the sodium hydride the mixture was allowed to warm to room temperature and stirred overnight under argon. The mixture was then treated with saturated aqueous ammonium chloride solution (~15 ml) and stirred for 4 hrs. The organic layer was separated and the aqueous layer was extracted with more dichloromethane. The combined organic layers were dried over magnesium sulphate and then concentrated to a dark oil. This was purified by flash silica column chromatography, eluting with a 0-75% gradient of ethyl acetate in hexane, to give ethyl 1-methyl-5-oxoprolinate as a colourless oil (0.27 g) which was used in the next step without further purification.

(ii) Ethyl 1-methyl-5-oxoprolinate (0.27 g, 1.58 mmol) was dissolved in ethanol (5 ml) and cooled to 0° C. in an ice bath. To this was added 2M aqueous sodium hydroxide solution (3 ml) and the mixture was stirred for ~4 hours at 0° C. The ethanol was evaporated under vacuum and the aqueous residue was acidified with 2N aqueous hydrogen chloride to pH1. The volume of the aqueous phase was reduced to ~3 ml under vacuum and then extracted with a 3:1 mixture of chloroform and isopropanol using a phase separator. The combined organic layers were concentrated to give 1-methyl-5-oxoproline which was used without further purification.

Examples 84-90

Furthermore, and also in a manner analogous to that described for Example 70 above the compounds tabulated below (Table 7) were prepared by substituting the appropriate amine (or salt thereof) for the 2-chloro-4-fluorobenzylamine used in Example 70. All of the amines used to make the compounds shown in Table 7 are available from commercial sources or can be prepared using routes described previously in the chemical literature unless stated otherwise. 1-Methyl-5-oxoproline (prepared as describe above for example 81) was substituted for the 1-ethyl-5-oxoproline used in Example 70. Where determined (by chiral HPLC), the enantiomeric excess (e.e.) of the isomer shown is also listed along with its stereospecific name, the chiral separation method used in parentheses and the corresponding retention time (r.t.) in that method.

TABLE 7

| Example no. | Chemical name | [M + H]$^+$ | Retention time (mins) | e.e. |
|---|---|---|---|---|
| E84 | N-[(2,3-dichlorophenyl)methyl]-1-methyl-5-oxoprolinamide | 301 | 2.11 | |
| E85 | N-{[2-chloro-3-(trifluoromethyl)phenyl]methyl}-1-methyl-5-oxoprolinamide | 335 | 2.27 | 94.1% (A) N-{[2-chloro-3-(trifluoromethyl)phenyl]methyl}-1-methyl-5-oxo-D-prolinamide r.t. = 5.17 mins |
| E86 | N-[(2,6-dichlorophenyl)methyl]-1-methyl-5-oxoprolinamide | 301 | 1.98 | |

TABLE 7-continued

| Example no. | Chemical name | [M + H]+ | Retention time (mins) | e.e. |
|---|---|---|---|---|
| E87 | 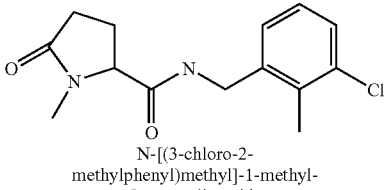 N-[(3-chloro-2-methylphenyl)methyl]-1-methyl-5-oxoprolinamide | 281 | 2.11 | |
| E88 | 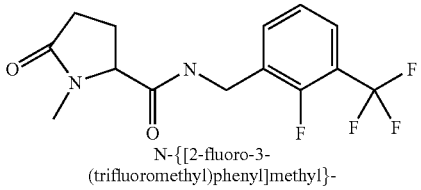 N-{[2-fluoro-3-(trifluoromethyl)phenyl]methyl}-1-methyl-5-oxoprolinamide | 319 | 2.16 | |
| E89 | 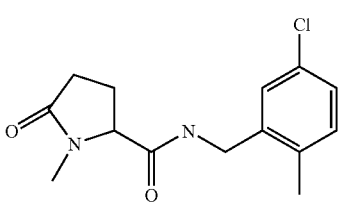 N-[(5-chloro-2-methylphenyl)methyl]-1-methyl-5-oxoprolinamide | 281 | 2.1 | |
| E90 | 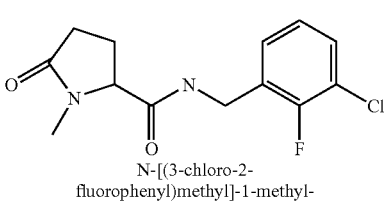 N-[(3-chloro-2-fluorophenyl)methyl]-1-methyl-5-oxoprolinamide | 285 | 1.98 | |

Example 91

N-[(2-chloro-4-fluorophenyl)methyl]-5-oxo-1-phenyl-prolinamide (E91)

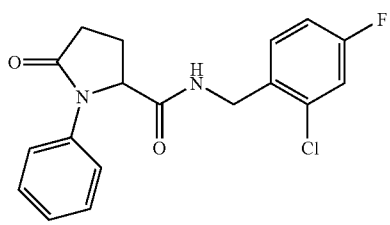

5-oxo-1-phenyl-proline (0.072 g, 0.35 mmol, prepared as described below) was dissolved in dichloromethane (~2 ml) and dimethylformamide (0.5 ml) and to this was added N-(3-dimethylaminopropyl)-N'-ethylcarbodiimide hydrochloride (0.081 g, 0.42 mmol), 1-hydroxybenzotriazole (0.057 g, 0.42 mmol), and N-ethyl morpholine (0.134 ml, 1.05 mmol). The mixture was stirred at room temperature for 30 minutes and then [(2-chloro-4-fluorophenyl)methyl]amine (0.067 g, 0.42 mmol) was added. Stirring was continued overnight at room temperature and then the mixture was diluted with more dichloromethane and saturated aqueous sodium hydrogen carbonate. The aqueous layer was separated and extracted with more dichloromethane (3 aliquots). The combined organic layers were then washed with brine before drying over magnesium sulphate. Evaporation of the solvent then gave a yellow oil which was purified by mass-directed automated HPLC. Finally trituration of the material thus obtained with a 1:1 mixture of dichloromethane and diethyl ether gave, after filtration and drying, pure N-[(2-chloro-4-fluorophenyl)methyl]-5-oxo-1-phenyl-prolinamide (0.031 g) as a white solid.

LC/MS [M+H]+=347, retention time=2.46 minutes.

The 5-oxo-1-phenyl-proline used in the above procedure was prepared as follows:

(i) D-pyroglutamic acid ethyl ester (0.200 g, 1.27 mmol) was dissolved in dioxane (5 ml) and treated with tris(dibenzylideneacetone)dipalladium (0) (0.058 g, 0.06 mmol), bromobenzene (0.351 ml, 1.53 mmol), cesium carbonate (0.621 g, 1.91 mmol) and Xantphos™ (0.110 g, 0.19 mmol). The resulting mixture was heated at reflux overnight and then allowed to cool to room temperature. The mixture was diluted with methanol and filtered. The filtrate was evaporated in vacuo and then partitioned between dichloromethane and saturated aqueous sodium hydrogen carbonate. The aqueous layer was extracted with more dichloromethane (3 aliquots) and then the combined organic layers were washed with brine and dried over magnesium sulphate. Evaporation of the solvent gave a bright yellow residue which was purified by flash silica column chromatography, eluting with a gradient of 0-50% ethyl acetate in hexane, to give methyl 5-oxo-1-phenylprolinate (0.078 g) as a yellow oil. This was used in the next step without further purification.

(ii) Methyl 5-oxo-1-phenylprolinate (0.078 g, 0.36 mmol) was combined with 2N aqueous sodium hydroxide (2 ml) in ethanol (2 ml) at 0° C. The mixture was stirred at between −10° C. and 0° C. for 5 hours. The solvent was then evaporated in vacuo and the residue was acidified to pH1 by the addition of 2M aqueous hydrogen chloride. To this was added dichloromethane and the mixture was passed through a phase separator. The aqueous layer was washed with more dichloromethane and then the combined dichloromethane layers were evaporated to give 5-oxo-1-phenyl-proline (0.072 g) as a yellow gum which was used without further purification in the next step.

Example 92

N-{[2-chloro-3-(trifluoromethyl)phenyl]methyl}-5-oxo-1-(phenylmethyl)prolinamide (E92)

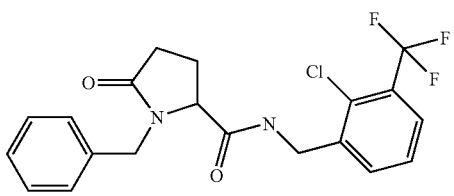

5-oxo-1-(phenylmethyl)proline (0.100 g, 0.46 mmol, prepared as described below) was dissolved in a mixture of dichloromethane (2.5 ml) and dimethylformamide (0.5 ml) and to this were added N-(3-dimethylaminopropyl)-N'-ethylcarbodiimide hydrochloride (0.105 g, 0.55 mmol), 1-hydroxybenzotriazole (0.074 g, 0.55 mmol), and N-ethyl morpholine (0.143 ml, 1.37 mmol). The mixture was stirred for 10 minutes and then {[2-chloro-3-(trifluoromethyl)phenyl]methyl}amine (0.115 g, 0.55 mmol) was added and the mixture was stirred for 1 hr. Saturated aqueous sodium hydrogen carbonate (10 ml) was added and the mixture stirred vigorously for 15 minutes. The organic phase was separated with a phase separator and the aqueous phase was washed with further aliquots of dichloromethane (3×10 ml). The organic fractions were combined and dried over magnesium sulphate. The solvent was then evaporated and the residue was purified by mass-directed automated HPLC to give pure N-{[2-chloro-3-(trifluoromethyl)phenyl]methyl}-5-oxo-1-(phenylmethyl)-D-prolinamide LC/MS [M+H]$^+$=411, retention time=2.77 minutes.

Enantiomeric excess=100.0%, as determined by chiral chromatography method D, indicative of N-{[2-chloro-3-(trifluoromethyl)phenyl]methyl}-5-oxo-1-(phenylmethyl)-D-prolinamide retention time=10.58 minutes The 5-oxo-1-(phenylmethyl)proline used in the method described above was prepared as follows:

D-glutamic acid (1.47 g, 10 mmol) was dissolved in 2N aqueous sodium hydroxide (10 ml, 20 mmol) and stirred for 15 minutes. The mixture was then treated with a solution of benzaldehyde (1.1 ml, 10 mmol) in ethanol (3 ml) and stirred at room temperature for 30 minutes. The mixture was cooled to 0° C. and treated with sodium borohydride (0.030 g). The mixture was allowed to warm to room temperature with stirring over 4 hrs and then washed with diethyl ether (three times) before acidifying with concentrated hydrochloric acid to pH2. The resulting precipitate was filtered off and washed with diethyl ether before slurrying in ethanol and azeotroping three times with more ethanol. Finally the remaining material was slurried in ethanol (50 ml) and heated at reflux for 16 hrs. The mixture was then cooled to room temperature and evaporated in vacuo. Drying afforded pure 5-oxo-1-(phenylmethyl) proline.

Example 93

N-[(2-chloro-4-fluorophenyl)methyl]-5-oxo-1-(phenyl methyl)prolinamide (E93)

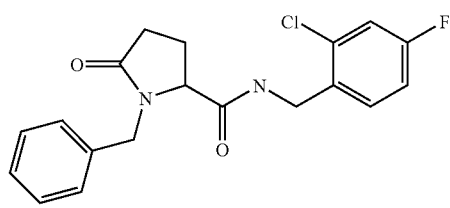

N-[(2-chloro-4-fluorophenyl)methyl]-5-oxo-1-(phenylmethyl)prolinamide was prepared in an analogous manner to that described for the synthesis of N-{[2-chloro-3-(trifluoromethyl)phenyl]methyl}-5-oxo-1-(phenylmethyl)prolinamide (Example 92) above but using [(2-chloro-4-fluorophenyl)methyl]amine in the place of {[2-chloro-3-(trifluoromethyl)phenyl]methyl}amine.

LC/MS [M+H]$^+$=361, retention time=2.54 minutes.

Example 94

N-[(2-chloro-4-fluorophenyl)methyl]-1-cyclopentyl-5-oxoprolinamide (E94)

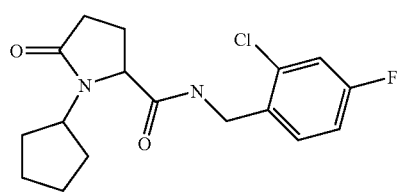

1-Cyclopentyl-5-oxoproline (0.100 g, 0.51 mmol, prepared as described below) was dissolved in a mixture of dichloromethane (2.5 ml) and dimethylformamide (0.5 ml) and to this were added N-(3-dimethylaminopropyl)-N'-ethylcarbodiimide hydrochloride (0.117 g, 0.61 mmol), 1-hydroxybenzotriazole (0.082 g, 0.61 mmol), and N-ethyl morpholine (0.2 ml, 1.52 mmol). The mixture was stirred for 10 minutes and then [(2-chloro-4-fluorophenyl)methyl]amine (0.097 g, 0.61 mmol) was added and the mixture was stirred overnight. Saturated aqueous sodium hydrogen carbonate (10 ml) was added and the mixture stirred vigorously for 15 minutes. The organic phase was separated with a phase separator and the aqueous phase was washed with further aliquots of dichloromethane (3×10 ml). The organic fractions were combined and dried over magnesium sulphate. The solvent was then evaporated and the residue was purified by mass-directed automated HPLC to give pure N-[(2-chloro-4-fluorophenyl)methyl]-1-cyclopentyl-5-oxoprolinamide.

LC/MS [M+H]⁺=339, retention time=2.4 minutes.

The 1-Cyclopentyl-5-oxoproline used in the above procedure was prepared as follows:

(i) Dimethyl D-glutamate hydrochloride (2.1 g, 10.00 mmol) was dissolved in methanol (7.5 ml) and tetrahydrofuran (15 ml) and the mixture was then treated with crushed sodium hydroxide (0.402 g, 10.05 mmol) for 20 minutes under argon. At this stage acetic acid (0.575 ml, 10.05 mmol) and cyclopentanone (0.889 ml, 10.05 mmol) were added to the mixture. After stirring for 10-15 minutes the mixture was cooled to 0° C. in an ice-bath and treated with sodium borohydride pellets (0.380 g, 10.05 mmol). The mixture was stirred for 3 hrs under argon and allowed to warm to room temperature. Once the mixture had reached room temperature the methanol was evaporated off and the residue was diluted with dichloromethane (20 ml) and washed with saturated aqueous sodium hydrogen carbonate (~25 ml). The organic layer was separated and the aqueous layer was back-extracted with more dichloromethane (2×20 ml). The combined organic layers were concentrated in vacuo to give an oil. The oil was dissolved in toluene (10 ml) and heated at reflux overnight. The solvent was then evaporated and the resulting residue was purified by flash-silica column chromatography, eluting with a gradient of 0-10% methanol in dichloromethane, to give crude methyl 1-cyclopentyl-5-oxoprolinate which was used without further purification in the next step.

(ii) Methyl 1-cyclopentyl-5-oxoprolinate (0.560 g, 2.65 mmol) was dissolved in ethanol (10 ml) and cooled to 0° C. in an ice-bath. 2M aqueous sodium hydroxide (5 ml) was added and the mixture was stirred at ice temperature for 4 hrs. The ethanol was then evaporated under vacuum and the aqueous residue was acidified to pH1 by the addition of 2N aqueous hydrogen chloride. The volume of resulting aqueous mixture was reduced under vacuum to ~3 ml and this was then extracted with a 3:1 mixture of chloroform and isopropanol respectively using a phase separator. The aqueous layer was washed with more dichloromethane and then the combined organic fractions were evaporated to give crude 1-cyclopentyl-5-oxoproline which was used in subsequent reactions without further purification.

Examples 95-99

In a manner analogous to that described for Example 94 above the compounds tabulated below (Table 8) were prepared by substituting the appropriate amine (or salt thereof) for the [(2-chloro-4-fluorophenyl)methyl]amine used in the above procedure and/or substituting the appropriate aldehyde or ketone for the cyclopentanone used in the above procedure. All of the amines used to make the compounds shown in Table 8 are available from commercial sources or can be prepared using routes described previously in the chemical literature unless stated otherwise,

TABLE 8

| Example no. | Chemical name | [M + H]⁺ | Retention time (mins) |
|---|---|---|---|
| E95 | 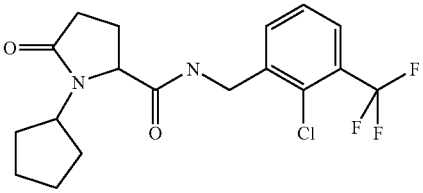<br>N-{[2-chloro-3-(trifluoromethyl)phenyl]methyl}-1-cyclopentyl-5-oxoprolinamide | 389 | 2.66 |
| E96 | 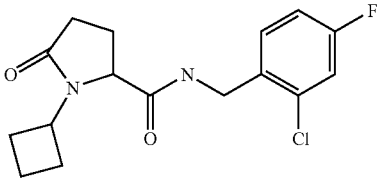<br>N-[(2-chloro-4-fluorophenyl)methyl]-1-cyclobutyl-5-oxoprolinamide | 325 | 2.35 |
| E97 | 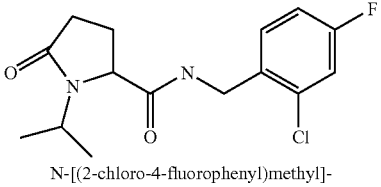<br>N-[(2-chloro-4-fluorophenyl)methyl]-1-(1-methylethyl)-5-oxoprolinamide | 313 | 2.19 |

TABLE 8-continued

| Example no. | Chemical name | [M + H]⁺ | Retention time (mins) |
|---|---|---|---|
| E98 | 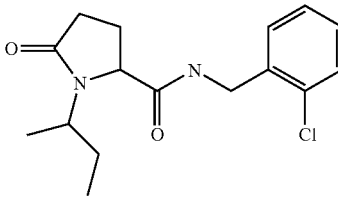  N-[(2-chloro-4-fluorophenyl)methyl]-1-(1-methylpropyl)-5-oxoprolinamide | 327 | 2.35 |
| E99 | 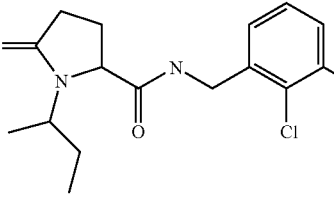  N-{[2-chloro-3-(trifluoromethyl)phenyl]methyl}-1-(1-methylpropyl)-5-oxoprolinamide | 377 | 2.6 |

Example 100

N-{[2-chloro-3-(trifluoromethyl)phenyl]methyl}-1-(2,2-dimethylpropyl)-5-oxoprolinamide (E100)

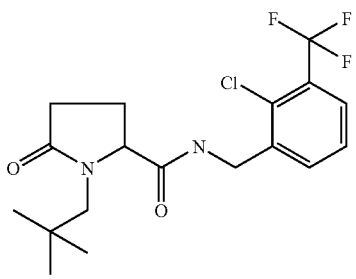

1-(2,2-dimethylpropyl)-5-oxoproline (0.100 g, 0.5 mmol, prepared as described below) was dissolved in dichloromethane (5 ml) and to this was added N-(3-dimethylaminopropyl)-N'-ethylcarbodiimide hydrochloride (0.191 g, 1 mmol), and 1-hydroxybenzotriazole (0.135 g, 1 mmol). The mixture was stirred for 30 minutes at room temperature and then {[2-chloro-3-(trifluoromethyl)phenyl]methyl}amine (0.209 g, 1 mmol) was added and the mixture was stirred overnight at room temperature. The mixture was then washed sequentially with water, 3N aqueous citric acid, and three more times with water then dried by filtering through a hydromatrix cartridge (Varian 5 g). The solvent was then evaporated and the residue was purified by mass-directed automated HPLC to give pure N-{[2-chloro-3-(trifluoromethyl)phenyl]methyl}-1-(2,2-dimethylpropyl)-5-oxoprolinamide.

LC/MS [M+H]⁺=391/393, retention time=2.78 minutes.

The 1-(2,2-dimethylpropyl)-5-oxoproline used in the method described above was prepared as follows:

L-glutamic acid (1.47 g, 10 mmol) was dissolved in 2N aqueous sodium hydroxide (10 ml, 20 mmol) and treated with a solution of trimethylacetaldehyde (1.09 ml, 10 mmol) in ethanol (5 ml) and then stirred at room temperature for 30 minutes. The mixture was cooled to 0° C. and treated with sodium borohydride (0.130 g). The mixture was allowed to warm to room temperature with stirring over 4 hrs and then acidified to neutral pH. Concentration in vacuo was followed by slurrying in ethanol and azeotroping three times with more ethanol. Finally the remaining material was suspended in ethanol (50 ml) and heated at reflux for 48 hrs. The mixture was then cooled to room temperature, salts were filtered off and the solvent was evaporated in vacuo to give a gum. Trituration with diethyl ether followed by drying afforded pure solid 1-(2,2-dimethylpropyl)-5-oxoproline (1.1 g).

Example 101

N-{[2-chloro-3-(trifluoromethyl)phenyl]methyl}-5-oxo-1-(phenylmethyl)prolinamide (E100)

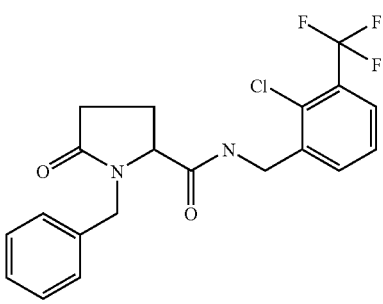

N-{[2-chloro-3-(trifluoromethyl)phenyl]methyl}-5-oxo-1-(phenylmethyl)-D-prolinamide was prepared in an analogous manner to that described for the synthesis of N-{[2-chloro-3-(trifluoromethyl)phenyl]methyl}-1-(2,2-dimethylpropyl)-5-oxoprolinamide (example 100) above but using 5-oxo-1-(phenylmethyl)proline in the place of 1-(2,2-dimethylpropyl)-5-oxoproline.

LC/MS [M+H]⁺=411/413, retention time=2.77 minutes.

Enantiomeric excess=100.0%, as determined by chiral chromatography method D, indicative of N-{[2-chloro-3-(trifluoromethyl)phenyl]methyl}-5-oxo-1-(phenylmethyl)-D-prolinamide
retention time=8.09 minutes 5-oxo-1-(phenylmethyl)proline was prepared in an analogous manner to that described above for the synthesis of 1-(2,2-dimethylpropyl)-5-oxoproline (example 100) but using benzaldehyde in the place of trimethylacetaldehyde.

Example 102

N-[(2,4-dichlorophenyl)methyl]-1-methyl-5-oxoprolinamide (E102)

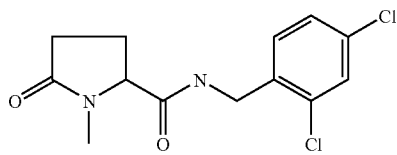

N-[(2,4-dichlorophenyl)methyl]-1-methyl-5-oxoprolinamide was prepared in a manner analogous to that described above for the synthesis of N-{[4-fluoro-2-(trifluoromethyl)phenyl]methyl}-1-methyl-5-oxoprolinamide (Example 83) but [(2,4-dichlorophenyl)methyl]amine was substituted for {[4-fluoro-2-(trifluoromethyl)phenyl]methyl}amine.

LC/MS [M+H]$^+$=300.9, retention time=2.13 minutes.

Enantiomeric excess=97.8%, as determined by chiral chromatography method A, indicative of N-[(2,4-dichlorophenyl)methyl]-1-methyl-5-oxo-D-prolinamide retention time=6.25 minutes

Example 103

1-ethyl-N-{[2-fluoro-3-(trifluoromethyl)phenyl]methyl}-5-oxoprolinamide (E103)

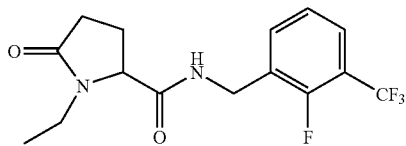

1-ethyl-N-{[2-fluoro-3-(trifluoromethyl)phenyl]methyl}-5-oxoprolinamide was prepared in a manner analogous to that described above (see example 70) for N-[(2-chloro-4-fluorophenyl)methyl]-1-ethyl-5-oxo-D-prolinamide but using 2-fluoro-3-trifluoromethylbenzylamine in the place of 2-chloro-4-fluorobenzylamine.

LC/MS [M+H]$^+$=333, retention time=2.24 minutes.

Examples 104-109

The examples tabulated below (Table 9) were prepared in a manner analogous to that described for Example 12 by substituting the appropriate amine (or salt thereof) for the [(2,3,4-trifluorophenyl)methyl]amine used in the procedure described for Example 12. All of the amines used to make the compounds shown in Table 9 are available from commercial sources or can be prepared using routes described previously in the chemical literature unless stated otherwise. The 1-ethyl-5-oxo-proline used to prepare these examples was in turn prepared using method C as described for Example 12.

TABLE 9

| Example no. | Chemical name | [M + H]$^+$ | Retention time (mins) |
|---|---|---|---|
| E104 | ![structure] N-[(2-cyanophenyl)methyl]-1-ethyl-5-oxoprolinamide | 272 | 1.63 |
| E105 | ![structure] N-{[2-cyano-3-(trifluoromethyl)phenyl]methyl}-1-ethyl-5-oxoprolinamide | 340 | 2.11 |
| E106 | ![structure] 1-ethyl-N-(1-naphthalenylmethyl)-5-oxoprolinamide | 297 | 2.17 |

TABLE 9-continued

| Example no. | Chemical name | [M + H]+ | Retention time (mins) |
|---|---|---|---|
| E107 | 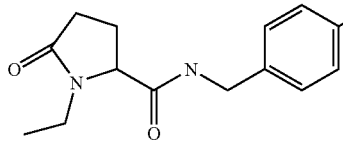 1-ethyl-5-oxo-N-{[4-(trifluoromethyl)phenyl]methyl}prolinamide | 315 | 2.30 |
| E108 | 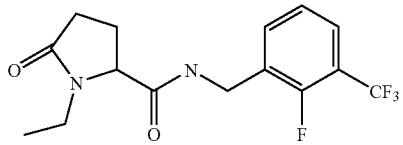 1-ethyl-N-{[2-fluoro-3-(trifluoromethyl)phenyl]methyl}-5-oxoprolinamide | 333 | 2.39 |
| E109 | 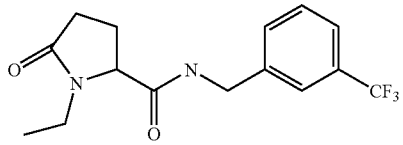 1-ethyl-5-oxo-N-{[3-(trifluoromethyl)phenyl]methyl}prolinamide | 315 | 2.34 |

The 2-(aminomethyl)-6-(trifluoromethyl)benzonitrile trifluoroacetate required for the synthesis of example 105 was prepared as follows:

(i) {[2-Fluoro-3-(trifluoromethyl)phenyl]methyl}amine (1.93 g, 10 mmol) was dissolved in dichloromethane (40 ml) and treated with a solution of bis(1,1-dimethylethyl)dicarbonate (2.18 g, 10 mmol) in dichloromethane (10 ml). After stirring at room temperature for 2 hrs the solvent was evaporated to give a pale yellow solid which was purified by silica-gel column chromatography, eluting with a 1:10-1:5 gradient of ethyl acetate in hexanes, to give pure 1,1-dimethylethyl {[2-fluoro-3-(trifluoromethyl)phenyl]methyl}carbamate (2 g).

(ii) 1,1-Dimethylethyl {[2-fluoro-3-(trifluoromethyl)phenyl]methyl}carbamate (1.17 g, 4 mmol) was dissolved in dimethylsulphoxide (5 ml) and treated with potassium cyanide (0.260 g, 4 mmol). The mixture was then heated at 80° C. under argon for 1.5 hrs and then at 120° C. overnight (16 hrs). Additional potassium cyanide (0.260 g, 4 mmol) was then added and heating continued at 120° C. for a further 24 hrs. The mixture was then cooled to room temperature, quenched with water, and diluted with ethyl acetate. The organic extracts were separated and washed three times with water and then with saturated aqueous sodium chloride solution. Drying and evaporation gave a brown gum which was purified by silica-gel column chromatography, eluting with a 1:10-1:5 gradient of ethyl acetate in hexanes, to give partially pure 1,1-dimethylethyl {[2-cyano-3-(trifluoromethyl)phenyl]methyl}carbamate as a dark solid/semi-solid which was used in the next step without further purification.

LC/MS [M-BOC+H]+=201, retention time=1.19 minutes.

(iii) 1,1-Dimethylethyl {[2-cyano-3-(trifluoromethyl)phenyl]methyl}carbamate (0.190 g, 0.63 mmol) was dissolved in dichloromethane (4 ml) and treated with trifluoroacetic acid (4 ml). The mixture was stirred at room temperature for 1 hr and then evaporated. The residue was twice taken up in dichloromethane and evaporated again to give crude 2-(aminomethyl)-6-(trifluoromethyl)benzonitrile trifluoroacetate which was used without further purification.

Example 110

1-methyl-N-(1-naphthalenylmethyl)-5-oxoprolinamide (E110)

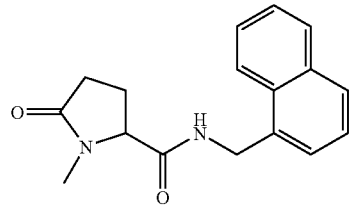

1-methyl-5-oxoproline (0.050 g, 0.35 mmol, prepared in a manner analogous to that described above for example 51), N-(3-dimethylaminopropyl)-N'-ethylcarbodiimide hydrochloride (0.081 g, 0.42 mmol), 1-hydroxybenzotriazole (0.057 g, 0.42 mmol), N-ethyl morpholine (0.166 ml, 1.05 mmol) and (1-naphthalenylmethyl)amine were combined in dichloromethane (~8 ml) and the mixture was stirred for ~20 hrs at room temperature. The mixture was then washed with 2M aqueous hydrogen chloride (5 ml) and the organic layer was separated using a phase separator. The organic layer was washed with saturated aqueous sodium hydrogen carbonate, separated as before, and then evaporated. The residue was purified by mass-directed automated HPLC to give pure 1-methyl-N-(1-naphthalenylmethyl)-5-oxoprolinamide as a white solid (0.062 g).

LC/MS [M+H]+=283, retention time=2.1 minutes.

Example 111

N-{[2-chloro-4-fluoro-3-(trifluoromethyl)phenyl]methyl}-1-methyl-5-oxoprolinamide (E111)

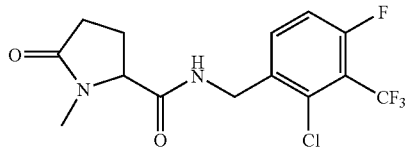

1-methyl-5-oxoproline (0.057 g, 0.4 mmol, prepared in a manner analogous to that described above for example 51) dissolved in dichloromethane (4 ml) and treated with 2-ethoxy-1-ethoxycarbonyl-1,2-dihydroquinoline (0.104 g, 0.42 mmol). {[2-Chloro-4-fluoro-3-(trifluoromethyl) phenyl]methyl}amine hydrochloride (0.105 g, 0.4 mmol, prepared as described below) was then added and the mixture was stirred at room temperature for 4 hrs. The mixture was treated with saturated aqueous sodium hydrogen carbonate (10 ml) and stirred for 5 minutes. The organic phase was separated using a hydrophobic frit and then washed with 2N aqueous hydrogen chloride (2×10 ml). Evaporation of the organic phase then gave pure N-{[2-chloro-4-fluoro-3-(trifluoromethyl)phenyl]methyl}-1-methyl-5-oxoprolinamide (0.106 g).

LC/MS [M+H]$^+$=353, retention time=2.49 minutes.

The {[2-Chloro-4-fluoro-3-(trifluoromethyl)phenyl]methyl}amine hydrochloride used in the method described above was prepared as follows:

(i) 1-Chloro-3-fluoro-2-(trifluoromethyl)benzene (10 g, 50 mmol) was dissolved in tetrahydrofuran (100 ml), cooled to −70° C. under argon, and treated with a 1.4M solution of sec-butyl lithium in cyclohexane (37.5 ml, 52.5 mmol). Stirring was continued for 2 hrs and then trimethylsilyl chloride (6.7 ml, 52.5 mmol) was added and stirring continued, still at −70° C., for a further 1 hr. The mixture was allowed to warm to room temperature and the tetrahydrofuran was then removed in vacuo. The residue was partitioned between diethyl ether and water and then the organic layer was separated and washed with 2N aqueous hydrogen chloride. The organic phase was separated and concentrated to give the crude product which was purified by flash silica-gel column chromatography, eluting with hexane, to give pure [4-chloro-2-fluoro-3-(trifluoromethyl)phenyl](trimethyl)silane as a clear oil (10.35 g).

(ii) 2,2,6,6-tetramethylpiperidine (3.3 ml, 19.44 mmol) was added slowly to a solution of n-butyl lithium (2.5M in toluene, 7.7 ml, 19.44 mmol) in tetrahydrofuran (75 ml) at −75° C. under argon and stirred for 15 minutes. A solution of [4-chloro-2-fluoro-3-(trifluoromethyl)phenyl](trimethyl)silane (5 g, 18.5 mmol) in tetrahydrofuran (10 ml) was then added dropwise to the mixture, ensuring that the temperature of the mixture was kept below −65° C., and stirring was continued for 2 hrs. Excess solid carbon dioxide, which had previously been washed with tetrahydrofuran at −65° C., was added in lumps and the mixture was allowed to warm to room temperature over 2 hrs. The mixture was reduced under vacuum to give a pale yellow solid. This material was partitioned between water which had been acidified to pH1 (200 ml) and diethyl ether (200 ml). The organic layer was separated and dried over anhydrous sodium sulphate. Evaporation gave a pale brown solid which was recrystallised from toluene to give pure 2-chloro-4-fluoro-3-(trifluoromethyl)-5-(trimethylsilyl)benzoic acid (3.85 g, in 3 batches) as white needles.

LC/MS [M−H]$^-$=312, retention time=3.29 minutes.

(iii) A solution of potassium fluoride (0.367 g, 9.55 mmol) in water (15 ml) was added to a solution of 2-chloro-4-fluoro-3-(trifluoromethyl)-5-(trimethylsilyl)benzoic acid (1 g, 3.18 mmol) in tetrahydrofuran (50 ml) and the mixture was stirred at 100° C. overnight. An additional aliquot of water (15 ml) and potassium fluoride (0.370 g, 9.62 mmol) was added and heating at 100° C. was continued for a further 4 hrs. The tetrahydrofuran was evaporated in vacuo and replaced with enough dimethylformamide to dissolve all solids. The mixture was heated overnight at 100° C. but starting material still remained so more potassium fluoride (0.367 g, 9.55 mmol) was added and heating at 100° C. continued for 7 days. At this stage almost all of the starting material had disappeared so the reaction was evaporated to dryness under vacuum and taken up in 2N aqueous hydrogen chloride (75 ml) and diethyl ether (50 ml). The aqueous layer was separated and extracted with more diethyl ether (2×50 ml) and then the combined organic fractions were dried over sodium sulphate and evaporated to give crude product as a white solid. This was purified by recrystallisation from toluene to give pure 2-chloro-4-fluoro-3-(trifluoromethyl)benzoic acid (0.566 g) as a white solid.

(iv) 2-Chloro-4-fluoro-3-(trifluoromethyl)benzoic acid (0.560 g, 2.31 mmol), ammonium 1H-1,2,3-benzotriazol-1-olate (0.534 g, 3.47 mmol, prepared as described below), N-(3-dimethylaminopropyl)-N'-ethylcarbodiimide hydrochloride (0.643 g, 3.47 mmol), and N-ethyl morpholine (0.594 ml, 4.62 mmol) were stirred together in dichloromethane (30 ml) for a total of 3 hrs. Saturated aqueous sodium hydrogen carbonate (30 ml) was added and the mixture was stirred for 15 minutes. The organic layer was separated using a hydrophobic frit and then washed with 2N aqueous hydrogen chloride (2×50 ml). Separation of the organic layer, again using a hydrophobic frit, and evaporation in vacuo gave 2-chloro-4-fluoro-3-(trifluoromethyl)benzamide (0.493 g) as an off-white solid which was used without further purification in the subsequent step.

The ammonium 1H-1,2,3-benzotriazol-1-olate used in the step described above was prepared as follows:

Ammonium hydroxide (4.15 ml, 75 mmol) was added slowly to a solution of 1-hydroxybenzotriazole (10 g, 74 mmol) in tetrahydrofuran (100 ml) at 0° C. (ice-bath) and stirred for 2 hrs. Filtration and washing with tetrahydrofuran gave ammonium 1H-1,2,3-benzotriazol-1-olate (10.57 g) as a white solid.

(v) 2-Chloro-4-fluoro-3-(trifluoromethyl)benzamide (0.490 g, 2.03 mmol) was treated with 1M borane in tetrahydrofuran (20.33 ml, 20.33 mmol) and stirred at 60° C. overnight. The mixture was then treated with 2N aqueous hydrogen chloride until gas evolution ceased and then stirred at 100° C. for 2 hrs. The mixture was reduced in vacuo and the residue was taken up in a minimum of water and washed with dichloromethane (30 ml). The pH of the aqueous layer was adjusted to pH11 by the addition of 2N aqueous sodium hydroxide solution and then extracted with dichloromethane (2×25 ml). The dichloromethane layers were separated using a hydrophobic frit, combined and evaporated in vacuo to leave a pale yellow oil. A 1M solution of hydrogen chloride in diethyl ether (3 ml, 3 mmol) was added and the resulting white solid was filtered off to give pure {[2-Chloro-4-fluoro- 3-(trifluoromethyl)phenyl]methyl}amine hydrochloride (0.210 g) which was used without further purification.

Example 112

N-{[2-chloro-3-(trifluoromethyl)phenyl]methyl}-1-cyclobutyl-5-oxoprolinamide (E112)

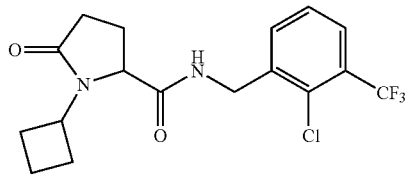

1-Cyclobutyl-5-oxoproline (0.238 g, 0.82 mmol) was suspended in dichloromethane (3 ml) and to this was added N-(3-dimethylaminopropyl)-N'-ethylcarbodiimide hydrochloride (0.188 g, 0.98 mmol), 1-Hydroxybenzotriazole (0.132 g, 0.98 mmol), and N-ethyl morpholine (0.313 ml, 2.46 mmol). The mixture was stirred at room temperature for 30 minutes and then {[2-chloro-3-(trifluoromethyl)phenyl]methyl}amine (0.205 g, 0.98 mmol) was added to the mixture and stirring continued for ~20 hrs at room temperature. The mixture was then diluted with more dichloromethane and treated with saturated aqueous sodium hydrogen carbonate. The dichloromethane layer was separated and the aqueous layer was extracted with 3 further aliquots of dichloromethane. The combined organic extracts were washed with water and then with brine, dried over anhydrous magnesium sulphate and evaporated in vacuo to give the crude product. This was further purified by mass-directed automated HPLC to give pure N-{[2-chloro-3-(trifluoromethyl)phenyl]methyl}-1-cyclobutyl-5-oxoprolinamide (0.105 g) as a white solid.

LC/MS [M+H]$^+$=375, retention time=2.53 minutes.

The 1-Cyclobutyl-5-oxoproline used in the above procedure was prepared in an analogous manner to that described previously for the synthesis of methyl 1-ethyl-5-oxo-prolinate (see example 3) but using cyclobutanone in the place of acetaldehyde and with the addition of a subsequent ester deprotection step (using standard conditions, i.e. sodium hydroxide in methanol) being carried out (as opposed to the combined deprotection and amide coupling described in example 3).

Examples 113-117

In a manner analogous to that described for Example 112 above the compounds tabulated below (Table 10) were prepared by substituting the appropriate amine (or salt thereof) for the {[2-chloro-3-(trifluoromethyl)phenyl]methyl}amine used in the above procedure. All of the amines used to make the compounds shown in Table 10 are available from commercial sources or can be prepared using routes described previously in the chemical literature unless stated otherwise.

TABLE 10

| Example no. | Chemical name | [M + H]$^+$ | Retention time (mins) |
|---|---|---|---|
| E113 | N-[(3-chloro-2-methylphenyl)methyl]-1-cyclobutyl-5-oxoprolinamide | 321 | 2.39 |
| E114 | 1-cyclobutyl-N-[(2,4-dichlorophenyl)methyl]-5-oxoprolinamide | 341 | 2.46 |
| E115 | N-[(2-chloro-3,4-difluorophenyl)methyl]-1-cyclobutyl-5-oxoprolinamide | 343 | 2.32 |

TABLE 10-continued

| Example no. | Chemical name | [M + H]⁺ | Retention time (mins) |
|---|---|---|---|
| E116 | 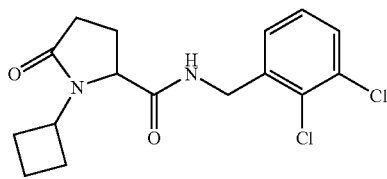<br>1-cyclobutyl-N-[(2,3-dichlorophenyl)methyl]-5-oxoprolinamide | 341 | 2.38 |
| E117 | 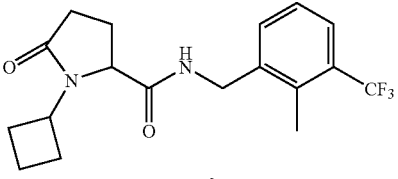<br>1-cyclobutyl-N-{[2-methyl-3-(trifluoromethyl)phenyl]methyl}-5-oxoprolinamide | 355 | 2.51 |

The [(2-chloro-3,4-difluorophenyl)methyl]amine hydrochloride required for the synthesis of N-[(2-chloro-3,4-difluorophenyl)methyl]-1-cyclobutyl-5-oxoprolinamide (Example 115) was prepared as described above for example 36.

Example 118

N-{[2-chloro-3-(trifluoromethyl)phenyl]methyl}-1-(2,2-dimethylpropyl)-5-oxoprolinamide (E118)

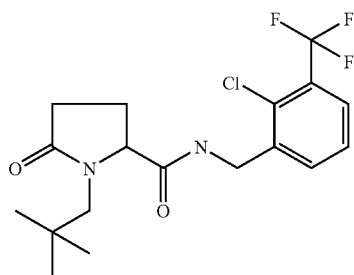

N-{[2-chloro-3-(trifluoromethyl)phenyl]methyl}-1-(2,2-dimethylpropyl)-5-oxoprolinamide was prepared in an analogous manner to that described for example 100 but using 1-(2,2-dimethylpropyl)-5-oxoproline prepared as described below.

LC/MS [M+H]⁺=391/393, retention time=2.76 minutes.

The 1-(2,2-dimethylpropyl)-5-oxoproline used in the method described above was prepared as follows:

D-glutamic acid (2.21 g, 15 mmol) was dissolved in 2N aqueous sodium hydroxide (15 ml, 30 mmol), cooled to 0° C., and treated with a solution of trimethylacetaldehyde (1.63 ml, 15 mmol) in ethanol (3 ml) and then stirred at room temperature for 45 minutes. The mixture was again cooled to 0° C. and treated portion-wise with sodium borohydride (0.189 g, 5 mmol). The mixture was allowed to warm to room temperature with stirring over 4 hrs then after washing with diethyl ether it was acidified to ~pH4 using concentrated hydrochloric acid. The resulting precipitate was collected by filtration, washed with diethyl ether and then dried in a vacuum oven overnight. The solid was then suspended in ethanol (50 ml) and the mixture was heated at reflux for 24 hrs. Concentration and trituration with hexane then afforded 1-(2,2-dimethylpropyl)-5-oxoproline (1.51 g) as a solid which was used without further purification.

Example 119

N-{[2-chloro-3-(trifluoromethyl)phenyl]methyl}-5-oxo-1-(2-pyridinylmethyl)prolinamide (E119)

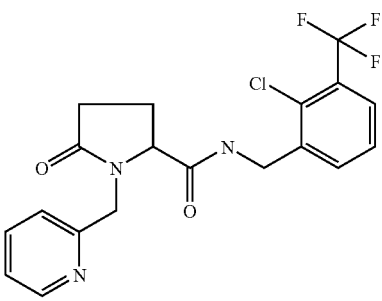

5-oxo-1-(2-pyridinylmethyl)proline (0.220 g, 1 mmol, prepared as described below), N-(3-dimethylaminopropyl)-N'-ethylcarbodiimide hydrochloride (0.384 g, 2 mmol), and 1-hydroxybenzotriazole (0.308 g, 2 mmol) were stirred together in dichloromethane (10 ml) at room temperature for 30 minutes. The mixture was then treated with {[2-chloro-3-(trifluoromethyl)phenyl]methyl}amine (0.314 g, 1.5 mmol)

and the mixture was stirred overnight at room temperature. The mixture was concentrated and partitioned between ethyl acetate and saturated aqueous sodium hydrogen carbonate solution. The aqueous layer was separated and extracted with ethyl acetate and then the combined ethyl acetate fractions were washed with 3 portions of water and then with saturated aqueous sodium chloride solution. Drying over sodium sulphate and concentration gave a solid residue which was purified by mass-directed automated HPLC to give N-{[2-chloro-3-(trifluoromethyl)phenyl]methyl}-5-oxo-1-(2-pyridinylmethyl)prolinamide (0.263 g) as a buff-coloured solid.

LC/MS [M+H]$^+$=412/414, retention time=2.15 minutes.

The 5-oxo-1-(2-pyridinylmethyl)proline used in the method described above was prepared as follows:

D-glutamic acid (2.21 g, 15 mmol) was dissolved in 2N aqueous sodium hydroxide (15 ml, 30 mmol) at 0° C. and then treated with pyridine-2-carboxaldehyde (1.43 ml, 15 mmol). The mixture was stirred at room temperature for 45 minutes and then cooled to 0° C. and treated with sodium borohydride (0.189 g, 5 mmol). The mixture was allowed to warm to room temperature with stirring over 4 hrs then after washing twice with diethyl ether it was acidified to pH5-6. The aqueous layer was concentrated then azeotroped three times with toluene and then with a 1:1 ethanol:toluene mixture and finally with ethanol. The residue was then taken up in ethanol (50 ml) and refluxed for 8 hrs. Concentration gave an oil which when dried in vacuo gave 5-oxo-1-(2-pyridinylmethyl)proline (2.60 g) as a foam which was used without any further purification.

Example 120

N-{[2-chloro-3-(trifluoromethyl)phenyl]methyl}-5-oxo-1-(3-pyridinylmethyl)prolinamide (E120)

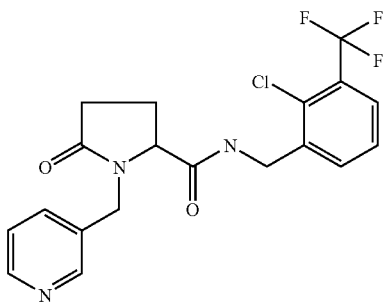

5-oxo-1-(3-pyridinylmethyl)proline (0.210 g, 1 mmol, prepared as described below), N-(3-dimethylaminopropyl)-N'-ethylcarbodiimide hydrochloride (0.383 g, 2 mmol), and 1-hydroxybenzotriazole (0.306 g, 2 mmol) were stirred together in dichloromethane (10 ml) at room temperature for 30 minutes. The mixture was then treated with {[2-chloro-3-(trifluoromethyl)phenyl]methyl}amine (0.314 g, 1.5 mmol) and the mixture was stirred overnight at room temperature. The mixture was concentrated and partitioned between ethyl acetate and saturated aqueous sodium hydrogen carbonate. The aqueous layer was separated and extracted with more ethyl acetate and then the combined ethyl acetate fractions were washed sequentially with 3 portions of water and then with saturated aqueous sodium chloride solution. Drying over magnesium sulphate and concentration gave a solid residue which was purified by mass-directed automated HPLC to give pure N-{[2-chloro-3-(trifluoromethyl)phenyl]methyl}-5-oxo-1-(3-pyridinylmethyl)prolinamide (0.031 g).

LC/MS [M+H]$^+$=412/414, retention time=1.83 minutes.

The 5-oxo-1-(3-pyridinylmethyl)proline used in the method described above was prepared as follows:

D-glutamic acid (2.21 g, 15 mmol) was dissolved in 2N aqueous sodium hydroxide (15 ml, 30 mmol) at 0° C. and then treated with pyridine-3-carboxaldehyde (1.41 ml, 15 mmol) in ethanol (3 ml). The mixture was stirred at room temperature for 30 minutes and then cooled to 0° C. and treated portion-wise with sodium borohydride (0.189 g, 5 mmol). The mixture was allowed to warm to room temperature with stirring over 4 hrs then after washing with diethyl ether it was acidified to pH5-6 using concentrated hydrochloric acid. The resulting precipitate was collected by filtration, washed with diethyl ether, and dried in vacuo. This material was then taken up in ethanol (50 ml) and refluxed overnight. Fine solids were removed by filtration and then concentration gave 5-oxo-1-(3-pyridinylmethyl)proline (2.04 g) as a white solid which was used without any further purification.

Example 121

N-[(2,4-dichlorophenyl)methyl]-5-oxo-1-(3-pyridinylmethyl)prolinamide (E121)

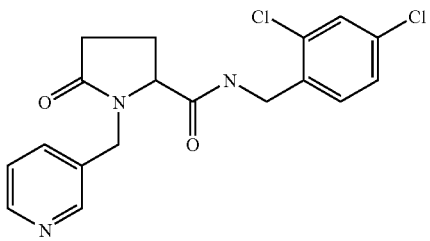

N-[(2,4-dichlorophenyl)methyl]-5-oxo-1-(3-pyridinylmethyl)prolinamide was prepared in a manner analogous to that described above for the synthesis of N-{[2-chloro-3-(trifluoromethyl)phenyl]methyl}-5-oxo-1-(3-pyridinylmethyl)prolinamide (E120) but using [(2,4-dichlorophenyl)methyl]amine in the place of {[2-chloro-3-(trifluoromethyl)phenyl]methyl}amine.

LC/MS [M+H]$^+$=378/380/382, retention time=1.70 minutes.

Example 122

1-cyclopropyl-N-[(2,4-dichlorophenyl)methyl]-2-methyl-5-oxoprolinamide (E122)

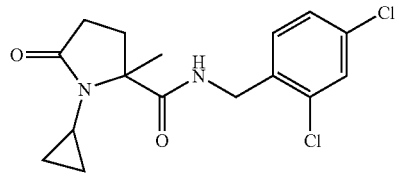

To a solution of (2,4-dichlorophenyl)methyl isocyanide (0.047 g, 0.25 mmol) and levulinic acid (0.041 ml, 0.4 mmol) in methanol (2 ml) was added cyclopropylamine (0.042 ml, 0.6 mmol). The mixture was heated to 100° C. for 30 minutes in a microwave reactor. The solvent was removed in vacuo and the residue was purified by mass-directed automated HPLC to give 1-cyclopropyl-N-[(2,4-dichlorophenyl)methyl]-2-methyl-5-oxoprolinamide (0.054 g) as a white solid.

LC/MS [M+H]$^+$=341/343, retention time=2.57 minutes.

Examples 123-126

In a manner analogous to that described for Example 122 above the compounds tabulated below (Table 11) were prepared by substituting the appropriate amine for the cyclopropylamine used in the above procedure. All of the amines used to make the compounds shown in Table 11 are available from commercial sources or can be prepared using routes described previously in the chemical literature.

TABLE 11

| Example no. | Chemical name | [M + H]+ | Retention time (mins) |
|---|---|---|---|
| E123 | 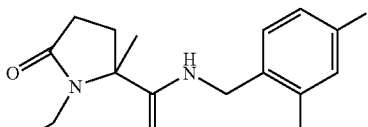 N-[(2,4-dichlorophenyl)methyl]-1-ethyl-2-methyl-5-oxoprolinamide | 329 | 2.49 |
| E124 | 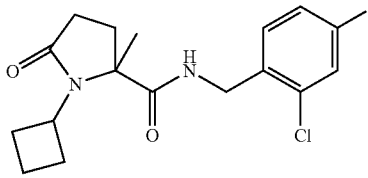 1-cyclobutyl-N-[(2,4-dichlorophenyl)methyl]-2-methyl-5-oxoprolinamide | 355/357 | 2.78 |
| E125 | 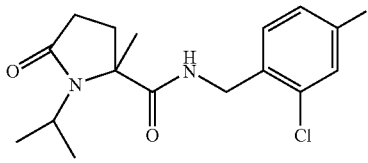 N-[(2,4-dichlorophenyl)methyl]-2-methyl-1-(1-methylethyl)-5-oxoprolinamide | 343/345 | 2.64 |
| E126 | 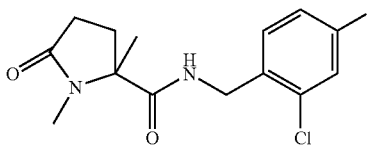 N-[(2,4-dichlorophenyl)methyl]-1,2-dimethyl-5-oxoprolinamide | 315 | 2.39 |

Example 127

N-[(2,4-dichlorophenyl)methyl]-1,3,3-trimethyl-5-oxoprolinamide (E127)

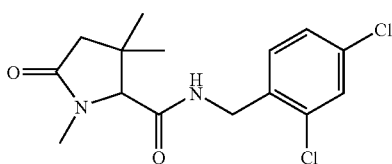

To a solution of (2,4-dichlorophenyl)methyl isocyanide (0.094 g, 0.5 mmol) and 3,3-dimethyl-4-oxobutanoic acid (0.065 mg, 0.5 mmol, prepared as described below) in methanol (2 ml) was added methylamine (0.080 ml, 33% solution in ethanol). The mixture was heated to 100° C. for 30 minutes in a microwave reactor. The solvent was removed in vacuo and the residue was purified by mass-directed automated HPLC to give a colourless gum which was triturated with diethyl ether to give N-[(2,4-dichlorophenyl)methyl]-1,3,3-trimethyl-5-oxoprolinamide (0.043 g) as a sticky white solid.

LC/MS [M+H]+=329/331, retention time=2.42 minutes.

The 3,3-dimethyl-4-oxobutanoic acid used in the procedure described above was prepared as follows:

3,3-dimethyl-4-pentenoic acid (1.3 g, 10.14 mmol) was dissolved in dichloromethane (25 ml) and cooled to −78° C. in a $CO_2$/acetone bath. Oxygen was bubbled through the mixture for 5 minutes followed by ozone for 25 minutes (giving a blue solution). Oxygen was bubbled through the mixture for a further 5 minutes followed by argon for 10 minutes. Dimethylsulphide (2.23 ml, 30.4 mmol) was then added to the mixture and the mixture was removed from the cooling bath and stirred for 2.5 hrs. The resulting colourless solution was reduced in vacuo to give 3,3-dimethyl-4-oxobutanoic acid as a colourless oil which was used without further purification.

Example 128

N-{[2-chloro-3-(trifluoromethyl)phenyl]methyl}-1,3,3-trimethyl-5-oxoprolinamide (E128)

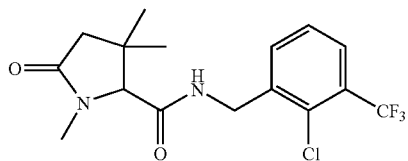

N-{[2-chloro-3-(trifluoromethyl)phenyl]methyl}-1,3,3-trimethyl-5-oxoprolinamide was prepared in a manner analogous to that described above for the synthesis of N-[(2,4-dichlorophenyl)methyl]-1,3,3-trimethyl-5-oxoprolinamide (E127) but using [2-chloro-3-(trifluoromethyl)phenyl]methyl isocyanide (prepared as described in example 40) in the place of (2,4-dichlorophenyl)methyl isocyanide.

LC/MS [M+H]$^+$=363/365, retention time=2.49 minutes.

Example 129

N-{[2-chloro-3-(trifluoromethyl)phenyl]methyl}-1,3-dimethyl-5-oxoprolinamide (E129)

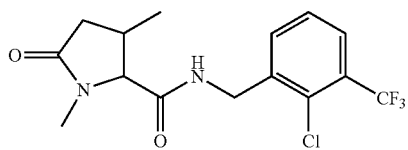

1,3-Dimethyl-5-oxoproline (0.620 g, 3.6 mmol, prepared as described below),N-(3-dimethylaminopropyl)-N'-ethylcarbodiimide hydrochloride (0.822 g, 4.3 mmol), 1-Hydroxybenzotriazole (0.581 g, 4.3 mmol), N-ethyl morpholine (1.4 ml, 10.8 mmol), and {[2-chloro-3-(trifluoromethyl)phenyl]methyl}amine (0.828 g, 3.96 mmol) were combined in a mixture of dichloromethane (10 ml) and dimethylformamide (5 ml) and stirred under argon overnight. The mixture was then washed sequentially with water (50 ml), 0.5 N aqueous hydrogen chloride (50 ml), water (50 ml), saturated aqueous sodium hydrogen carbonate (50 ml) and water (50 ml). The dichloromethane layer was passed through a hydrophobic frit and evaporated in vacuo to give the crude product. This was further purified by mass-directed automated HPLC (10×0.100 g injections) to give pure N-{[2-chloro-3-(trifluoromethyl)phenyl]methyl}-1,3-dimethyl-5-oxoprolinamide (0.613 g).

LC/MS [M+H]$^+$=349, retention time=2.31, 2.38 minutes (two diastereoisomers).

The 1,3-dimethyl-5-oxoproline used in the above procedure was prepared as follows:

(i) (R,R,R)-2-hydroxypinen-3-one (10.9 g, 64.8 mmol) and glycine-t-butyl ester (13 g, 97.2 mmol) in anhydrous toluene (200 ml) was treated with boron trifluoride-diethyl etherate (0.460 g, 3.24 mmol) and then heated, under argon, for 6 hrs at reflux. The mixture was then cooled to room temperature and stirred overnight. Filtration through a sinter followed by evaporation gave a yellow gum which was purified by automated flash silica-gel column chromatography (using a Biotage SP4), eluting with a mixture of 25% ethyl acetate in hexane, to give some pure 1,1-dimethylethyl N-[(1R,2R,5R)-2-hydroxy-2,6,6-trimethylbicyclo[3.1.1]hept-3-ylidene]glycinate (3.68 g) and some mixed fractions. The impure material was further purified, again using automated flash silica-gel column chromatography (Biotage SP4), but eluting with a gradient of 0-25% ethyl acetate in hexane (0-15% over 10 column volumes and 15-25% over 5 column volumes), to give a further crop of pure 1,1-dimethylethyl N-[(1R,2R,5R)-2-hydroxy-2,6,6-trimethylbicyclo[3.1.1]hept-3-ylidene]glycinate (1.73 g). The two batches of pure 1,1-dimethylethyl N-[(1R,2R,5R)-2-hydroxy-2,6,6-trimethylbicyclo[3.1.1]hept-3-ylidene]glycinate were combined (5.41 g) and this material was used in the next step. (Note: The glycine-t-butyl ester used above could also be replaced with glycine-t-butyl ester hydrochloride and a molar equivalent of potassium carbonate)

(ii) A solution of 1,1-dimethylethyl N-[(1R,2R,5R)-2-hydroxy-2,6,6-trimethylbicyclo[3.1.1]hept-3-ylidene]glycinate (11.05 g, 39.3 mmol) in anhydrous tetrahydrofuran (100 ml) was cooled to −30° C. and treated with a 3M solution of methylmagnesium bromide in diethyl ether (17.1 ml, 51.1 mmol). 1,8-Diazabicyclo[5.4.0]undec-7-ene (7.78 g, 51.1 mmol) was then added and the mixture was stirred for an additional 20 minutes at −30° C. The mixture was then treated with ethyl crotonate and stirring continued for 1 hr. The mixture was quenched by addition of saturated aqueous ammonium chloride solution (35 ml) and then extracted with ethyl acetate (3×100 ml). The combined organic extracts were dried over sodium sulphate, filtered and evaporated to give a yellow oil. This material was purified by automated flash silica-gel column chromatography (using a Biotage SP4), eluting with a gradient of 0-20% (over 5 column volumes) then 20-35% (over 14 column volumes) ethyl acetate in hexane, to give 1-(1,1-dimethylethyl) 5-ethyl N-[(1R,2R,5R)-2-hydroxy-2,6,6-trimethylbicyclo[3.1.1]hept-3-ylidene]-3-methylglutamate (4.2 g) which was used in the next step.

(iii) A 10% aqueous solution of citric acid (11 ml, 5.6 mmol) was added to a solution of 1-(1,1-dimethylethyl) 5-ethyl N-[(1R,2R,5R)-2-hydroxy-2,6,6-trimethylbicyclo[3.1.1]hept-3-ylidene]-3-methylglutamate (2 g) in tetrahydrofuran (10 ml) and the mixture was stirred at room temperature for 4 days. The mixture was the evaporated and the residue suspended in water (50 ml) and washed with diethyl ether (100 ml). The aqueous phase was then adjusted to pH~7 using aqueous sodium hydrogen carbonate solution and then extracted with diethyl ether (3×100 ml). The organic fractions were combined, dried over sodium sulphate, filtered and evaporated to give 1-(1,1-dimethylethyl) 5-ethyl 3-methylglutamate (1.1 g) as a yellow oil which was used in the next step without further purification.

(iv) 1-(1,1-Dimethylethyl) 5-ethyl 3-methylglutamate (1.1 g, 4.5 mmol) was left to stand, attached to a high vacuum line, overnight and then over a weekend. Starting material was still evident at this stage so toluene (30 ml) was added and the resulting mixture was heated at 110° C. overnight. Evaporation gave 1,1-dimethylethyl 3-methyl-5-oxoprolinate (0.79 g) which was used in the next step without further purification.

(v) 1,1-dimethylethyl 3-methyl-5-oxoprolinate (0.79 g, 3.96 mmol) was dissolved in tetrahydrofuran (8 ml) and treated with methyl iodide (0.27 ml, 4.36 mmol). The mixture was then cooled to 0° C. and treated portion-wise with sodium hydride (60% in oil, 0.170 g, 4.36 mmol). The mixture ceased bubbling after 30 minutes at 0° C. and was then allowed to warm to room temperature and stirred overnight. The mixture was quenched by addition of saturated aqueous ammonium chloride solution (10 ml) and the organic layer was separated and put aside. The aqueous layer was extracted with dichloromethane (3×20 ml) and the combined extracts were dried using a hydrophobic frit. All of the organic fractions (including that put aside earlier) were combined and evaporated to give crude 1,1-dimethylethyl 1,3-dimethyl-5-oxoprolinate (0.770 g) as a yellow gum which was used without further purification.

(vi) 1,1-Dimethylethyl 1,3-dimethyl-5-oxoprolinate (0.770 g, 3.62 mmol) was suspended in dichloromethane (5 ml) and treated with trifluoroacetic acid (0.4 ml, 5.4 mmol). The mixture was stirred for 5 hrs and then evaporated. Azeotroping the resulting residue with toluene then gave unreacted starting material (0.600 g). This was again taken up in dichloromethane (2 ml) and treated with trifluoroacetic acid (2 ml) once more. After stirring for 2 hrs the mixture was evaporated and the residue again azeotroped with toluene (10 ml) to give crude 1,3-dimethyl-5-oxoproline (0.760 g) which was used without any additional purification.

Example 130

N-[(2-chloro-4-fluorophenyl)methyl]-1-ethyl-4,4-dimethyl-5-oxoprolinamide (E130)

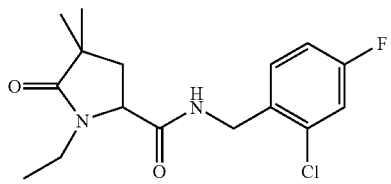

1-ethyl-4,4-dimethyl-5-oxoproline (0.130 g, 0.702 mmol, prepared as described below), 1-Hydroxybenzotriazole (0.161 g, 1.053 mmol), and N-(3-dimethylaminopropyl)-N'-ethylcarbodiimide hydrochloride (0.202 g, 1.053 mmol) were dissolved in dichloromethane (5 ml) and stirred for 15 minutes at room temperature. [(2-chloro-4-fluorophenyl)methyl] amine (0.134 g, 0.842 mmol) and diisopropylethylamine (0.184 ml, 1.053 mmol) were then added to the mixture and stirring continued overnight at room temperature. The mixture was then concentrated in vacuo and the residue partitioned between ethyl acetate and water and extracted with ethyl acetate. The combined organic layers were washed sequentially with 3N citric acid, water, saturated aqueous sodium carbonate, water (×3), and then brine and dried over anhydrous sodium sulfate. Concentration gave a crude solid which was subsequently purified by mass-directed automated HPLC to give N-[(2-chloro-4-fluorophenyl)methyl]-1-ethyl-4,4-dimethyl-5-oxoprolinamide (0.146 g) as a solid. LC/MS [M+H]$^+$=327/329, retention time=2.35 minutes.

The 1-ethyl-4,4-dimethyl-5-oxoproline used in the above procedure was prepared as described below:

(i) (S)-(+)-L-5-trityloxymethyl-2-pyrrolidinone (7.51 g, 20 mmol) was dissolved in dimethylformamide (25 ml) at 0° C. and treated portion wise with sodium hydride (60% suspension in oil, 0.880 g, 22 mmol). The mixture was stirred at 0° C. for 1 hr and then treated with ethyl iodide (1.78 ml, 22 mmol). The mixture was allowed to warm to room temperature and then stirred overnight. The mixture was then poured onto ice and extracted with ethyl acetate (×3). The combined organic extracts were washed sequentially with water, 50% aqueous sodium chloride solution (3×), and saturated aqueous sodium chloride solution, and then dried over sodium sulphate. Concentration gave a crude solid which was purified by automated flash silica-gel column chromatography (Biotage SP4), eluting with a 0-100% gradient of ethyl acetate in hexane, to give pure 1-ethyl-5-{[(triphenylmethyl)oxy]methyl}-2-pyrrolidinone (7.09 g).

(ii) To a 2M solution of lithium diisopropylamide in tetrahydrofuran (1.912 ml, 3.82 mmol) at −78° C. was added, drop-wise, a solution of 1-ethyl-5-{[(triphenylmethyl)oxy]methyl}-2-pyrrolidinone (1.34 g, 3.48 mmol) in tetrahydrofuran (10 ml) and the resulting mixture was stirred for 1 hr at −78° C. Iodomethane (0.239 ml, 3.82 mmol) was then added and after stirring for a further 1 hr at −78° C. the mixture was allowed to warm to room temperature over 3 hrs. The mixture was then re-cooled to −78° C. and treated, drop-wise, with a further aliquot of a 2M solution of lithium diisopropylamide in tetrahydrofuran (1.912 ml, 3.82 mmol). After stirring for an additional 1 hr at −78° C. the mixture was again treated with iodomethane (0.239 ml, 3.82 mmol) and then the mixture was allowed to warm to room temperature and stirred overnight. The mixture was quenched with saturated aqueous ammonium chloride and then extracted with ethyl acetate (2×). The combined organic extracts were then washed with water (3×) and then with saturated aqueous sodium chloride solution, dried over anhydrous sodium sulphate, and concentrated to a crude oily solid (1.7 g). The crude solid was purified by automated flash silica-gel column chromatography (Biotage SP4), eluting with a 0-100% gradient of ethyl acetate in hexane, to give pure product fractions (i.e. 1-ethyl-3,3-dimethyl-5-{[(triphenylmethyl)oxy]methyl}-2-pyrrolidinone (0.468 g)) as well as pure monoalkylated material (i.e. 1-ethyl-3-methyl-5-{[(triphenylmethyl)oxy]methyl}-2-pyrrolidinone (0.524 g)) and a mixture of these two (0.240 g). The desired product was set aside while the 1-ethyl-3-methyl-5-{[(triphenylmethyl)oxy]methyl}-2-pyrrolidinone and the mixed material were combined and dissolved in tetrahydrofuran (20 ml). This solution was then added drop wise to a 2M solution of lithium diisopropylamide in tetrahydrofuran (1.912 ml, 3.82 mmol) at −78° C. and stirring at this temperature was continued for 1 hr. Iodomethane (0.239 ml, 3.82 mmol) was then added to the mixture and the mixture was allowed to warm to room temperature over 4 hrs. Workup as described above gave an additional batch of 1-ethyl-3,3-dimethyl-5-{[(triphenylmethyl)oxy]methyl}-2-pyrrolidinone (0.846 g) as an oil which was combined with the material set aside earlier (total mass=1.08 g) and used in the next step without further purification.

(iii) Amberlyst 15® (5.56 g, 26.1 mmol) was washed three times with methanol and then a solution of 1-ethyl-3,3-dimethyl-5-{[(triphenylmethyl)oxy]methyl}-2-pyrrolidinone (1.08 g, 2.61 mmol) in methanol (50 ml) was added. The mixture was left to stand for 4 days at room temperature and then the resin was removed by filtration (washing with methanol). The combined methanol fractions were concentrated to give a crude oil (1.62 g) which was purified by automated flash silica-gel column chromatography (Biotage SP4), eluting with a 0-100% gradient of ethyl acetate in hexane, to give pure 1-ethyl-5-(hydroxymethyl)-3,3-dimethyl-2-pyrrolidinone (0.376 g) as an oil that solidified on standing.

(iv) 1-Ethyl-5-(hydroxymethyl)-3,3-dimethyl-2-pyrrolidinone (0.366 g, 2.1 mmol), sodium chlorite (0.387 g, 4.3 mmol), and a 1M aqueous sodium phosphate monobasic buffer solution (2.46 ml, 2.46 mmol) were combined in acetonitrile (3 ml) and heated to 40° C. A few crystals of TEMPO (2,2,6,6-tetramethyl-1-piperidinyloxy free radical) and approximately 1 drop of bleach (sodium hypochlorite solution, available chlorine >12%) were then added to the mixture and stirring continued at 40° C. for 4 hrs. The mixture was then poured onto ice containing 1% w/w sodium sulphite and the resulting mixture was extracted with ethyl acetate (×3). The combined organic extracts were washed with saturated aqueous sodium chloride and then dried over magnesium sulphate and concentrated to give 1-ethyl-4,4-dimethyl-5-oxoproline (0.392 g) as a white solid which was used without additional purification. LC/MS [M+H]$^+$=186.

Example 131

N-{[2-chloro-3-(trifluoromethyl)phenyl]methyl}-1-ethyl-4,4-dimethyl-5-oxoprolinamide (E131)

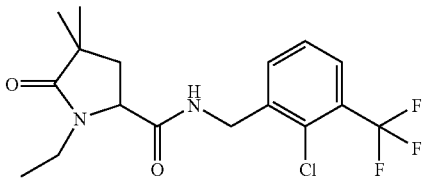

N-{[2-Chloro-3-(trifluoromethyl)phenyl]methyl}-1-ethyl-4,4-dimethyl-5-oxoprolinamide was prepared in a manner analogous to that described above for the synthesis of N-[(2-chloro-4-fluorophenyl)methyl]-1-ethyl-4,4-dimethyl-5-oxoprolinamide (E130) but using {[2-chloro-3-(trifluoromethyl)phenyl]methyl}amine in the place of [(2-chloro-4-fluorophenyl)methyl]amine.

LC/MS [M+H]$^+$=377/379, retention time=2.63 minutes.

Example 132

N-[(2-chloro-3,4-difluorophenyl)methyl]-1-ethyl-4,4-dimethyl-5-oxoprolinamide (E132)

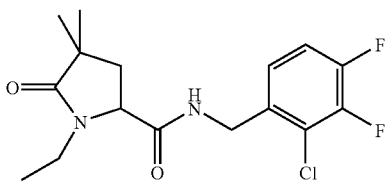

N-[(2-chloro-3,4-difluorophenyl)methyl]-1-ethyl-4,4-dimethyl-5-oxoprolinamide was prepared in a manner analogous to that described above for the synthesis of N-[(2-chloro-4-fluorophenyl)methyl]-1-ethyl-4,4-dimethyl-5-oxoprolinamide (E130) but using [(2-chloro-3,4-difluorophenyl)methyl]amine hydrochloride (prepared as described above for Example 36) in the place of [(2-chloro-4-fluorophenyl)methyl]amine.

LC/MS [M+H]$^+$=345/347, retention time=2.43 minutes.

Example 133

N-[(2-chloro-4-fluorophenyl)methyl]-1-ethyl-5-oxo-4,4-bis(phenylmethyl)prolinamide (E133)

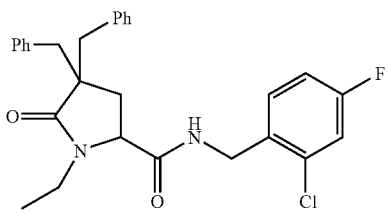

N-[(2-chloro-4-fluorophenyl)methyl]-1-ethyl-5-oxo-4,4-bis(phenylmethyl)prolinamide was prepared in a manner analogous to that described above for the synthesis of N-[(2-chloro-4-fluorophenyl)methyl]-1-ethyl-4,4-dimethyl-5-oxoprolinamide (E130) but using 1-ethyl-5-oxo-4,4-bis(phenylmethyl)proline in the place of 1-ethyl-4,4-dimethyl-5-oxoproline. 1-Ethyl-5-oxo-4,4-bis(phenylmethyl)proline was prepared in a manner analogous to that described for 1-ethyl-4,4-dimethyl-5-oxoproline in example 130 above but using 1-ethyl-3,3-bis(phenylmethyl)-5-{[(triphenylmethyl)oxy]methyl}-2-pyrrolidinone (isolated as a side-product in method B, Example 37) in place of 1-ethyl-3,3-dimethyl-5-{[(triphenyl methyl)oxy]methyl}-2-pyrrolidinone.

LC/MS [M+H]$^+$=479/481, retention time=3.32 minutes.

Example 134

N-{[2-chloro-3-(trifluoromethyl)phenyl]methyl}-1-ethyl-5-oxo-4-(phenylmethyl)prolinamide (E134)

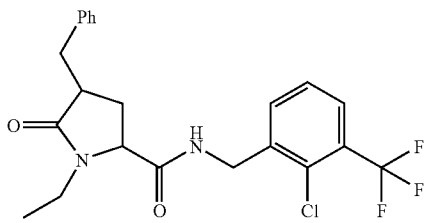

N-{[2-chloro-3-(trifluoromethyl)phenyl]methyl}-1-ethyl-5-oxo-4-(phenylmethyl)prolinamide was prepared in a manner analogous to that described above for the synthesis of N-[(2-chloro-4-fluorophenyl)methyl]-1-ethyl-5-oxo-4-(phenylmethyl)-prolinamide (E37), but using {[2-chloro-3-(trifluoromethyl)phenyl]methyl}amine in the place of [(2-chloro-4-fluorophenyl)methyl]amine. Method B, as described in Example 37, was used to prepare the 1-ethyl-5-oxo-4-(phenylmethyl)-proline.

LC/MS [M+H]$^+$=439/441, retention time=2.99 minutes.

Example 135

N-{[2-Cyano-3-(trifluoromethyl)phenyl]methyl}-1-methyl-5-oxoprolinamide (E135)

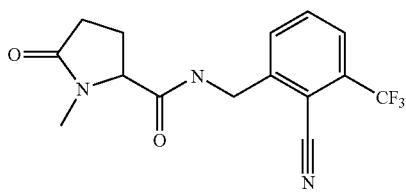

N-{[2-Cyano-3-(trifluoromethyl)phenyl]methyl}-1-methyl-5-oxoprolinamide was prepared in a manner analogous to that described above for the synthesis of N-{[2-cyano-3-(trifluoromethyl)phenyl]methyl}-1-ethyl-5-oxoprolinamide (E105) but using 1-methyl-5-oxo-proline in place of 1-ethyl-5-oxo-proline.

LC/MS [M+H]$^+$=326, retention time=2.02 minutes.

Example 136

N-(2-biphenylylmethyl)-1-ethyl-5-oxoprolinamide (E136)

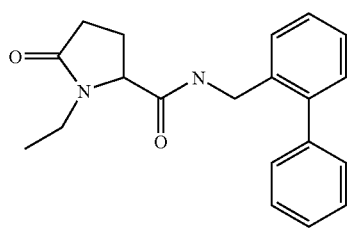

N-(2-biphenylylmethyl)-1-ethyl-5-oxoprolinamide was prepared in a manner analogous to that described above for the synthesis of N-[(2,3-dimethylphenyl)methyl]-1-ethyl-5-oxoprolinamide (E50) but using (2-biphenylylmethyl)amine in place of 2,3-dimethyl benzylamine.

LC/MS [M+H]$^+$=323, retention time=2.38 minutes.

Microwave Reactor

Where indicated in the above examples, the microwave reactor used was a Biotage Initiator™. Reactions were carried out using normal power output unless specified otherwise.

Mass-directed Automated HPLC

Where indicated in the above examples, purification by mass-directed automated HPLC was carried out using the following apparatus and conditions:

Hardware

Waters 2525 Binary Gradient Module

Waters 515 Makeup Pump

Waters Pump Control Module

Waters 2767 Inject Collect

Waters Column Fluidics Manager

Waters 2996 Photodiode Array Detector

Waters ZQ Mass Spectrometer

Gilson 202 fraction collector

Gilson Aspec waste collector

Software

Waters MassLynx version 4 SP2

Column

The columns used are Waters Atlantis, the dimensions of which are 19 mm×100 mm (small scale) and 30 mm×100 mm (large scale). The stationary phase particle size is 5 µm.

Solvents

A: Aqueous solvent=Water+0.1% Formic Acid
B: Organic solvent=Acetonitrile+0.1% Formic Acid
Make up solvent=Methanol:Water 80:20
Needle rinse solvent=Methanol Methods There are five methods used depending on the analytical retention time of the compound of interest. They have a 13.5-minute runtime, which comprises a 10-minute gradient followed by a 3.5 minute column flush and re-equilibration step.

Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)

Flow Rate

All of the above methods have a flow rate of either 20 mls/min (Small Scale) or 40 mls/min (Large Scale).

Chiral HPLC

Apparatus and conditions used to characterize enantiomeric purity of selected samples was as follows:

Method (A)
Instrument: Agilent 1100 Series Liquid Chromatogram
Column: Chiralpak AD (250 mm×4.6 mm; 10 um particle size)
Mobile phase: Heptane:absolute ethanol (70:30) v/v pump-mixed
Flow rate: 1 ml/min
Temperature: Ambient
U.V. Wavelength: 215 nm Method (B)
Instrument: Agilent 1100 Series Liquid Chromatogram
Column: Chiralpak AD (250 mm×4.6 mm; 10 um particle size)
Mobile phase: Heptane:absolute ethanol (50:50) v/v pump-mixed
Flow rate: 1 ml/min
Temperature: Ambient
U.V. Wavelength: 215 nm Method (C)
Instrument: Agilent 1100 Series Liquid Chromatogram
Column: Chiralpak AD (250 mm×4.6 mm; 10 um particle size)
Mobile phase: Heptane:absolute ethanol (80:20) v/v pump-mixed
Flow rate: 1 ml/min
Temperature: Ambient
U.V. Wavelength: 215 nm Method (D)
Instrument: Agilent 1100 Series Liquid Chromatogram
Column: Chiralpak AS (250 mm×4.6 mm; 10 um particle size)
Mobile phase: Heptane:absolute ethanol (80:20) v/v pump-mixed
Flow rate: 1 ml/min
Temperature: Ambient
U.V. Wavelength: 215 nm Liquid Chromatography/Mass Spectrometry Analysis of the above Examples by Liquid Chromatography/Mass Spectrometry (LC/MS) was carried out using the following apparatus and conditions:

Hardware
Agilent 1100 Gradient Pump
Agilent 1100 Autosampler
Agilent 1100 DAD Detector
Agilent 1100 Degasser
Agilent 1100 Oven
Agilent 1100 Controller
Waters ZQ Mass Spectrometer
Sedere Sedex 85

Software
Waters MassLynx version 4.0 SP2

Column

The column used is a Waters Atlantis, the dimensions of which are 4.6 mm×50 mm. The stationary phase particle size is 3 µm.

Solvents
A: Aqueous solvent=Water+0.05% Formic Acid
B: Organic solvent=Acetonitrile+0.05% Formic Acid Method
The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

The above method has a flow rate of 3 ml/mins.
The injection volume for the generic method is 5 ul.
The column temperature is 30 deg.
The UV detection range is from 220 to 330 nm.

Pharmacological Data

Compounds of the invention may be tested for in vitro biological activity at the P2X7 receptor in accordance with the following studies:

Ethidium Accumulation Assay

Studies were performed using NaCl assay buffer of the following composition (in mM): 140 mM NaCl, HEPES 10, N-methyl-D-glucamine 5, KCl 5.6, D-glucose 10, $CaCl_2$ 0.5 (pH 7.4). HEK293 cells, expressing human recombinant P2X7 receptors, were grown in poly-L-lysine pretreated 96 well plates for 18-24 h. (The cloning of the human P2X7 receptor is described in U.S. Pat. No. 6,133,434). The cells were washed twice with 350 µl of assay buffer before addition of 50 µl of test compound. The cells were then incubated at room temperature (19-21° C.) for 30 min before addition of ATP and ethidium (100 µM final assay concentration). The ATP concentration was chosen to be close to the $EC_{80}$ for the receptor type and was 1 mM for studies on the human P2X7 receptor. Incubations were continued for 8 or 16 min and were terminated by addition of 25 µl of 1.3M sucrose containing 5 mM of the P2X7 receptor antagonist reactive black 5 (Aldrich). Cellular accumulation of ethidium was determined by measuring fluorescence (excitation wavelength of 530 nm and emission wavelength of 620 nm) from below the plate with a Canberra Packard Fluorocount (Pangbourne, UK) or a Flexstation II (Molecular Devices)

Antagonist $pIC_{50}$ values for blocking ATP responses were determined using iterative curve fitting techniques.

Fluorescent Imaging Plate Reader (FLIPR) Ca Assay

Studies were performed using NaCl assay buffer of the following composition (in mM) for human P2X7: 137 NaCl; 20 HEPES; 5.37 KCl; 4.17 $NaHCO_3$; 1 $CaCl_2$; 0.5 $MgSO_4$; and 1 g/L of D-glucose (pH 7.4).

HEK293 cells, expressing human recombinant P2X7 receptors, were grown in poly-L-lysine pretreated 384 well plates for 42-48 h. (The cloning of the human P2X7 receptor is described in U.S. Pat. No. 6,133,434). The cells were washed three times with 80 µl of assay buffer, loaded for 1 h at 37° C. with 2 µM Fluo4 (Teflabs), washed three times again, and left with 30 µl buffer before the addition of 10 µl of 4× concentrated test compound. The cells were then incubated at room temperature for 30 mins before addition (on-line, by FLIPR384 or FLIPR3 instrument (Molecular Devices)) of Benzoylbenzoyl-ATP (BZATP) 60 µM final assay concentration. The BzATP concentration was chosen to be close to the $EC_{80}$ for the receptor type. Incubations and reading were continued for 90 sec, and intracellular calcium increase was determined by measuring fluorescence (excitation wavelength of 488 nm and emission wavelength of 516 nm) from below the plate, with FLIPR CCD camera. Antagonist $pIC_{50}$ values for blocking BzATP responses were determined using iterative curve fitting techniques.

The compounds of Examples 1-136 were tested in the FLIPR Ca Assay and/or the Ethidium Accumulation Assay for human P2X7 receptor antagonist activity and found to have pIC50 values >4.7 in the FLIPR Ca Assay and/or pIC50 values >5.5 in the Ethidium Accumulation Assay.

In Vivo Data

Rat Model of Neuropathic Pain

By placing loosely constrictive ligatures around the common sciatic nerve, a peripheral mononeuropathy can be produced, which thereby provides a rat model of neuropathic pain, Bennet et al., Pain, Vol. 33, pp 87-107 (1988). Adult male Random Hooded rats (180-200 g) from Charles River, UK were anaesthetised with isoflurane (3%). The sciatic nerve in the left leg was exposed at mid thigh level and 4 loose ligatures of Chromic 4.0 gut tied around the nerve as described by Bennet et al., Pain, Vol. 33, pp 87-107 (1988). The wound was closed and secured with staples. Sham rats underwent the same procedure but loose ligatures were not applied. The presence of mechanical (tactile) allodynia was assessed using manual application of Von Frey hair monofilaments. Monofilaments were applied in ascending order to the plantar region of the hind paw (range: 1.4 g-26 g). Each hair was applied for approx. 3-5 seconds until a paw withdrawal response was observed. After confirmation with reapplication of lower and/or higher hairs, the lowest hair to give a paw withdrawal was recorded as the threshold response (g). When stable allodynia was established rats were dosed orally 26-33 days post surgery with compound twice daily for 8 days with allodynia measurements recorded at least three times during the dosing period. N-[(2,4-dichlorophenyl)methyl]-1-methyl-5-oxo-prolinamide (E10) and N-{[2-chloro-3-(trifluoromethyl)phenyl]methyl}-1-methyl-5-oxoprolinamide (E51) significantly reversed CCl-induced mechanical allodynia compared to vehicle response.

Rat Model of Joint Pain

By measuring hypersensitivity post intra-articular injection of FCA into the knee, the effectiveness of a potential analgesic in reversing FCA-induced hypersensitivity can be assessed in a joint pain model of chronic inflammatory pain. Adult male Random Hooded rats (150-180 g) from Charles River, UK were briefly anaesthetised with isoflurane (3%). Rats were then injected with 150 µl of Freund's complete adjuvant (FCA) into the left knee joint (intra-articularly, i.art). The ability to bear weight on each hindlimb (weight bearing, g) was measured prior to and following surgery using a Dual Channel Weight Averager (Linton Instruments). When a stable difference in weight bearing was established between the injected and contralateral paws, rats were typically dosed orally (normally 13-17 days post surgery) with compound twice daily for 5 days with weight bearing measurements recorded daily. N-[(2,4-dichlorophenyl)methyl]-1-methyl-5-oxo-prolinamide (E10) and N-{[2-chloro-3-(trifluoromethyl)phenyl]methyl}-1-methyl-5-oxoprolinamide (E51) significantly reversed FCA (i.art)-induced difference in weight bearing compared to vehicle response and produced ED50's<20 mg/kg obtained from Area Under the Curve (AUC) calculations.

Rat Model of Acute Inflammatory Pain

A useful animal model for acute inflammatory pain is the Freund's Complete Adjuvant (FCA)-induced inflammation model. A similar model using carrageenan rather than FCA is described by Clayton et al. in Br. J. Pharmacol. 1997; 120, 219P. Adult male Random Hooded rats (180-220 g) from Charles River, UK received an intraplantar (i.pl) injection of 100 µl of FCA into the plantar surface of the left hind paw. The ability to bear weight on each hindlimb (weight bearing g) was measured prior to and 24 hours after the FCA injection using a Dual Channel Weight Averager (Linton Instruments). After the post-FCA reading, rats were typically dosed orally with compound after which weight bearing measurements were recorded. N-[(2,4-dichlorophenyl)methyl]-1-methyl-5-oxo-prolinamide (E10) and N-{[2-chloro-3-(trifluoromethyl)phenyl]methyl}-1-methyl-5-oxoprolinamide (E51) significantly reversed FCA (i.pl)-induced difference in weight bearing compared to vehicle response and produced ED50's<20 mg/kg obtained from dose response curves.

What is claimed is:

1. A compound of formula (I):

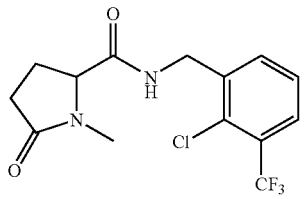

or a pharmaceutically acceptable salt or solvate thereof.

2. A compound which is N-{[2-chloro-3-(trifluoromethyl)phenyl]methyl}-1-methyl-5-oxoprolinamide.

3. A compound which is N-{[2-chloro-3-(trifluoromethyl)phenyl]methyl}-1-methyl-5-oxo-L-prolinamide.

4. A pharmaceutical composition which comprises the compound of claim 2 and a pharmaceutically acceptable carrier or excipient.

5. A pharmaceutical composition which comprises the compound of claim 3 and a pharmaceutically acceptable carrier or excipient.

6. A method of treating a human suffering from pain, which method comprises administering to said human an effective amount of the compound of claim 2.

7. A method of treating a human suffering from rheumatoid arthritis, which method comprises administering to said human an effective amount of the compound of claim 2.

8. A method of treating a human suffering from osteoarthritis, which method comprises administering to said human an effective amount of the compound of claim 2.

9. A method of treating a human suffering from Alzheimer's disease, which method comprises administering to said human an effective amount of the compound of claim 2.

10. A method of treating a human suffering from mild cognitive impairment associated with aging, which method comprises administering to said human an effective amount of the compound of claim 2.

11. A method of treating a human suffering from pain, which method comprises administering to said human an effective amount of the compound of claim 3.

12. A method of treating a human suffering from rheumatoid arthritis, which method comprises administering to said human an effective amount of the compound of claim 3.

13. A method of treating a human suffering from osteoarthritis, which method comprises administering to said human an effective amount of the compound of claim 3.

14. A method of treating a human suffering from Alzheimer's disease, which method comprises administering to said human an effective amount of the compound of claim 3.

15. A method of treating a human suffering from mild cognitive impairment associated with aging, which method comprises administering to said human an effective amount of the compound of claim 3.

* * * * *